United States Patent
Kozuka et al.

(10) Patent No.: US 10,261,681 B2
(45) Date of Patent: *Apr. 16, 2019

(54) METHOD FOR DISPLAYING A MEDICAL IMAGE AND A PLURALITY OF SIMILAR MEDICAL IMAGES OBTAINED FROM A CASE SEARCH SYSTEM

(71) Applicant: Panasonic Intellectual Property Management Co., Ltd., Osaka (JP)

(72) Inventors: Kazuki Kozuka, Osaka (JP); Kazutoyo Takata, Fukui (JP); Kenji Kondo, Fukui (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/264,882

(22) Filed: Sep. 14, 2016

(65) Prior Publication Data

US 2017/0090739 A1    Mar. 30, 2017

(30) Foreign Application Priority Data

Sep. 30, 2015   (JP) .................. 2015-193500

(51) Int. Cl.
   *G06F 3/0485*   (2013.01)
   *G06F 3/0482*   (2013.01)
   (Continued)

(52) U.S. Cl.
   CPC .......... *G06F 3/0485* (2013.01); *A61B 5/7425* (2013.01); *G06F 3/0482* (2013.01);
   (Continued)

(58) Field of Classification Search
   CPC ......... A61B 2560/0487; G06F 3/04817; G06F 3/0482; G06F 3/04845; G06F 3/04847; G06F 3/0485; G06F 3/0486; G06F 19/321
   (Continued)

(56) References Cited

U.S. PATENT DOCUMENTS 6,546,188 B1 *   4/2003   Ishii ..................... G11B 27/031
                                                        386/280
8,330,717 B2 *  12/2012   Kawakami .............. G06F 3/038
                                                        345/157
(Continued)

FOREIGN PATENT DOCUMENTS

| JP | 2008-257292 | 10/2008 |
| JP | 2010-017410 | 1/2010 |
| JP | 2012-035124 | 2/2012 |

OTHER PUBLICATIONS

Akira Oosawa et al., "Development of "Synapse Case Match", Content-based Image Retrieval System for Supporting Image Diagnosis", Fujifilm Research&Development, No. 58, 2013, pp. 11-14.

*Primary Examiner* — Andrew R Dyer
(74) *Attorney, Agent, or Firm* — Wenderoth, Lind & Ponack, L.L.P.

(57) ABSTRACT

A control method displays a display screen including a first display area that displays a target medical image and a second display area that displays a received plurality of similar medical images including first and second similar medical images, the first and second similar medical images being displayed adjacently to each other in the second display area. If a first operation is sensed, the control method displays the target medical image adjacent to the first similar medical image in the second display area, and also display the target medical image adjacent to the second similar medical image in the second display area. The first operation (Continued)

is an operation of moving the target medical image adjacent to the first similar medical image in the second display area, and also moving the target medical image adjacent to the second similar medical image in the second display area.

15 Claims, 50 Drawing Sheets

(51) Int. Cl.
   *G06F 3/0486* (2013.01)
   *A61B 5/00* (2006.01)
   *G06F 3/0484* (2013.01)
   *G06F 19/00* (2018.01)
   *G16H 30/20* (2018.01)
   *G16H 50/70* (2018.01)
   *A61B 5/055* (2006.01)

(52) U.S. Cl.
   CPC .......... *G06F 3/0484* (2013.01); *G06F 3/0486* (2013.01); *G06F 19/00* (2013.01); *G16H 30/20* (2018.01); *G16H 50/70* (2018.01); *A61B 5/055* (2013.01); *A61B 2560/0487* (2013.01); *G06F 2203/04803* (2013.01)

(58) Field of Classification Search
   USPC ........................................ 715/243, 246, 253
   See application file for complete search history.

(56) References Cited

U.S. PATENT DOCUMENTS

| | | | |
|---|---|---|---|
| 2002/0094119 A1* | 7/2002 | Sahadevan | G06T 7/0012 382/132 |
| 2005/0226405 A1* | 10/2005 | Fukatsu | G06Q 50/22 380/1 |
| 2005/0243381 A1* | 11/2005 | Hill | H04N 1/00132 358/453 |
| 2006/0048069 A1* | 3/2006 | Igeta | G06F 3/0486 715/769 |
| 2006/0241370 A1* | 10/2006 | Kramp | A61B 6/04 600/407 |
| 2008/0243395 A1 | 10/2008 | Oosawa et al. | |
| 2009/0043157 A1* | 2/2009 | Hirakawa | A61B 1/00045 600/109 |
| 2010/0231509 A1* | 9/2010 | Boillot | G06F 3/011 345/156 |
| 2011/0219297 A1 | 9/2011 | Oda | |
| 2013/0088512 A1 | 4/2013 | Suzuki et al. | |
| 2013/0311502 A1* | 11/2013 | Takata | G06F 17/30253 707/758 |
| 2014/0072193 A1* | 3/2014 | Motomura | G06T 7/0012 382/128 |
| 2014/0218768 A1* | 8/2014 | Watanabe | H04N 1/387 358/1.18 |

* cited by examiner

FIG. 14

| DISEASE LIST | 730 | |
|---|---|---|
| MYCOSIS | 14 | 731 |
| ASPERGILLOSIS | 8 | 732 |
| CRYPTOCOCCOSIS | 6 | 733 |
| NEOPLASTIC | 13 | 734 |
| LUNG CANCER | 10 | 735 |
| METASTATIC LUNG CANCER | 3 | 736 |
| NON-NEOPLASTIC | 6 | 737 |
| LUNG ABSCESS | 4 | 738 |
| SARCOIDOSIS | 1 | 739 |
| SEPTIC EMBOLI | 1 | 740 |
| MYCOBACTERIOSIS | 6 | 741 |
| NTM | 4 | 742 |
| TUBERCULOSIS | 2 | 743 |
| OTHER | 2 | 744 |
| BRONCHIECTASIS | 1 | 745 |
| ... | 1 | |

FIG. 17

LESION DISTRIBUTION  /750

☐ DIFFUSE /751        ☐ MULTIPLE /755
▦ SEGMENTAL /752      ☐ SUBPLEURAL /756
☐ BRONCHIAL /753      ☐ HEMATOGENOUS /757
☐ BILATERAL /754

FIG. 18

LESION DISTRIBUTION  /750

☐ DIFFUSE /751        ☐ MULTIPLE /755
▦ SEGMENTAL /752      ☐ SUBPLEURAL /756
☐ BRONCHIAL /753      ☐ HEMATOGENOUS /757
☑ BILATERAL /754

FIG. 20

LESION DISTRIBUTION ⟋750

☐ DIFFUSE ⟋751   ☐ MULTIPLE ⟋755
▨ SEGMENTAL ⟋752   ☐ SUBPLEURAL ⟋756
☑ BRONCHIAL ⟋753   ☐ HEMATOGENOUS ⟋757
☐ BILATERAL ⟋754

FIG. 22

LESION DISTRIBUTION  /750
☐ DIFFUSE /751        ☐ MULTIPLE /755
▨ SEGMENTAL /752      ☑ SUBPLEURAL /756
☐ BRONCHIAL /753      ☐ HEMATOGENOUS /757
☐ BILATERAL /754

| 1100 | PATIENT ID | 123456 |
|---|---|---|
| 1200 | NAME | PANA, TARO |
| 1300 | AGE | 28 |
| 1400 | SEX | MALE |
| 1500 | MEDICAL HISTORY | N/A |
| 1600 | FAMILY HISTORY | N/A |
| 1700 | CHIEF COMPLAINT | COUGHING |
| 1800 | EXAMINATION INFORMATION | (SEE FIG. 25) |
| 1900 | DEFINITE DIAGNOSIS | MYCOPLASMA PNEUMONIA |

| | | |
|---|---|---|
| 1810 | EXAMINATION ID | 13227895 |
| 1820 | EXAMINATION DATE | 20XX／2／5 10:00 |
| 1830 | EXAMINATION TYPE | BLOOD TEST |
| 1840 | EXAMINATION RESULT | YYYY1 |

| | |
|---|---|
| EXAMINATION ID | 13227903 |
| EXAMINATION DATE | 20XX／2／5 11:00 |
| EXAMINATION TYPE | PLAIN X-RAY (CHEST) |
| EXAMINATION RESULT | YYYY2 |

| | |
|---|---|
| EXAMINATION ID | 13227989 |
| EXAMINATION DATE | 20XX／2／9 9:00 |
| EXAMINATION TYPE | CT (CHEST) |
| EXAMINATION RESULT | YYYY3 |

| 1810 | EXAMINATION ID | 13227989 |
| 3100 | OBSERVATIONS | MULTIPLE NODULES FROM 0.5 cm TO 1 cm IN SIZE IN RIGHT LUNG FIELD... |
| 3200 | DIAGNOSIS | INFLAMMATORY NODULES OR TUBERCULOSIS SUSPECTED. |

FIG. 28

| 4000 | |
|---|---|
| 4100 — SIMILAR CASE ID | SIM5232 |
| 4200 — SLICE ID | CT149400025 |
| 4300 — ROI INFORMATION | $x_l, y_t, x_r, y_b$ |
| 4400 — IMAGE FEATURE DATA | f1, f2, f3, ..., fN |
| 4500 — THUMBNAIL IMAGE DATA | $(I_{0, 0}, I_{0, 1}, ..., I_{w-1, h-1})$ |
| 4600 — LESION DISTRIBUTION INFORMATION | |
| 4700 — DEFINITE DIAGNOSIS (MAJOR DISEASE CLASSIFICATION) | NEOPLASTIC |
| 4800 — DEFINITE DIAGNOSIS (FINE DISEASE CLASSIFICATION) | LUNG CANCER |

| | | | | | |
|---|---|---|---|---|---|
| DIFFUSE | SEGMENTAL | BRONCHIAL | BILATERAL | MULTIPLE | SUBPLEURAL | HEMATOGENOUS |
| 0 | 0 | 0 | 0 | 0 | 0 | 1 |
| 4610 | 4620 | 4630 | 4640 | 4650 | 4660 | 4670 |

FIG. 31

| PATIENT ID | PATIENT NAME | EXAMINATION DATE | EXAMINATION ID | EXAMINATION TYPE |
|---|---|---|---|---|
| 443982 | YAMADA, ICHIRO | 20XX/12/1 | 23982874 | MR (HEAD) |
| 123456 | PANA, TARO | 20XX/5/8 | 13227989 | CT (CHEST) |
| 345455 | ... | ... | ... | ... |
| 235982 | ... | ... | ... | ... |

~800

| SERIES ID | DEFINITION | IMAGE |
|---|---|---|
|  |  |  |
|  |  |  |
|  |  |  |

~810

FIG. 32
| PATIENT ID | PATIENT NAME | EXAMINATION DATE | EXAMINATION ID | EXAMINATION TYPE |
|---|---|---|---|---|
| 443982 | YAMADA, ICHIRO | 20XX/12/1 | 23982874 | MR (HEAD) |
| 123456 | PANA, TARO | 20XX/5/8 | 13227989 | CT (CHEST) |
| 345455 | ... | ... | ... | ... |
| 235982 | ... | ... | ... | ... |
~800
| SERIES ID | DEFINITION | IMAGE |
|---|---|---|
| CT152729 | LUNG FIELD CONDITION SLICE THICKNESS: 5 mm | 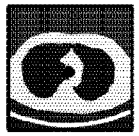 |
| CT152730 | LUNG FIELD CONDITION SLICE THICKNESS: 1 mm | 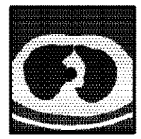 |
| CT152731 | MEDIASTINUM CONDITION SLICE THICKNESS: 5 mm |  |
~810

| NUMBER OF ROWS | 2 |
|---|---|
| NUMBER OF COLUMNS | 2 |

~4411

| POSITION | SLICE ID |
|---|---|
| ROW 1 COLUMN 1 | CT12353515 |
| ROW 1 COLUMN 2 | — |
| ROW 2 COLUMN 1 | — |
| ROW 2 COLUMN 2 | — |

| DISEASE ID | MAJOR DISEASE CLASSIFICATION | FINE DISEASE CLASSIFICATION | NO. OF CASES | SIMILAR CASE IDs |
|---|---|---|---|---|
| DIS528 | NEOPLASTIC | LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NON-NEOPLASTIC | LUNG ABSCESS | 4 | ... |
| ... | MYCOBACTERIOSIS | NTM | 4 | ... |
| ... | ... | ... | ... | ... |

FIG. 39

DISEASE LIST  730

| | |
|---|---|
| LUNG CANCER | 10 |
| ASPERGILLOSIS | 8 |
| CRYPTOCOCCOSIS | 6 |
| LUNG ABSCESS | 4 |
| NTM | 4 |
| METASTATIC LUNG CANCER | 3 |
| TUBERCULOSIS | 2 |
| INFLAMMATORY NODULES | 1 |
| SEPTIC EMBOLI | 1 |
| BRONCHIECTASIS | 1 |
| UNKNOWN | 1 |

FIG. 40

DISEASE LIST  730

| | |
|---|---|
| MYCOSIS | 14 |
| NEOPLASTIC | 13 |
| NON-NEOPLASTIC | 6 |
| MYCOBACTERIOSIS | 6 |
| OTHER | 2 |

| DISTRIBUTION NAME | NO. OF CASES | SIMILAR CASE IDs |
|---|---|---|
| DIFFUSE | 3 | SIM2521, SIM4123, SIM5225 |
| SEGMENTAL | 0 | N/A |
| BRONCHIAL | 2 | SIM0006, SIM1892, SIM4399 |
| BILATERAL | 12 | ... |
| MULTIPLE | 22 | ... |
| SUBPLEURAL | 0 | N/A |
| HEMATOGENOUS | 5 | ... |

FIG. 49

| 4000 | |
|---|---|
| 4100 — SIMILAR CASE ID | SIM5232 |
| 4200 — SLICE ID | CT149391025 |
| 4300 — ROI INFORMATION | $x_l, y_t, x_r, y_b$ |
| 4400 — IMAGE FEATURE DATA | f1, f2, f3, ..., fN |
| 4500 — THUMBNAIL IMAGE DATA | $(I_{0,0}, I_{0,1}, ..., I_{w-1, h-1})$ |
| 4600 — LESION DISTRIBUTION INFORMATION | |
| 4700 — DEFINITE DIAGNOSIS (MAJOR DISEASE CLASSIFICATION) | NEOPLASTIC |
| 4800 — DEFINITE DIAGNOSIS (FINE DISEASE CLASSIFICATION) | LUNG CANCER |
| 4900 — PLEURAL REGION INFORMATION | $xp_l, yp_t, xp_r, yp_b$ |

| | |
|---|---|
| 4610 — DIFFUSE | 0 |
| 4620 — SEGMENTAL | 0 |
| 4630 — BRONCHIAL | 0 |
| 4640 — BILATERAL | 0 |
| 4650 — MULTIPLE | 0 |
| 4660 — SUBPLEURAL | 0 |
| 4670 — HEMATOGENOUS | 1 |

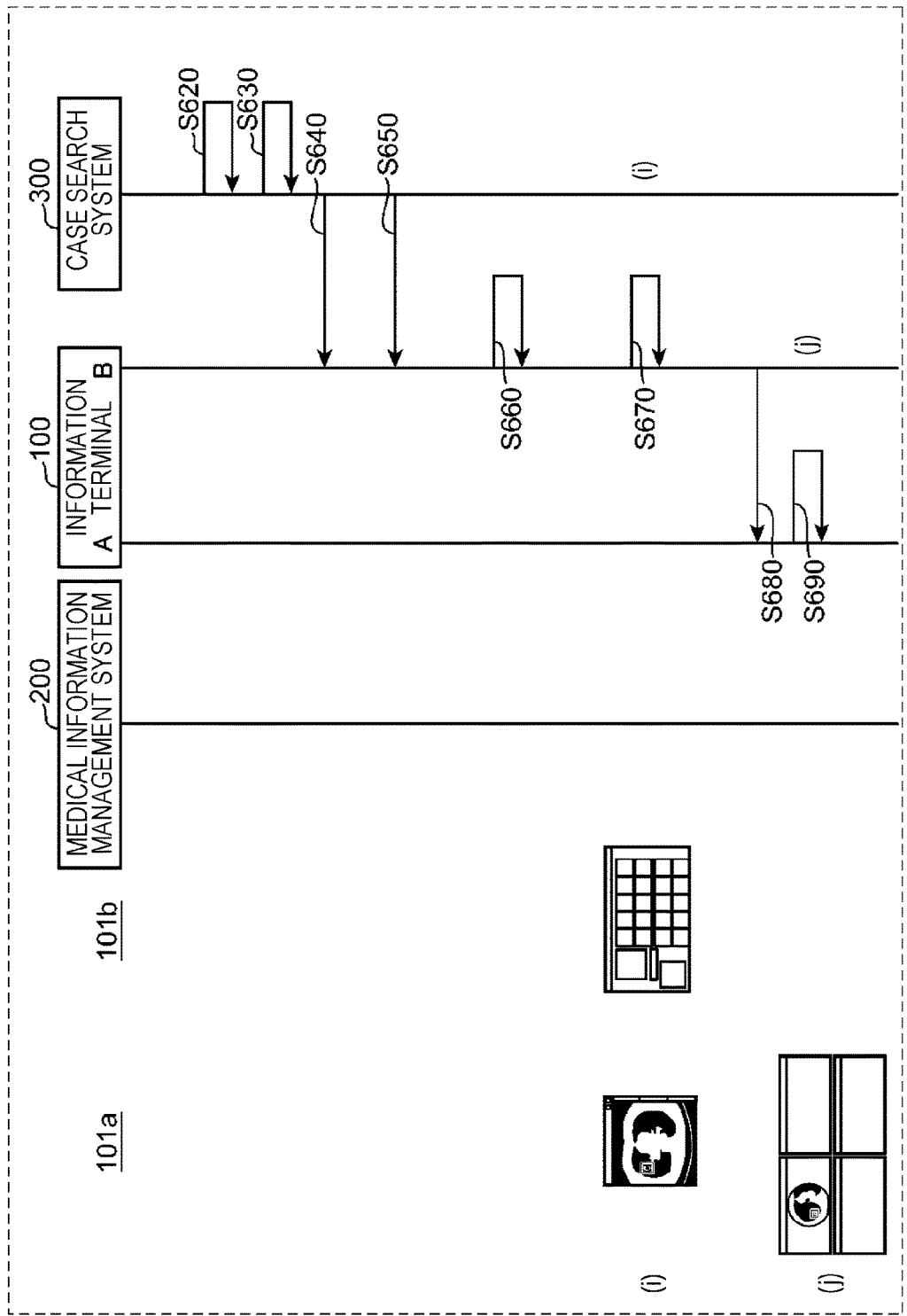

METHOD FOR DISPLAYING A MEDICAL IMAGE AND A PLURALITY OF SIMILAR MEDICAL IMAGES OBTAINED FROM A CASE SEARCH SYSTEM

BACKGROUND

1. Technical Field

The present disclosure relates to a control method for an information terminal and a recording medium for searching similar medical images resembling a medical image to be interpreted.

2. Description of the Related Art

Recently, medical imaging devices, such as computed tomography (CT) and magnetic resonance imaging (MRI), for example, are developing and proliferating. These technologies such as CT and MRI enable the acquisition of large amounts of digitized high-definition medical images. Additionally, medical images interpreted by physicians are being stored successively, together with interpretation reports, in picture archiving and communication systems (PACS). At this point, as disclosed in Japanese Unexamined Patent Application Publication No. 2008-257292, for example, technologies are started to be developed in which past cases already stored in a PACS may be searched to find and use past medical images resembling a new medical image to be interpreted as a reference when interpreting the new medical image.

SUMMARY

One non-limiting and exemplary embodiment provides further improvements.

In one general aspect, the techniques disclosed here feature a control method for an information terminal, the control method being executed by a computer of the information terminal, and comprising: receiving, from a case search system, a plurality of similar medical images having a certain similarity to a target medical image to be interpreted, the received plurality of similar medical images including a first similar medical image and a second similar medical image; causing a display to display a display screen including a first display area that displays the target medical image and a second display area that displays the received plurality of similar medical images, the first similar medical image and the second similar medical image being displayed adjacent to each other in the second display area; and if a first operation is sensed, displaying the target medical image adjacent to the first similar medical image in the second display area, and also displaying the target medical image adjacent to the second similar medical image in the second display area, wherein the first operation is an operation of moving the target medical image adjacent to the first similar medical image in the second display area, and also moving the target medical image adjacent to the second similar medical image in the second display area.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 14 is an enlarged view of a disease list display area;

FIG. 17 is an enlarged view of a distribution list display area;

FIG. 18 is a diagram illustrating a distribution list display area in which a checkmark has been input into a bilateral check box;

FIG. 20 is a diagram illustrating a distribution list display area in which a checkmark has been input into a bronchial check box;

FIG. 22 is a diagram illustrating a distribution list display area in which a checkmark has been input into a subpleural check box;

FIG. 24 is a diagram illustrating a data structure of patient information;

FIG. 25 is a diagram illustrating a data structure of examination information registered in the patient information illustrated in FIG. 24;

FIG. 27 is a diagram illustrating a data structure of a diagnosis report;

FIG. 28 is a diagram illustrating a data structure of similar case data;

FIG. 31 is a diagram illustrating an examination list screen;

FIG. 32 is a diagram illustrating an examination list screen after an examination is selected;

FIG. 36 is a diagram illustrating a data structure of display box management information;

FIG. 38 is a diagram illustrating a data structure of a disease list generated in S1300 of FIG. 37;

FIG. 39 is a diagram illustrating a first display example of a disease list display area;

FIG. 40 is a diagram illustrating a second display example of a disease list display area;

FIG. 49 is a diagram illustrating a data structure of similar case data with added pleural region information;

FIG. 53 is a sequence diagram illustrating a process in which a case search system receives a similar case search request, and replies to an information terminal with similar case search results.

DETAILED DESCRIPTION

Figure 1:
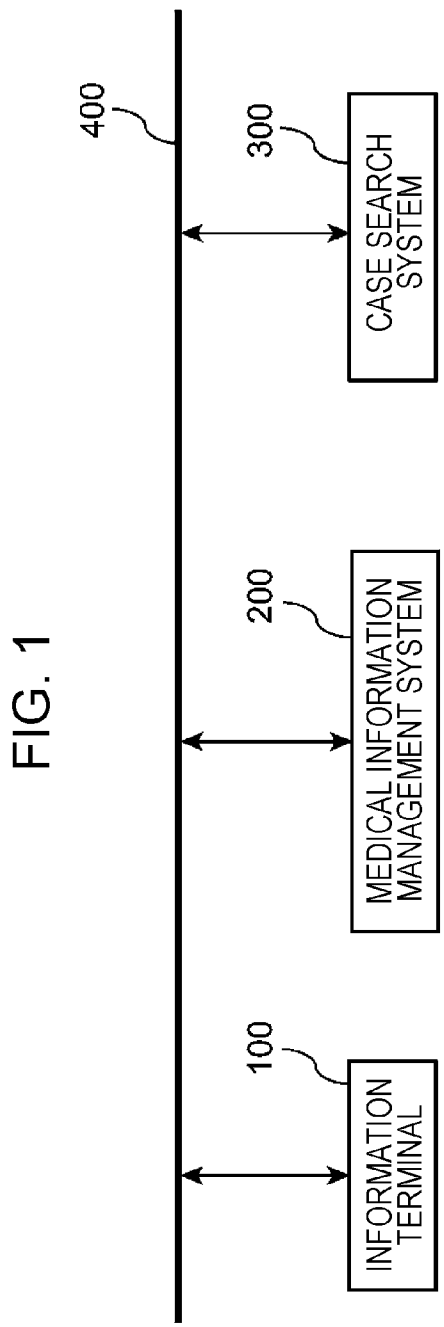
FIG. 1 is an overall configuration diagram of a hospital information system to which an information terminal according to the present embodiment has been applied.

Findings that LED to an Aspect According to the Present Disclosure

First, a focus of an aspect according to the present disclosure will be described.

Japanese Unexamined Patent Application Publication No. 2008-257292 discloses an image diagnosis support device that presents case images useful for diagnosing a disorder or information such as statistical information related to the disorder when performing image diagnosis based on an image to be diagnosed. A search results screen by the image diagnosis support device displays the image to be diagnosed and information about representative cases for respective disorders. Specifically, the search results screen displays i) images of representative cases of the top three disorders A, D, and G, ii) for each disorder, the similarity with the image to be diagnosed, the number of registered cases, and the number of representative cases, iii) the number of search hits (the total number of disorders found by search), and iv) elements such as a "Next Page" software button for referencing information about other disorders that does not fit on a single screen (see paragraphs [0062] to [0063] and FIG. 6(E)).

In Japanese Unexamined Patent Application Publication No. 2008-257292, on the search results screen, images of representative cases for each disorder are displayed in order, starting from a position close to the image to be diagnosed and proceeding farther away. For this reason, when comparing the image to be diagnosed to the images of the representative cases for each disorder, depending on the display position of the image of the representative case that the physician wants to compare (for example, disorder G in FIG. 6(E)), there may be images of other representative cases interposed in between, and the physician's gaze moves over a greater distance. This not only increases the physical burden associated with shifting one's gaze back and forth, but may also lead to decreased diagnosis accuracy. The reason for this is because when the physician compares the image to be diagnosed with an image of a representative case, the physician is comparing in detail many characteristics such as the position, size, shape, and distribution of shadows corresponding to lesions in the images. Consequently, if the image to be diagnosed and an image of a representative case are not displayed adjacently but instead at distant positions, making the above detailed comparison becomes difficult, and as a result, reduced diagnosis accuracy is conceivable.

Japanese Unexamined Patent Application Publication No. 2012-35124 discloses a medical image display device enabling easier comparative interpretation of tomographic image data in multiple series from the same patient. Specifically, a base/target image data display screen include a base tomographic image data display area, a thumbnail image data display area, and a target (target of comparison) image data display area. Base tomographic image data is displayed in the base tomographic image data display area. Also, comparison thumbnail image data is displayed in the thumbnail image data display area. In this state, by dragging and dropping comparison thumbnail image data displayed in the thumbnail image data display area to the target image data display area, comparison tomographic image data corresponding to the comparison thumbnail image data is displayed in the target image data display area (see paragraphs [0046] to [0049] and FIG. 7). Herein, comparative interpretation refers to comparative interpretation using image data obtained from the same patient by different diagnostic imaging devices or under different imaging conditions, or comparative interpretation using older and more recent image data obtained from the same patient by the same diagnostic imaging device.

In this way, Japanese Unexamined Patent Application Publication No. 2012-35124 presupposes the comparison of images from the same patient, and contains no description regarding comparison with images from other patients. If the images are from the same patient, characteristics such as the positions of shadows corresponding to lesions in the images will be the same to some degree. For this reason, comparative interpretation may be performed more efficiently by performing a detailed comparison using enlarged tomographic image data, rather than performing a comparison using thumbnail images obtained by reducing the tomographic image data. Given the above, when comparing medical images to each other, the idea of displaying the comparison thumbnail image data adjacent to the base tomographic image data and narrowing down the comparison thumbnail image data while in the thumbnail image stage is not disclosed.

In Osawa et al., "Development of 'SYNAPSE Case Match', Content-based Image Retrieval System for Supporting Image Diagnosis", Fuji Film Research & Development (58), Fuji Film Corporation, p. 11-14, Mar. 27 2013, the authors disclose a similar case search system that, through a function of searching for similar cases in the past using a lesion image, instantly extracts and presents accurate information from clinical knowledge accumulated in a system such as a PACS discussed earlier, and supports image diagnosis by a physician. Specifically, this system searches for case images with features resembling the features of an examination image, and displays multiple case images in order of similarity. Additionally, one reference case image is selected from among multiple displayed case images, and displayed next to the examination image (see p. 12 "2.2 Features of the System" and FIG. 3).

The system disclosed by Osawa et al. displays the selected reference case image next to the examination image. Consequently, when comparing medical images to each other, the idea of displaying the examination image adjacent to case images and narrowing down the search results while in the thumbnail image stage is not disclosed.

Through consideration of the above issues, the inventors conceived the following aspects.

An aspect of the present disclosure is a control method for an information terminal, the control method being executed by a computer of the information terminal, and including:

receiving, from a case search system, a plurality of similar medical images having a certain similarity to a target medical image to be interpreted, the received plurality of similar medical images including a first similar medical image and a second similar medical image;

causing a display to display a display screen including a first display area that displays the target medical image and a second display area that displays the received plurality of similar medical images, the first similar medical image and the second similar medical image being displayed adjacent to each other in the second display area; and if a first operation is sensed, displaying the target medical image adjacent to the first similar medical image in the second display area, and also displaying the target medical image adjacent to the second similar medical image in the second display area, wherein the first operation is an operation of moving the target medical image adjacent to the first similar medical image in the second display area, and also moving the target medical image adjacent to the second similar medical image in the second display area.

According to this aspect, multiple similar medical images having a certain similarity to a target medical image are received from a case search system, and the multiple received similar medical images are displayed on a display. Consequently, from among a very large number of medical images registered in a medical image database, similar medical images that serve as a reference for determining the disease causing a lesion appearing in the target medical image are extracted effectively and presented to the physician.

In addition, according to this aspect, if an operation is performed to move the target medical image being displayed in the first display area in between a first similar medical image and a second similar medical image being displayed in the second display area, the target medical image may be displayed adjacently between the first similar medical image and the second similar medical image. Consequently, the physician is able to display the target medical image adjacently to similar medical images that the physician wants to compare and investigate in detail, and the movement of the physician's gaze may be decreased greatly.

The reasons are described below. The positions of shadows corresponding to lesions included in similar medical images are various. For this reason, depending on the positions of shadows included in similar medical images, when making a comparison to a shadow included in a target medical image, gaze movement may increase in some situations. For example, consider a situation in which the shadow included in the target medical image exists in the right lung, while the shadow included in a similar medical image exists in the left lung. In this situation, if the target medical image is placed on the right side of the similar medical image in the second display area, the distance between the shadow included in the target medical image and the shadow included in the similar medical image becomes shorter. Consequently, the movement of the physician's gaze may be decreased greatly. As a result, the physical burden on the physician that is associated with shifting one's gaze back and forth is decreased, which may also lead to improved diagnosis accuracy.

The above aspect may also be configured so that, for example, when displaying the target medical image adjacent to the first similar medical image in the second display area, and also displaying the target medical image adjacent to the second similar medical image in the second display area, the target medical image is displayed emphasized compared to the plurality of similar medical images.

Since the target medical image and the similar medical images are similar to each other, when the target medical image is displayed in the second display area, there is a risk of being unable to determine at a glance which image is the target medical image.

According to this aspect, the target medical image displayed in the second display area is displayed emphasized compared to the multiple similar medical images being displayed in the second display area. For this reason, it is possible to determine immediately which image is the target medical image.

The above aspect may also be configured so that, for example, when displaying the target medical image adjacent to the first similar medical image in the second display area, and also displaying the target medical image adjacent to the second similar medical image in the second display area, display sizes of the target medical image, the first similar medical image, and the second similar medical image are set to a same size.

According to this aspect, the display sizes of the target medical image, the first similar medical image, and the second similar medical image become the same size, thereby enabling easier comparison of the sizes of the lesions included in each of the medical images.

The above aspect may also be configured so that, for example, the received plurality of similar medical images additionally includes a third similar medical image, a shape of the second display area is rectangular, a number of images displayed horizontally in the second display area is fixed, in the second display area, the first similar medical image, the second similar medical image, and the third similar medical image are displayed adjacent to each other in order from left to right on a same row, the third similar medical image is displayed adjacent to a right edge of the second display area, and when displaying the target medical image adjacent to the first similar medical image in the second display area, and also displaying the target medical image adjacent to the second similar medical image in the second display area, the third similar medical image is not displayed in the second display area.

If the target medical image is moved in between the first similar medical image and the second similar medical image, the number of medical images arranged horizontally in the second display area increases by 1. In this situation, if all similar medical images in the horizontal direction that were being displayed before the target medical image was moved are to keep being displayed even after the target medical image is moved, it will be necessary to reduce the display size of each of the medical images displayed horizontally. However, if the display size is reduced, there is a risk that the observation of lesions included in the medical images may become more difficult.

According to this aspect, when the target medical image is displayed in between the first similar medical image and the second similar medical image, the number of medical images to be displayed horizontally in the second display area is fixed, and a third similar medical image is not displayed in the second display area. For example, the second similar medical image is moved to the right, the second similar medical image is displayed at the position where the third similar medical image was being displayed, and the target medical image is inserted at the position where the second similar medical image was being displayed. For this reason, it is not necessary to reduce the display size of the medical images. As a result, a situation in which the observation of lesions becomes more difficult does not occur.

The above aspect may also be configured so that, for example, if the computer senses an operation of displaying the target medical image adjacent to the second similar medical image in the second display area, and also displaying the target medical image adjacent to the third similar medical image in the second display area, the computer displays the target medical image adjacent to the second similar medical image in the second display area, also displays the target medical image adjacent to the right edge of the second display area in the second display area, and also does not display the third similar medical image in the second display area.

According to this aspect, if an operation of moving the target medical image in between the second similar medical image and the third similar medical image is sensed, the target medical image is displayed adjacently between the second similar medical image and the right edge of the second display area, while the third similar medical image is not displayed in the second display area. In other words, the target medical image is inserted at the position where the third similar medical image was being displayed. Consequently, when the user wants to compare the target medical image to the second similar medical image, this comparison may be performed favorably.

The above aspect may also be configured so that, for example, a scroll element is displayed on the display screen, and if an operation performed on the scroll element is sensed, the similar medical images on the row including the first similar medical image and the target medical image are scrolled.

According to this aspect, when an operation performed on a scroll element is sensed, the similar medical images on the row including the first similar medical image and the target medical image are scrolled. For this reason, the third similar medical image that is no longer displayed in the second display area due to the insertion of the target medical image may be displayed by scrolling. Consequently, it becomes possible to compare the target medical image and the third similar medical image that was being displayed adjacent to the right edge of the second display area. Thus, when the user wants to compare the target medical image and the third similar medical image, it is sufficient for the user to operate the scroll element.

The above aspect may also be configured so that, for example, the received plurality of similar medical images additionally includes a fourth similar medical image, the fourth similar medical image is displayed adjacent to the right edge of the second display area on the row including the first similar medical image, and if the computer senses an operation of displaying the target medical image adjacent to the second similar medical image in the second display area, and also displaying the target medical image adjacent to the third similar medical image in the second display area, the computer displays the target medical image adjacent in between the third similar medical image and the right edge of the second display area in the second display area, and also does not display the fourth similar medical image in the second display area.

According to this aspect, if an operation of moving the target medical image in between the second similar medical image and the third similar medical image is sensed, the target medical image is displayed adjacently between the third similar medical image and the right edge of the second display area. In other words, the third similar medical image is moved to the left, and the target medical image is inserted at the position where the third similar medical image was being displayed. Consequently, it becomes possible to compare the target medical image and the third similar medical image that was being displayed adjacent to the right edge of the second display area.

Additionally, the number of medical images to be displayed horizontally in the second display area is fixed, and a fourth similar medical image is not displayed in the second display area. For this reason, it is not necessary to reduce the display size of the medical images. As a result, a situation in which the observation of lesions becomes more difficult does not occur.

The above aspect may also be configured so that, for example, even if the computer senses an operation of displaying the target medical image adjacent to the second similar medical image in the second display area, and also displaying the target medical image adjacent to the third similar medical image in the second display area, the computer does not display the target medical image adjacent to the second similar medical image in the second display area, and also does not display the target medical image adjacent to the third similar medical image in the second display area.

If the target medical image is inserted in between the second similar medical image and the third similar medical image, since the number of medical images to be displayed horizontally in the second display area is fixed, the third similar medical image is not displayed in the second display area. In such a situation, if the physician wants to compare the third similar medical image and the target medical image, the operation of moving the target medical image becomes pointless.

According to this aspect, even if an operation of moving the target medical image in between the second similar medical image and the third similar medical image is sensed, it is configured so that the target medical image may not be displayed adjacently between the second similar medical image and the third similar medical image. For this reason, a situation in which the operation of moving the target medical image by the physician becomes pointless may be avoided preemptively.

The control method according to the above aspect additionally may include, for example, sensing specifying information indicating a region of interest in the target medical image, transmitting information indicating features of the region of interest to the case search system, and receiving, from the case search system, similar medical images having the certain similarity with the features of the region of interest.

The control method according to the above aspect additionally may include, for example, sensing specifying information indicating a region of interest in the target medical image, transmitting the target medical image and the specifying information to the case search system, and receiving, from the case search system, similar medical images having the certain similarity with features of the region of interest obtained from the target medical image and the specifying information.

The above aspect may also be configured so that, for example, the target medical image is a medical image of lungs, each of the similar medical images is a medical image of lungs, and includes a corresponding region of interest indicating an affected area in the similar medical image, the display screen includes first distribution information enabling selection of similar medical images in which a size of the corresponding region of interest belongs to a certain first range indicating a wide range of a lung region, second distribution information enabling selection of similar medical images in which the size of the corresponding region of interest belongs to a certain second range, lower than the first range, indicating a part of a lung region, and third distribution information enabling selection of similar medical images in which the corresponding region of interest includes pleura, and if a selection of any one from the first distribution information to the third distribution information is sensed, similar medical images corresponding to the one selected distribution information are selected and displayed in the second display area.

According to this aspect, multiple similar medical images displayed in the second display area additionally may be sorted based on the distribution pattern of the corresponding region of interest. Consequently, for example, similar medical images for which the distribution of the affected area resembles the target medical image may be selected efficiently from among a large number of displayed similar medical images.

The above aspect may also be configured so that, for example, the second display area includes a plurality of individual areas for respectively displaying each of the received plurality of similar medical images, if a selection of the first distribution information is sensed, similar medical images corresponding to the first distribution information are displayed respectively in each of the individual areas, at an initial display size, if a selection of the second distribution information is sensed, similar medical images corresponding to the second distribution information are displayed respectively in each of the individual areas, zoomed in and centered on the corresponding region of interest in each of the similar medical images corresponding to the second distribution information, and if a selection of the third distribution information is sensed, similar medical images corresponding to the third distribution information are displayed respectively in each of the individual areas, zoomed in and centered on the corresponding region of interest in each of the similar medical images corresponding to the third distribution information, and in a state including the pleura.

According to this aspect, when sorting similar medical images based on the distribution pattern of the corresponding region of interest, a display is presented according to the sort as well as the distribution pattern. Consequently, the physician is not required to sort similar medical images based on the distribution pattern of the corresponding region of interest, and then perform other processes separately, such as zooming the similar medical images according to the distribution pattern or centering the similar medical images on the corresponding region of interest. For this reason, even after images are sorted based on the distribution pattern of the corresponding region of interest, the subsequent burdensome work of repeatedly performing similar operations on the large number of sorted similar medical images one by one may be reduced greatly. As a result, lapses in the physician's thinking or concentration, which should be directed at making a medical diagnosis, due to the burden of such operations may be decreased greatly, and the physician's thinking and concentration may be directed towards the original task of making a medical diagnosis. For this reason, it is possible to improve the accuracy of medical diagnosis.

The above aspect may also be configured so that, for example, the first distribution information is information indicating a distribution belonging to a bilateral, a multiple, a diffuse, or a hematogenous category, the second distribution information is information indicating a distribution belonging to a segmental or a bronchial category, and the third distribution information is information indicating a distribution belonging to a subpleural category.

According to this aspect, in the case of a distribution belonging to the bilateral, multiple, diffuse, or hematogenous categories, similar medical images are displayed at the initial display size, whereas in the case of a distribution belonging to the segmental or bronchial categories, similar medical images are displayed zoomed, and in the case of a distribution belonging to the subpleural category, similar medical images are displayed zoomed in a state of including the pleura.

In the case of a distribution belonging to the bilateral, multiple, diffuse, or hematogenous categories, there is a high probability that the affected area has spread throughout the lungs or over a wide range of the lungs, and thus, from the medical standpoint, there is a need to display similar medical images at the initial display size, or in other words, without zooming.

On the other hand, in the case of a distribution belonging to the segmental or bronchial categories, the probability of the above is low. For this reason, by displaying similar medical images zoomed as a result of selecting a distribution belonging to the segmental or bronchial categories, the step of zooming the display may be skipped, thereby avoiding a lapse in the physician's concentration. Also, in the case of a distribution belonging to the subpleural category, the positional relationship between the pleura and the affected area becomes an important indicator for diagnosis, and thus, from the medical standpoint, there is a need to display similar medical images zoomed in a state of including the pleura.

Another aspect of the present disclosure is a control method for an apparatus including a processor to execute a process, the process including: receiving a plurality of thumbnail images respectively corresponding to a plurality of medical images, each of the medical images being similar to a target medical image to be interpreted, and the plurality of thumbnail images including a first thumbnail image and a second thumbnail image; before the processor receives a first instruction, displaying a target thumbnail image corresponding to the target medical image in a first display area, and displaying the plurality of thumbnail images in a second display area, the first thumbnail image and the second thumbnail being displayed adjacent to each other in the second display area, the first display area and the second display area being not overlapped, the first instruction is to drag the target medical image and overlap the target medical image with the first thumbnail image and the second thumbnail at a same time by using an input device; and after the processor receives the first instruction, displaying the target thumbnail image adjacent to the first thumbnail image in the second display area, and also displaying the target thumbnail image adjacent to the second thumbnail image in the second display area and still displaying the target thumbnail image in the first display area.

Embodiment

Hereinafter, an embodiment of the present disclosure will be described with reference to the drawings. Note that in the drawings, like signs are used to denote like structural elements.

(Overall Configuration)

FIG. 1 is an overall configuration diagram of a hospital information system to which an information terminal according to the present embodiment has been applied. As illustrated in FIG. 1, the hospital information system is equipped with an information terminal 100, a medical information management system 200, and a case search system 300.

The information terminal 100, the medical information management system 200, and the case search system 300 are communicably interconnected over a network 400.

Note that the medical information management system 200 and the case search system 300 are not necessarily required to be installed in a hospital, and may also be software running on hardware such as a data center, a private cloud server, or a public cloud server outside the hospital. In the case in which the medical information management system 200 and the case search system 300 are installed inside the hospital, a local area network may be adopted as the network 400. For the local network, an IEEE 802.3 series wired LAN, an IEEE 802.11 series wireless LAN, or a network combining both may be adopted. In the case in which the medical information management system 200 and the case search system 300 are realized using a server outside the hospital, the Internet may be adopted as the network 400.

For the information terminal 100, an information terminal such as a personal computer or a tablet is adopted, for example. For the medical information management system 200, a system such as a picture archiving and communication system (PACS) or an electronic health record system is adopted, for example.

(Information Terminal 100)

Figure 2:
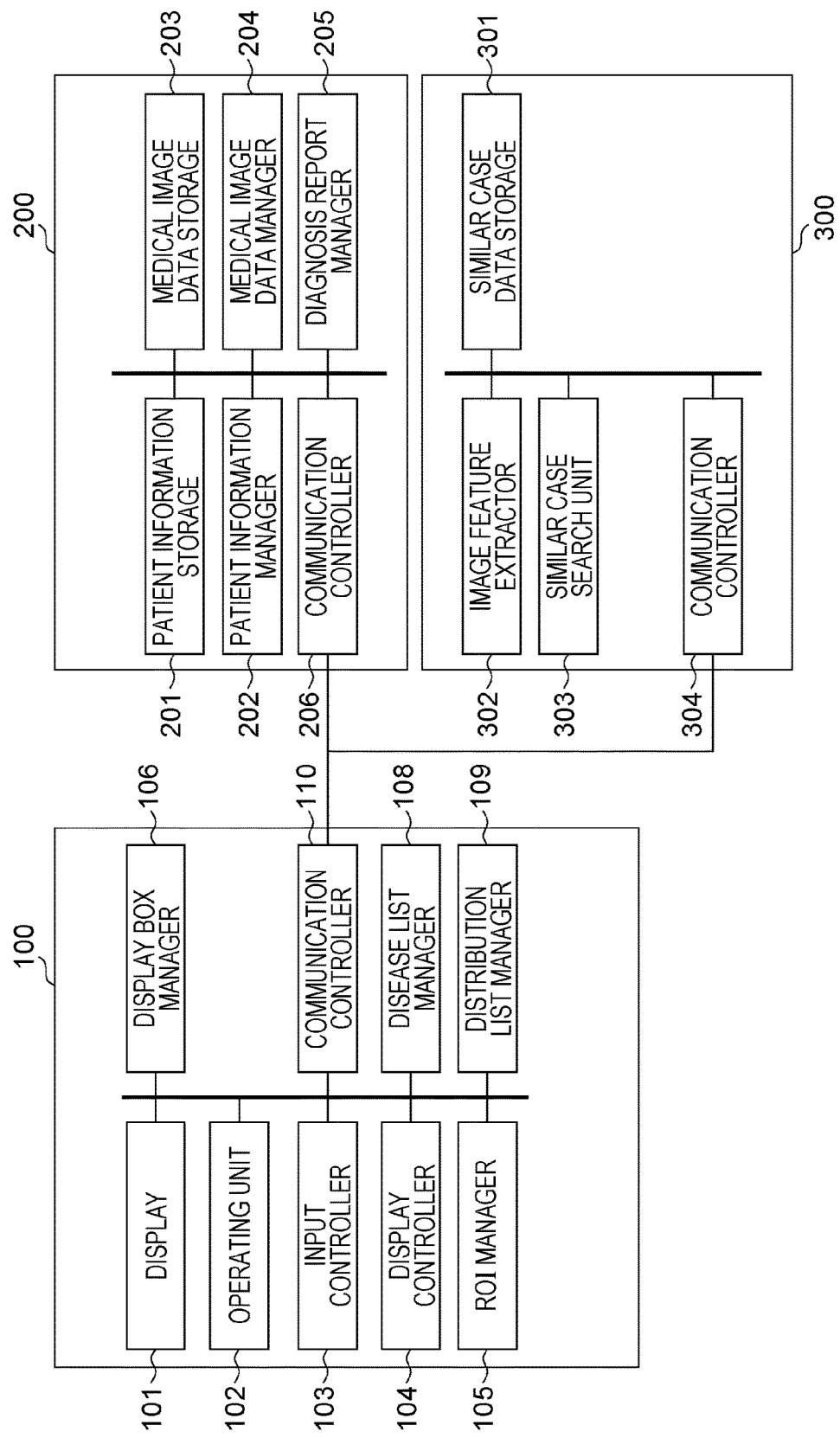
FIG. 2 is a block diagram illustrating a configuration of a medical information management system and a case search system.

FIG. 2 is a block diagram illustrating a configuration of the information terminal 100, the medical information management system 200, and the case search system 300. As illustrated in FIG. 2, the information terminal 100 is equipped with a display 101, an operating unit 102, an input controller 103, a display controller 104, an ROI manager 105, a display box manager 106, a disease list manager 108, a distribution list manager 109, and a communication controller 110.

The display 101 is realized by an LCD monitor, for example, and displays medical images to be diagnosed and health record images, while also displaying information such as a report input image for entering a diagnosis result. Note that although at least one display 101 is required, ordinarily two or three displays 101 are used for image diagnosis. In the present embodiment, two displays 101 are used, in which one display 101 is designated the display 101a, and the other display 101 is designated the display 101b (see FIG. 3).

Figure 3:
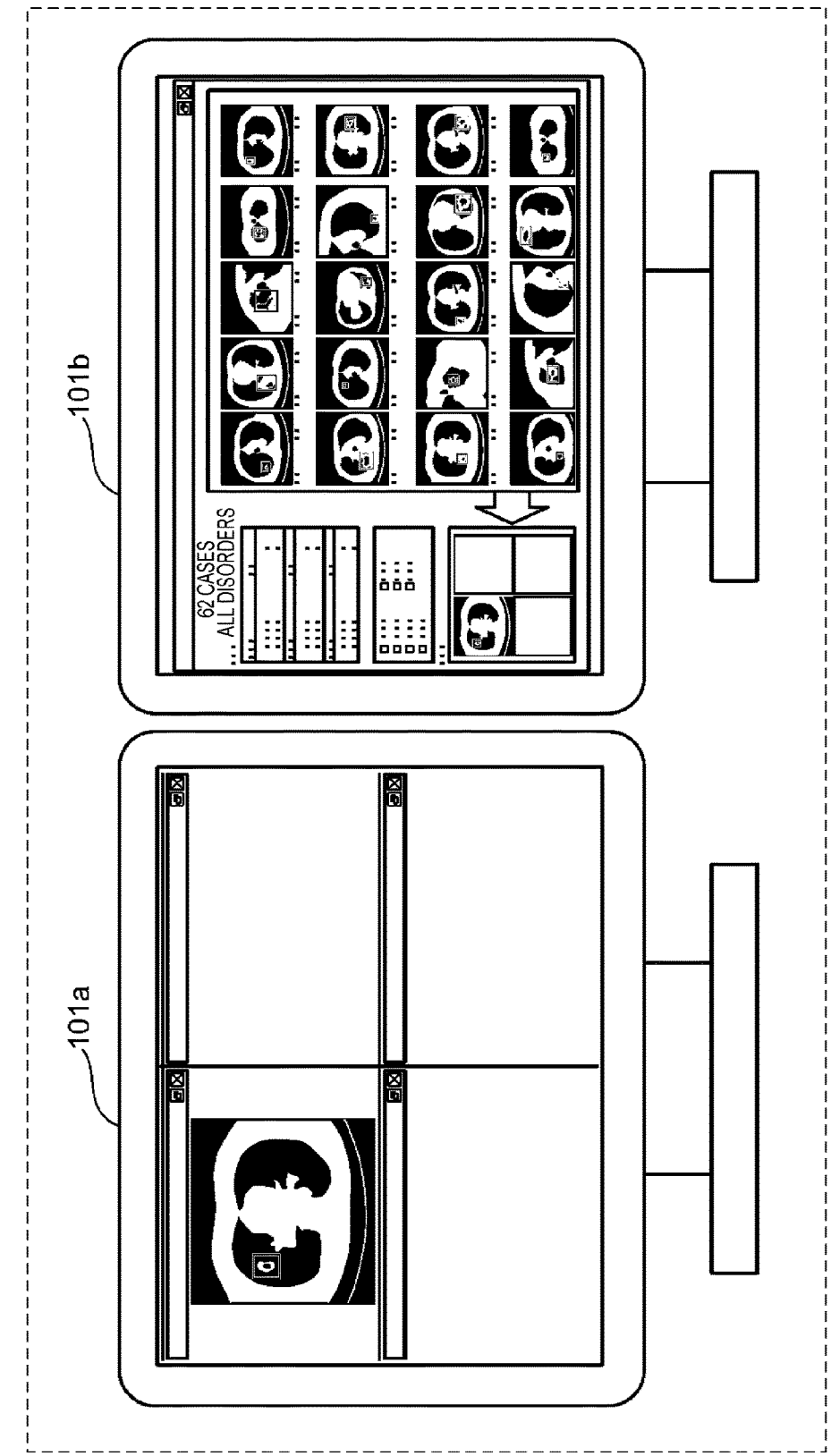
FIG. 3 is an exterior view of two displays.

FIG. 3 is an exterior view of the two displays 101a and 101b. In FIG. 3, on the display 101a, four medical image viewers are displayed in a 2×2 grid, while on the display 101b, the screen of the case search system 300 is displayed. Note that in the case of using a single display 101, two display screens are displayed in split areas on the display screen of the single display 101.

The operating unit 102 includes a keyboard and a mouse, for example, and accepts various operations input into the information terminal 100 by the user. For example, the operating unit 102 accepts operations such as user operations on medical images and health record images displayed on the display 101, and operations of inputting a diagnosis result into a report input screen.

The input controller 103, after sensing a user operation performed on the operating unit 102, interprets the content of the operation, and notifies other structural elements of the operation content. For example, the input controller 103 senses the position of a mouse pointer on the display 101 from coordinate data output from a mouse being used as the operating unit 102, and causes the mouse pointer to be displayed on the display 101. Additionally, if a graphical user interface (GUI) element (for example, a GUI button) generated by the display controller 104 is being displayed at the display position of the mouse pointer when the input controller 103 senses that the mouse has been clicked, the input controller 103 determines that the user has selected that GUI element, and notifies other structural elements that the relevant GUI element has been selected by the user.

The display controller 104 generates the GUI of the information terminal 100, and displays the GUI on the display 101.

When a similar case search is performed, the ROI manager 105 generates, and stores in memory, region of interest information indicating a region of interest (ROI) set with respect to a search query image discussed later, and manages the region of interest information.

The display box manager 106 stores display box management information 4410 (see FIG. 36) discussed later in memory, and manages the display box management information 4410.

Figure 6:
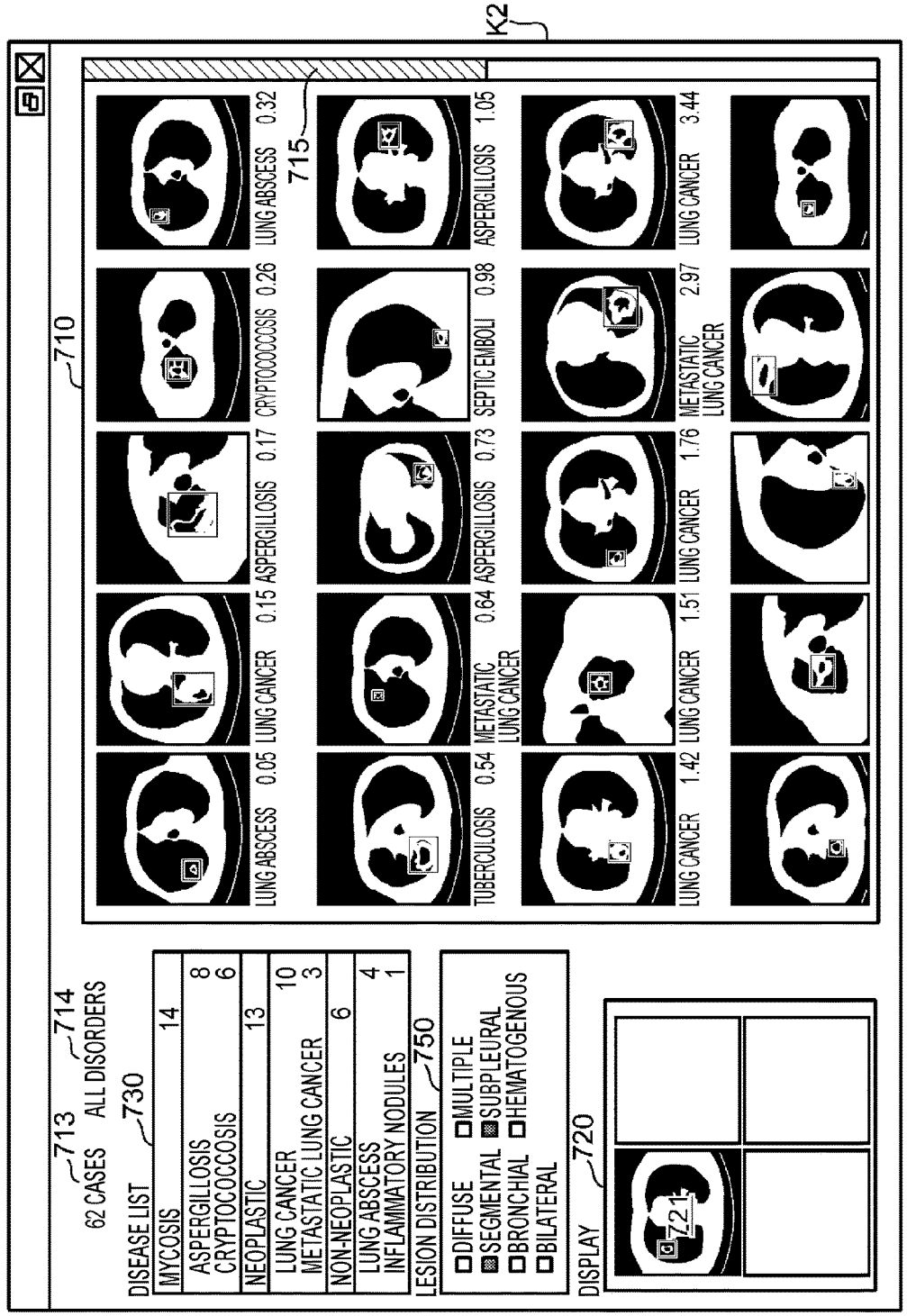
FIG. 6 is a diagram illustrating an example of a basic screen displayed on a display immediately after launching a similar case search application on an information terminal.

The disease list manager 108 generates, and stores in memory, a disease list (see FIG. 14) of similar cases displayed in a case display area 710 (see FIG. 6).

The distribution list manager 109 generates, and stores in memory, a distribution list (see FIG. 17) indicating lesion distributions of similar cases displayed in the case display area 710, and manages the distribution list.

The communication controller 110 includes a communication device for connecting the information terminal 100 to the network 400, for example, and controls communication between the information terminal 100 and the medical information management system 200, and between the information terminal 100 and the case search system 300. Additionally, the communication controller 110 accepts requests for the transmission of various data from other blocks, and transmits to the medical information management system 200 or the case search system 300, while in addition, receives data transmitted from the medical information management system 200 or the case search system 300, and passes the data to relevant blocks.

(Medical Information Management System 200)

As illustrated in FIG. 2, the medical information management system 200 is equipped with patient information storage 201, a patient information manager 202, medical image data storage 203, a medical image data manager 204, a diagnosis report manager 205, and a communication controller 206.

The patient information storage 201 stores patient information 1000 (see FIG. 24), in which is registered personal information such as the sex and age of the patient, clinical information such as a medical history, and examination information such as a blood test.

The patient information manager 202 executes processes on the patient information (see FIG. 24) stored in the patient information storage 201, such as a process of registering data input by the user and updating the patient information 1000 and a process of outputting the patient information 1000 to the display controller 104, and manages the patient information 1000. The medical image data storage 203 stores medical image data, which are images from patient examinations.

The medical image data manager 204 stores medical image data in the medical image data storage 203, and manages the medical image data.

The diagnosis report manager 205 manages a diagnosis report 3000 (see FIG. 27) indicating a diagnosis result made by a physician for an examination performed on a patient.

The communication controller 206 includes a communication device for connecting the medical information management system 200 to the network 400, for example, accepts requests for the transmission of various data from other blocks, and transmits to the information terminal 100 or the case search system 300, while in addition, receives data transmitted from the information terminal 100 or the case search system 300, and passes the data to relevant blocks.

(Case Search System 300)

As illustrated in FIG. 2, the case search system 300 is equipped with similar case data storage 301, an image feature extractor 302, a similar case search unit 303, and a communication controller 304.

The similar case data storage 301 stores similar case data 4000 (see FIG. 28), in which is registered in advance image features extracted from a large number of similar cases selected as the target data of a similar case search from among similar cases managed by the medical information management system 200, and generated thumbnail images.

The image feature extractor 302 extracts image features in region of interest information in a search query image transmitted from the communication controller 110 of the information terminal 100. Note that the region of interest information is an example of designation information indicating a region of interest.

The similar case search unit 303 generates similar case search results by respectively comparing the image features extracted by the image feature extractor 302 to the image features of one or more similar cases stored in the similar case data storage 301.

The communication controller 304 includes a communication device that connects the case search system 300 to the network 400, for example. The communication controller 304 accepts requests for the transmission of various data from other blocks, and transmits the various data to the information terminal 100 or the medical information management system 200, while in addition, receives data transmitted from the information terminal 100 or the medical information management system 200, and passes the data to relevant blocks.

(Implementation)

Figure 4:
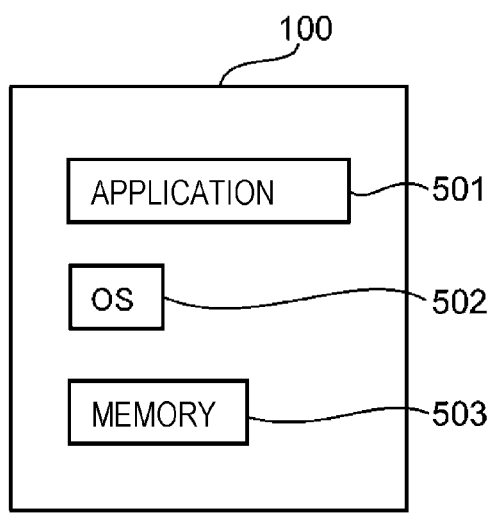
FIG. 4 is a diagram illustrating an example configuration of an implementation of an information terminal.

FIG. 4 is a diagram illustrating an example configuration of an implementation of the information terminal 100. As illustrated in FIG. 4, the information terminal 100 is equipped with an application 501, an operating system (OS) 502, memory 503, and other hardware not illustrated.

The application 501 is application software causing, for example, a personal computer or a tablet to function as the information terminal 100, and is executed by a processor of the information terminal 100. The information terminal 100 may implement the application 501 by reading out the application 501 from a computer-readable recording medium, or implement the application 501 by downloading the application 501 from a network.

Herein, the application 501 includes a medical information management application and a similar case search application. The medical information management application is an application for linking the information terminal 100 to the medical information management system 200, while the similar case search application is an application for linking the information terminal 100 to the case search system 300. Additionally, both applications exchange data with each other, and on the information terminal 100, unify the services provided by the medical information management system 200 and the case search system 300.

The OS 502 is the basic software of the information terminal 100, and is executed by a processor of the information terminal 100. The memory 503 is realized by memory devices such as RAM and ROM provided in the information terminal 100, and stores groups of data included in the application 501.

By having a processor of the information terminal 100 execute the application 501, the functions of the input controller 103, the display controller 104, the ROI manager 105, the display box manager 106, the disease list manager 108, the distribution list manager 109, and the communication controller 110 illustrated in FIG. 2 are realized.

However, in the present embodiment, the information terminal 100 may be implemented by the application 501 alone, implemented by the application 501 and the OS 502, implemented by the application 501, the OS 502, and the memory 503, or implemented by the application 501, the OS 502, the memory 503, and other hardware not illustrated. The realization of the information terminal 100 according to the present embodiment is possible with any of the above implementations.

(Interpretation Flow to Display Screen)

Figure 5:
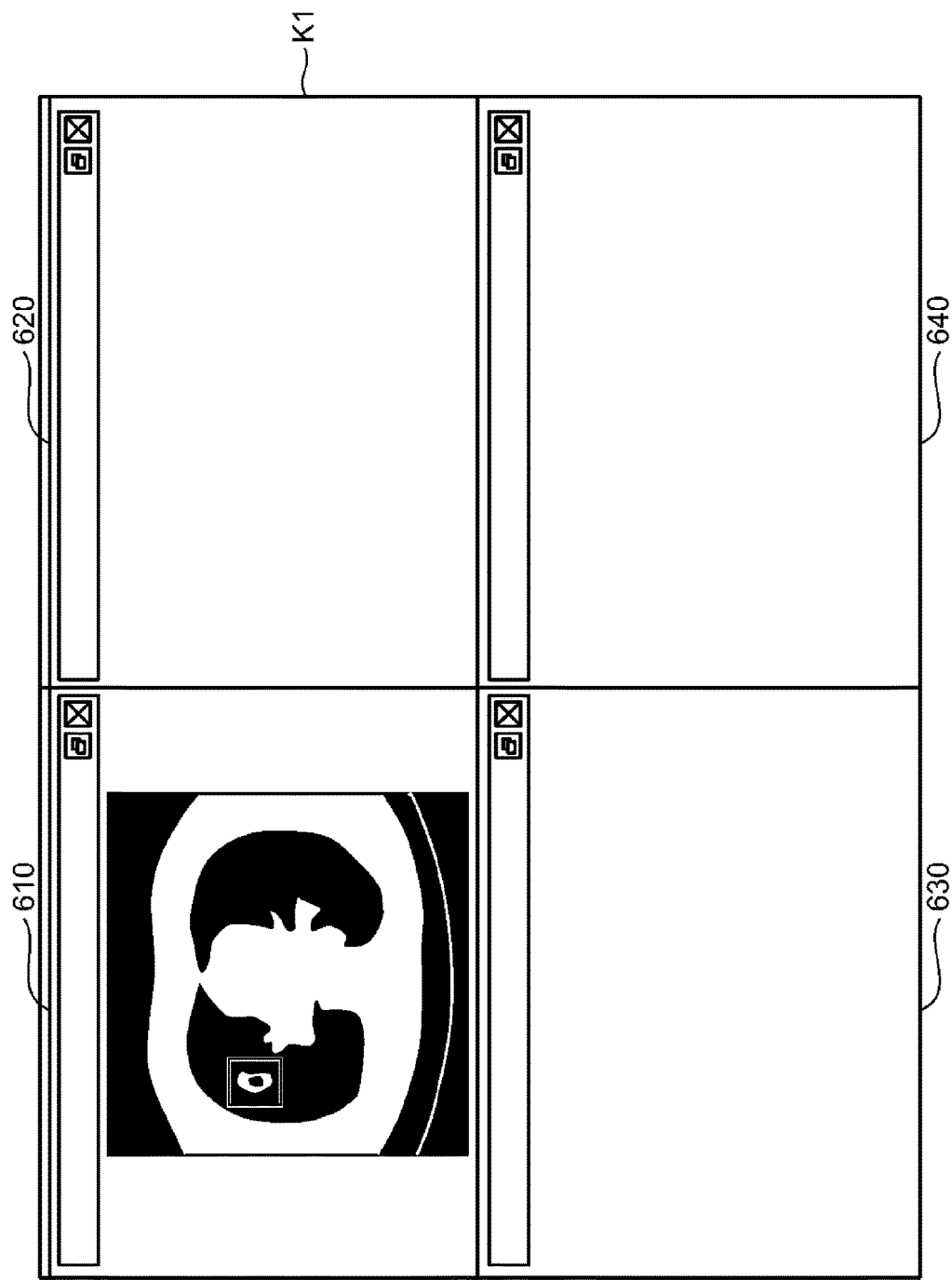
FIG. 5 is a diagram illustrating an example of a basic screen displayed on a display immediately after launching a similar case search application on an information terminal.

FIG. 5 is a diagram illustrating an example of a basic screen K1 displayed on the display 101a immediately after launching the similar case search application on the information terminal 100. The basic screen K1 illustrated in FIG. 5 is made up of four medical image viewers 610 to 640. Ordinarily, medical images are recorded in Digital Imaging and Communication in Medicine (DICOM) format, and the medical image viewers 610 to 640 are viewers that handle DICOM. The medical images handled in the present embodiment are taken to be chest CT images made up of a large number of tomographic images (hereinafter called slice images) in DICOM format. However, this is merely one example, and CT images of other parts (such as the head, abdomen, legs, or arms, for example) may also be adopted.

In the chest CT images displayed on the medical image viewers 610 to 640, slice images may be changed with a mouse or keyboard operation, for example. Herein, the slice images constituting a chest CT image are arranged in order proceeding from the neck to the abdomen.

For example, if the mouse pointer is positioned over the medical image viewer 610, and a rotation of the mouse wheel is sensed by the input controller 103, the display controller 104 changes the slice image being displayed in the medical image viewer 610 according to the sensed amount of rotation. At this point, if the mouse wheel is rotated one click downward, the slice image currently being displayed in the medical image viewer 610 is changed to the slice image in the next slice position, for example. On the other hand, if the mouse wheel is rotated one click upward, the slice image currently being displayed in the medical image viewer 610 is changed to the slice image in the previous slice position, for example. Thus, a user such as a physician searches for a desired slice image while rotating the mouse wheel upward or downward to change the slice image displayed in the medical image viewer 610 as appropriate.

Note that instead of adopting chest CT images as the medical images, magnetic resonance imaging (MRI) images or plain X-ray images may also be adopted. Also, although the number of medical image viewers is 4 in the example of FIG. 5, this is merely one example, and another number, such as 6 or 8, for example, may also be adopted. As the number of medical image viewers increases, the number of images that may be compared simultaneously increases, but the display area per image also becomes smaller. For this reason, a configuration allowing the number of medical image viewers to be changed appropriately according to the display size of the display 101a may be adopted. Herein, the number of medical image viewers is taken to be freely modifiable by a user or an administrator.

Before the similar case search application is launched, a slice image of a chest CT image of a certain patient is displayed over the entirety of the display 101a. Subsequently, in this state, if the similar case search application is launched by a user such as a radiological interpreter, the slice image that was being displayed over the entirety of the display 101a is displayed in the medical image viewer 610.

In other words, when the user launches the similar case search application, the search query image that was being displayed over the entirety of the display 101a is displayed initially in the medical image viewer 610. Note that the display controller 104 may also display the region of interest (ROI) of the target of the similar case search as an overlay on top of the search query image. The search query image is an example of a medical image to be interpreted.

In FIG. 5, no images are being displayed in the other medical image viewers 620 to 640, but if there are multiple images from a patient examination to be diagnosed, and the multiple examination images are being displayed on the display 101a before the similar case search application is launched, the display controller 104 may keep displaying these multiple examination images in the medical image viewers 620 to 640.

FIG. 6 is a diagram illustrating an example of a basic screen K2 displayed on the display 101b immediately after launching the similar case search application on the information terminal 100. The basic screen K2 illustrated in FIG. 6 includes a case display area 710, a layout area 720, a disease list display area 730, and a distribution list display area 750. Note that the layout area 720 is an example of a first display area, while the case display area 710 is an example of a second display area.

The case display area 710 is a rectangular area in which thumbnail images of similar cases that resemble the search query image are displayed in order of similarity. Herein, the thumbnail images of similar cases are an example of similar medical images.

Since a large number of similar cases are displayed in the case display area 710, converting the resolutions and pixel values on the spot would be a time-consuming process. Thus, thumbnail images are created in advance from the original slice images, and saved in the case search system 300.

Hereinafter, resolution and pixel value conversion will be elaborated further. The resolution of an original slice image is 512×512 pixels, but since a thumbnail image is of lower resolution, it is necessary to perform resolution conversion.

Accordingly, the thumbnail image is generated by performing a downscaling process and a tone conversion process on the original slice image.

The tone conversion process is performed as follows, for example. In a slice image acquired by CT, each pixel value (CT value) takes one of 2000 possible tone value from −1000 to +1000 Hounsfield units (HU), which cannot be displayed directly on an ordinary display with 8-bit tone depth. Additionally, even if such an image can be displayed, from among the 2000 tones, it is difficult for the human eye to distinguish between the emphysema region (CT value: −1000 HU), normal tissue of the lung field (CT value: approximately −900 HU), the ground-glass region (CT value: −800 HU), soft tissue (CT value: −100 to −50 HU), water (CT value: 0 HU), and bone (CT value: 1000 HU).

Thus, ordinarily, a window level and a window width are set for each pixel value of a slice image, and the slice image is reorganized into 8-bit pixel values and displayed on the display. Herein, the window level indicates a CT value that serves as the center of the window, and the window width indicates the width above and below the window center.

For example, if a DICOM image is reconstructed under a lung field condition, the window level is set from −550 to −800, and the window width is set from 1000 to 1600. Consequently, a thumbnail image is also generated by dropping the pixel values to 8 bits from the original slice image according to the above process.

Note that the thumbnail images displayed in the case display area 710 are thumbnail images indicating similar cases for which the distance to a feature vector of the case to be diagnosed is less than or equal to a certain threshold value. Herein, Euclidean distance is used as the distance, for example. However, a difference measure of distance, such as city block distance, may also be adopted as the distance. Two images being compared are similar to the extent that the distance is short. In addition, a feature vector obtained from the original slice image and not from the thumbnail image is adopted.

Figure 7:
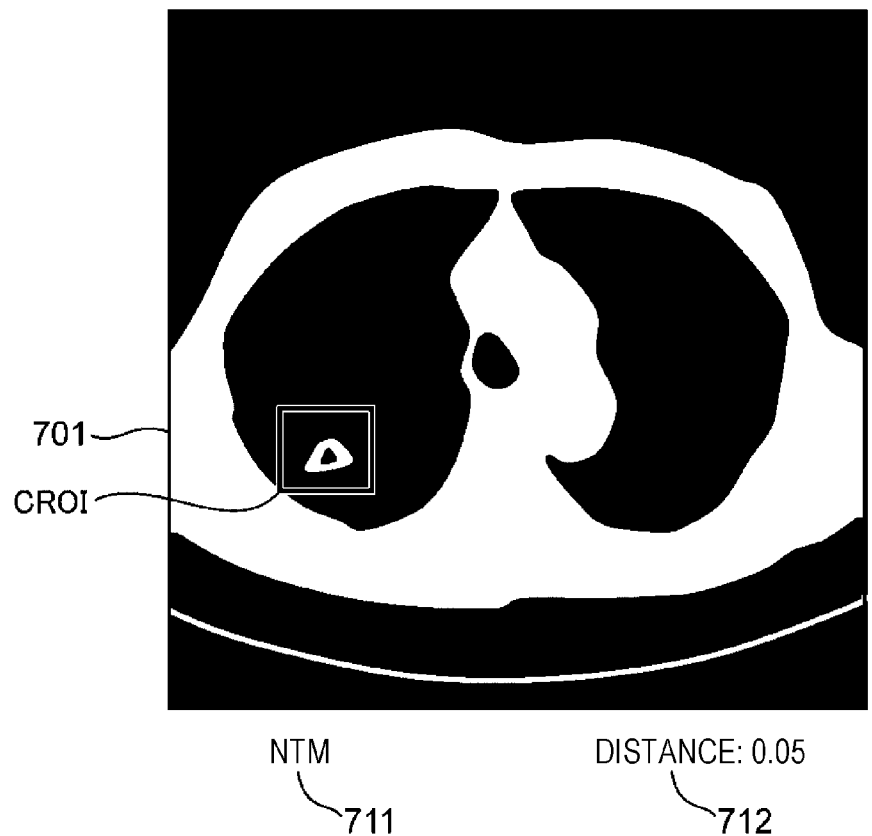
FIG. 7 is a diagram illustrating a display area of one similar case displayed in a case display area.

FIG. 7 is a diagram illustrating a display area 701 (an example of an individual area) of one similar case displayed in the case display area 710. In the display area 701 of the similar case, a thumbnail image is displayed, and below the thumbnail image, a definite diagnosis display area 711 and a distance display area 712 are arranged. In the definite diagnosis display area 711, the name of the disease according to the definite diagnosis of the corresponding similar case is displayed. The name of the disease according to the definite diagnosis refers to the name of the disease whose diagnosis was confirmed for the corresponding similar case. In the distance display area 712, the distance between the feature vector of the slice image of the corresponding similar case and the feature vector of the search query image is displayed. In the example of FIG. 7, "NTM" (nontuberculous mycobacterial infection) is displayed in the definite diagnosis display area 711, and thus the thumbnail image represents a thumbnail image of a similar case with a definite diagnosis of NTM. In addition, in the distance display area 712, "0.05" is displayed, thus indicating that the distance between the slice image of this similar case and the search query image is "0.05".

As illustrated in FIG. 7, the thumbnail image illustrated in the display area 701 of the similar case includes a corresponding region of interest CROI. The corresponding region of interest CROI is a region corresponding to the region of interest set in the search query image (the medical image to be interpreted). In other words, the corresponding region of interest CROI is a region resembling the region of interest.

Note that in the following, the corresponding region of interest may also be simply designated the "region of interest".

Returning to FIG. 6, a search hit display area 713 is disposed in the top-left of the basic screen K2, for example. In the search hit display area 713 is displayed the number of similar cases resembling the case to be diagnosed that were acquired from the case search system 300 as the results of the search process.

Note that if the number of similar cases is very large, it may not be possible to display all similar cases in the case display area 710 at once. Accordingly, a vertically elongated scrollbar 715 is provided on the right side of the case display area 710, for example. The display controller 104 scrolls the thumbnail images displayed in the case display area 710 up or down, according to the amount of movement of the scrollbar 715. Consequently, the user is able to make similar cases that were in a hidden state be displayed in the case display area 710, and observe those similar cases.

Note that the scrollbar 715 may also be horizontally elongated. In this case, the display controller 104 may scroll the thumbnail images displayed in the case display area 710 to the left or right, according to the amount of movement of the scrollbar 715. Alternatively, if a directional key on the keyboard is pressed while the mouse pointer is positioned in the case display area 710, the display controller 104 may scroll the thumbnail images displayed in the case display area 710 in the direction of the key being pressed, for as long as the key is pressed.

Note that the information terminal 100 is taken to acquire, from the case search system 300, thumbnail images for which the distance to the search query image is less than or equal to a certain threshold value, but this is merely one example. For example, the information terminal 100 may also acquire, from the case search system 300, a fixed number of thumbnail images in order of highest similarity. Alternatively, the information terminal 100 may acquire thumbnail images from the case search system 300 so that a fixed number of thumbnail images of certain diseases according to the definite diagnosis are included.

Note that the technique of displaying thumbnail images in the case display area 710 may adopt a display technique such as displaying the thumbnail image with the shortest distance to the search query image at the left edge of the topmost row, displaying thumbnail images so that the distance successively increases proceeding to the right, and when the right edge of the same row is reached, displaying the thumbnail image with the next-largest distance at the left edge of the second row from the top, for example. In other words, a display technique may be adopted in which thumbnail images are displayed in the case display area 710 in order of smallest distance starting from the top-left and proceeding to the bottom-right in a serpentine manner.

Obviously, the present embodiment may also adopt some other display technique. For example, the present embodiment may also adopt a display technique of displaying the thumbnail image with the shortest distance at the top edge of the first column from the left, displaying thumbnail images so that the distance successively increases proceeding down, and when the bottom edge of the same column is reached, displaying the thumbnail image with the next-largest distance at the top edge of the second column from the left, for example. Additionally, a configuration enabling the user to switch between these multiple display techniques may also be adopted.

Also, although distance is adopted as the similarity in the above example, any indicator of similarity may be adopted insofar as the indicator expresses the resemblance between images, such as cosine similarity. If cosine similarity is adopted, the resemblance between two compared images becomes higher as the value approaches 1.

Note that, although discussed in detail later, the similar cases displayed in the case display area 710 may be filtered by the diseases displayed in the disease list display area 730 or the lesion distributions displayed in the distribution list display area 750, for example. The currently set filter condition on the similar cases is displayed in a display condition display area 714. The example of FIG. 6 illustrates a state immediately after performing a similar case search with no filters applied, and thus "All Disorders" is displayed in the display condition display area 714.

The layout area 720 is disposed in the bottom-left of the basic screen K2 illustrated in FIG. 6, for example. The layout area 720 may be used to cause the medical image viewers of the display 101a to display images that the user wants to observe in detail from among the similar case thumbnail images displayed in the case display area 710. As illustrated in FIG. 5, the four medical image viewers 610 to 640 are displayed in a 2×2 grid on the display 101a. In addition, in the layout area 720, four display boxes in a 2×2 grid. In this way, the number and arrangement of the medical image viewers 610 to 640 displayed on the display 101 may match the number and arrangement of the display boxes in the layout area 720. As illustrated in FIG. 5, the search query image is being displayed in the medical image viewer 610, and correspondingly, a thumbnail image of the search query image is initially displayed in the display box 721.

(Operation of Inserting Search Query Image into Case Display Area 710)

The present embodiment is configured to enable the search query image to be inserted into the case display area 710 by an operation performed by the user (physician). If the search query image is inserted into the case display area 710, the thumbnail images of the similar cases being displayed in the case display area 710 move, and the search query image is displayed adjacent to the thumbnail images. Hereinafter, the operation of inserting the search query image into the case display area 710 will be described.

Figure 8:
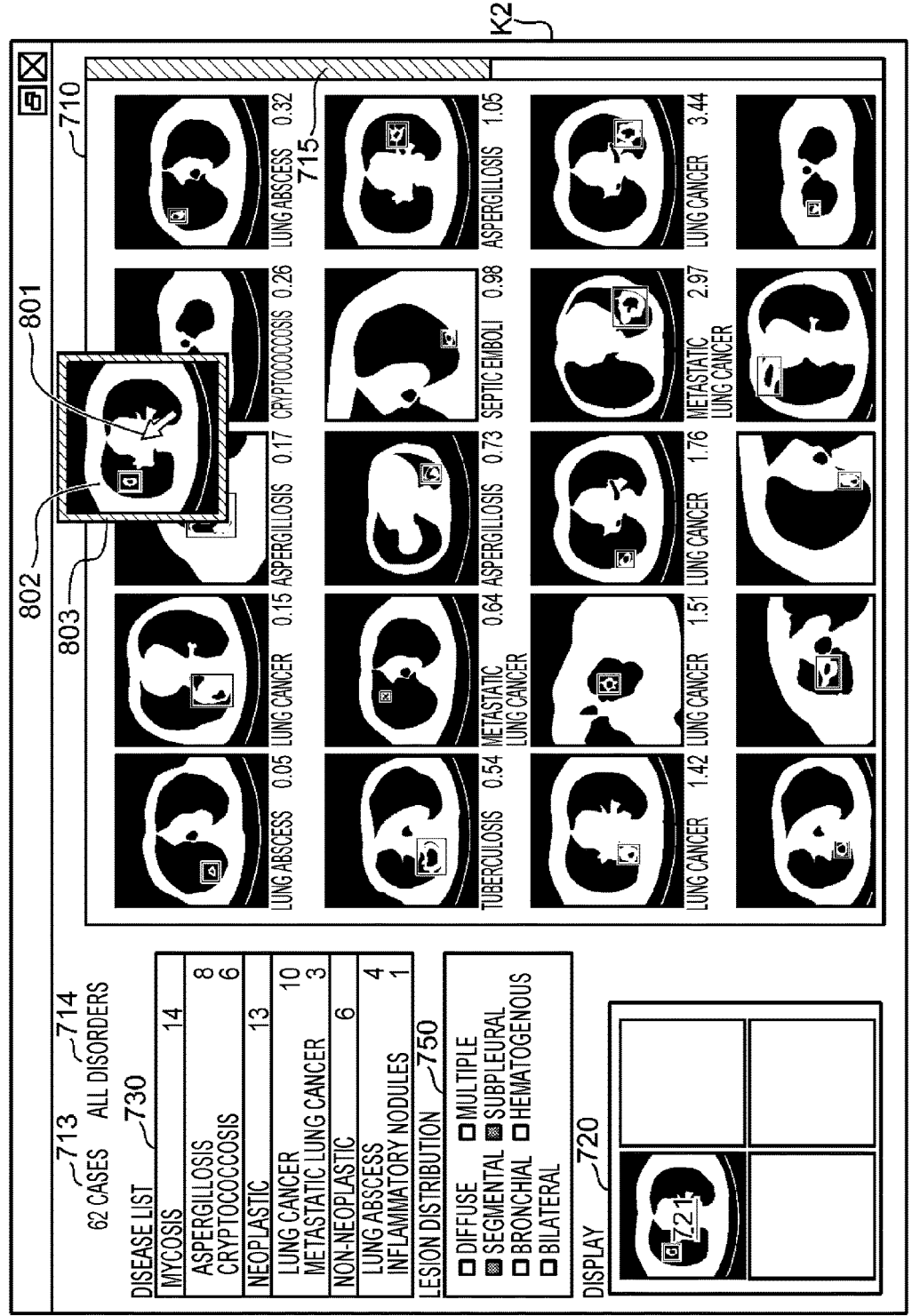
FIG. 8 is a diagram illustrating a basic screen before a search query image is inserted into a case display area.

FIG. 8 is a diagram illustrating the basic screen K2 before the search query image is inserted into the case display area 710. If the user drags the search query image being displayed in the layout area 720 with the mouse of the operating unit 102, the search query image 802 moves in conjunction with the position of the mouse pointer 801, and is displayed in the case display area 710. As illustrated in FIG. 8, when the search query image 802 is moving, the search query image is also displayed in the layout area 720. Note that when the search query image 802 is moving, the search query image may also not be displayed in the layout area 720.

As illustrated in FIGS. 6 and 8, in the state in which the basic screen K2 is displayed immediately after a similar case search, the entirety of a thumbnail image is displayed in each display area 701 (see FIG. 7). The case display area 710 includes a certain number ND (in this embodiment, ND=20) of display areas 701 (see FIG. 7), each of which displays a thumbnail image. In the case display area 710, the number NE of thumbnail images displayed horizontally (on one row, or in other words, the number of display areas 701 provided horizontally) is a predetermined, fixed value (in this embodiment, NE=5).

Figure 9:
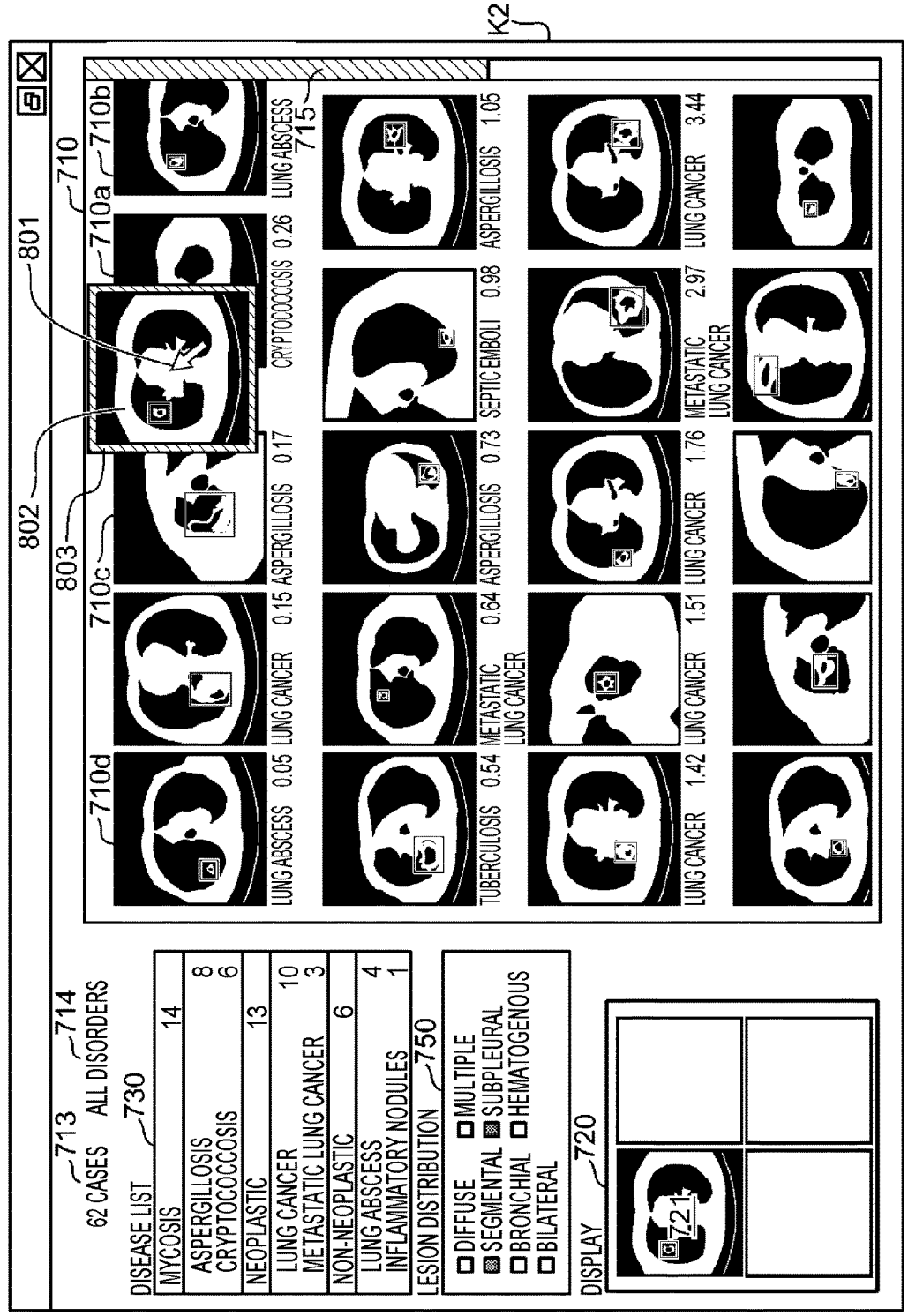
FIG. 9 is a diagram illustrating a movement state of thumbnail images displayed in a case display area when a search query image is inserted.

FIG. 9 is a diagram illustrating a movement state of thumbnail images displayed in the case display area 710 when the search query image is inserted. According to a drag operation performed by the user, the search query image 802 moves in conjunction with the position of the mouse pointer 801. In the present embodiment, the mouse pointer 801 moves over the thumbnail image 710a of the similar case that the user wants to move.

The input controller 103 senses that the position of the mouse pointer 801 has stopped for a certain amount of time or more inside a certain area including the thumbnail image 710a. Subsequently, as illustrated in FIG. 9, from among the thumbnail images of similar cases displayed in the case display area 710, the display controller 104 moves the thumbnail image 710a of the similar case that the user wants to move, as well as all thumbnail images on the same row being displayed to the right of the thumbnail image 710a (in FIG. 9, the thumbnail image 710b), to the right.

Note that the certain area including the thumbnail image 710a may be the display area 701 (see FIG. 7) in which the thumbnail image 710a is displayed. Alternatively, the certain area including the thumbnail image 710a may be an area larger than the display area 701, but not large enough to overlap with adjacent areas.

When the user wants to place the search query image 802 on the left side of the thumbnail image 710a and compare the thumbnail image 710a and the search query image 802, or when the user wants to place the search query image 802 on the right side of the thumbnail image 710c and compare the thumbnail image 710c and the search query image 802, the user decides that the thumbnail image 710a is the thumbnail image to be moved. In this way, in the present embodiment, when inserting the search query image 802 into the case display area 710, the display controller 104 moves the displayed thumbnail images of similar cases to the right.

Figure 10:
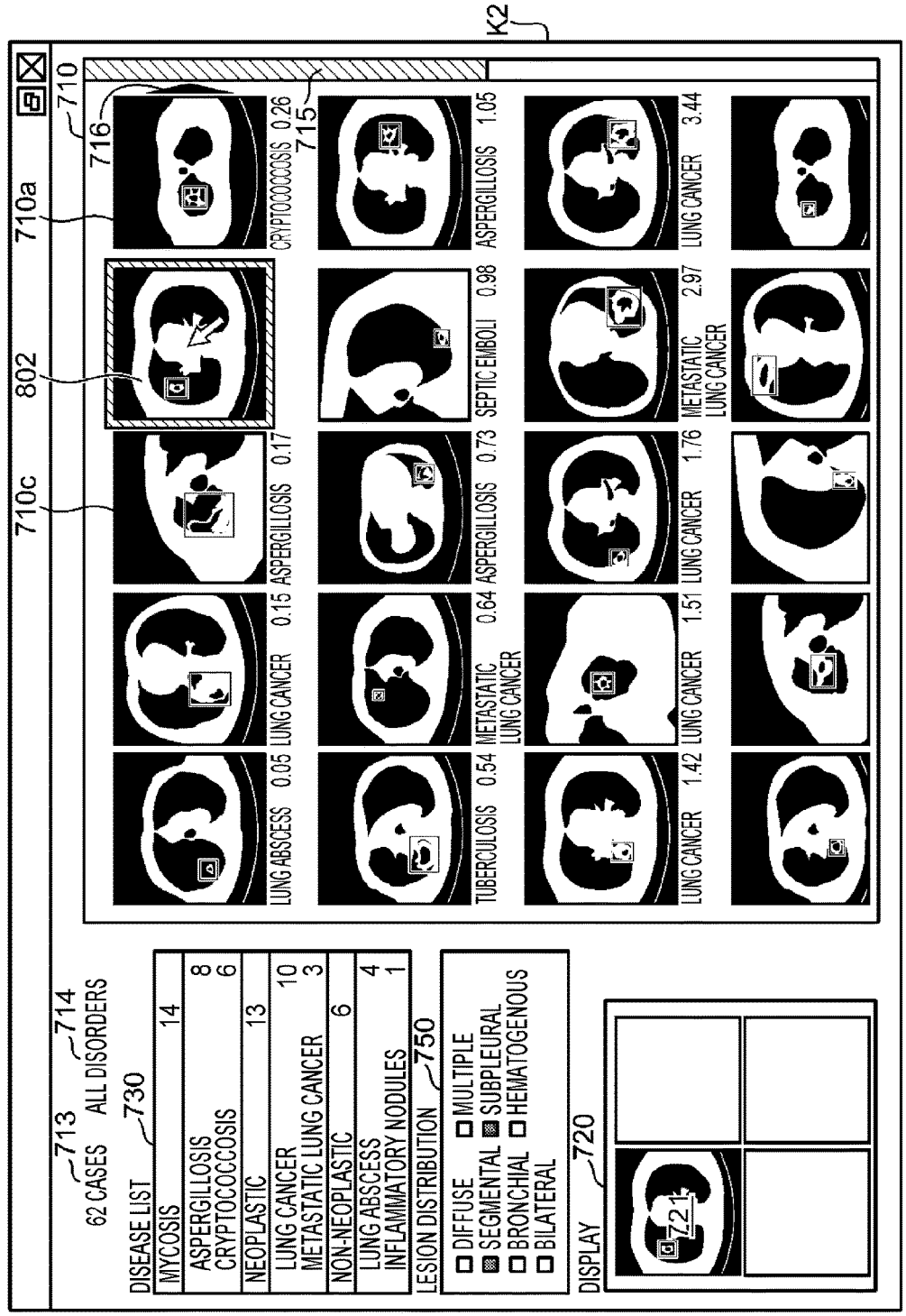
FIG. 10 is a diagram illustrating a state in which a search query image is inserted into a case display area.

FIG. 10 is a diagram illustrating a state in which the search query image 802 is inserted into the case display area 710. As illustrated in FIG. 10, the display controller 104 moves the thumbnail image 710a and the thumbnail image 710b adjacent to the right of the thumbnail image 710a by the space of one thumbnail image to the right. With this operation, the display controller 104 displays the search query image 802 at the position where the thumbnail image 710a was being displayed originally. As a result, the thumbnail image 710b that was being displayed adjacent to the right edge of the case display area 710 in FIG. 8 (an example of a third similar medical image) is not displayed in FIG. 10.

In this way, the display controller 104 reliably displays the search query image 802 (an example of a target medical image) adjacent to the thumbnail image 710a (an example of a second similar medical image) or the thumbnail image 710c (an example of a first similar medical image) for comparison. With this function, other thumbnail images do not exist between the search query image 802 and the thumbnail image 710a or 710c for comparison. As a result, when performing the comparison work, the movement of the physician's gaze is decreased. For this reason, the physical burden associated with shifting one's gaze back and forth when making a detailed comparison of many characteristics such as the position, size, shape, and distribution of shadows may be reduced, leading to improved diagnosis accuracy. Note that in FIG. 10, the search query image 802 is displayed between the thumbnail image 710a and the thumbnail image 710c. The search query image 802 is not limited to being displayed between the thumbnail image 710a and the thumbnail image 710c, and the movement of the physician's gaze may be decreased similarly even if the search query image 802 is displayed adjacently above or below the thumbnail image 710a and the thumbnail image 710c.

As illustrated in FIGS. 8 to 10, when displaying the search query image 802 in the case display area 710, the display controller 104 encloses the search query image 802 with a thick frame 803 to emphasize the search query image 802 compared to the thumbnail images of similar cases. Note that the method of emphasis is not limited to the thick frame 803, and a frame of a different color may also be displayed, or text may be displayed near the search query image 802.

With this function, the user easily is able to grasp the position of the search query image 802 inserted into the case display area 710. For this reason, the movement of the physician's gaze to compare the search query image in the layout area 720 and the medical images in the case display area 710 in order to confirm the position of the search query image 802 may be decreased. As a result, gaze movement may be conducted to make a detailed comparison of many characteristics such as the position, size, shape, and distribution of shadows. Consequently, the physical burden on the user is reduced, leading to improved diagnosis accuracy.

As illustrated in FIGS. 9 and 10, the display controller 104 makes the size of the search query image 802 to insert the same as the size of the thumbnail images being displayed in the case display area 710. With this function, the amount of movement of the thumbnail images is fixed to the space of one thumbnail image, irrespective of the position in the case display area 710 where the search query image 802 is inserted. For this reason, even when multiple thumbnail images are moved, the user becomes able to grasp easily the difference in the positional relationships of the thumbnail images before and after insertion.

As described with reference to FIG. 6, in the present embodiment, the technique of displaying thumbnail images in the case display area 710 adopts a display technique of displaying the thumbnail image with the shortest distance to the search query image at the left edge of the uppermost row, displaying thumbnail images so that the distance successively increases proceeding to the right, and when the right edge of the same row is reached, displaying the thumbnail image with the next-largest distance at the left edge of the second row from the top.

In this case, it is also conceivable to keep displaying all thumbnail images in the case display area 710, and maintain the order by distance. To achieve the above, when the search query image is inserted on the first row, for example, the thumbnail image on the right edge of the first row is moved to the left edge of the second row. Subsequently, in conjunction with the above movement, the thumbnail images of similar cases having a greater distance than the thumbnail image at the position where the search query image is inserted are all moved. Consequently, the layout of thumbnail images changes greatly compared to before the insertion of the search query image, and the user is no longer able to grasp easily the positional relationships of the thumbnail images before and after insertion. For this reason, in the present embodiment, the positions of thumbnail images are not moved across rows.

In other words, the display controller 104 moves the thumbnail image that was being displayed on the right edge of the row where the search query image 802 is inserted (in FIGS. 8 and 9, the thumbnail image 710*b*) outside the case display area 710, as illustrated in FIG. 9. Additionally, when the insertion of the search query image 802 is completed, the display controller 104 does not display the thumbnail image 710*b* in the case display area 710, as illustrated in FIG. 10. Consequently, the positional relationships of thumbnail images on rows other than the row where the search query image 802 is inserted are maintained.

With this function, the user becomes able to grasp easily the positional relationships of thumbnail images before and after the insertion of the search query image. As a result, gaze movement may be conducted to make a detailed comparison of many characteristics such as the position, size, shape, and distribution of shadows. Consequently, the physical burden on the user is reduced, leading to improved diagnosis accuracy.

As illustrated in FIGS. 9 and 10, when the thumbnail image that was being displayed on the right edge of the row where the search query image 802 is inserted is not displayed in the case display area 710, the similar case having the next-highest similarity after the similar case that the physician wants to compare may be hidden outside the case display area 710. For example, if the physician wants to compare the search query image 802 and the thumbnail image 710*a*, the thumbnail image 710*b* with the next-shortest distance to the search query image 802 after the thumbnail image 710*a* is not displayed in the case display area 710.

For this reason, in the present embodiment, the display controller 104 displays a scroll button 716 inside the case display area 710 on the right edge of the row where the search query image 802 is inserted, as illustrated in FIG. 10. The scroll button 716 indicates that a thumbnail image not being displayed exists. If the user left-clicks the scroll button 716 with the mouse, for example, the input controller 103 senses this operation. Subsequently, the display controller 104 scrolls the search query image 802 and the thumbnail images on the row where the search query image 802 is inserted.

Figure 11:
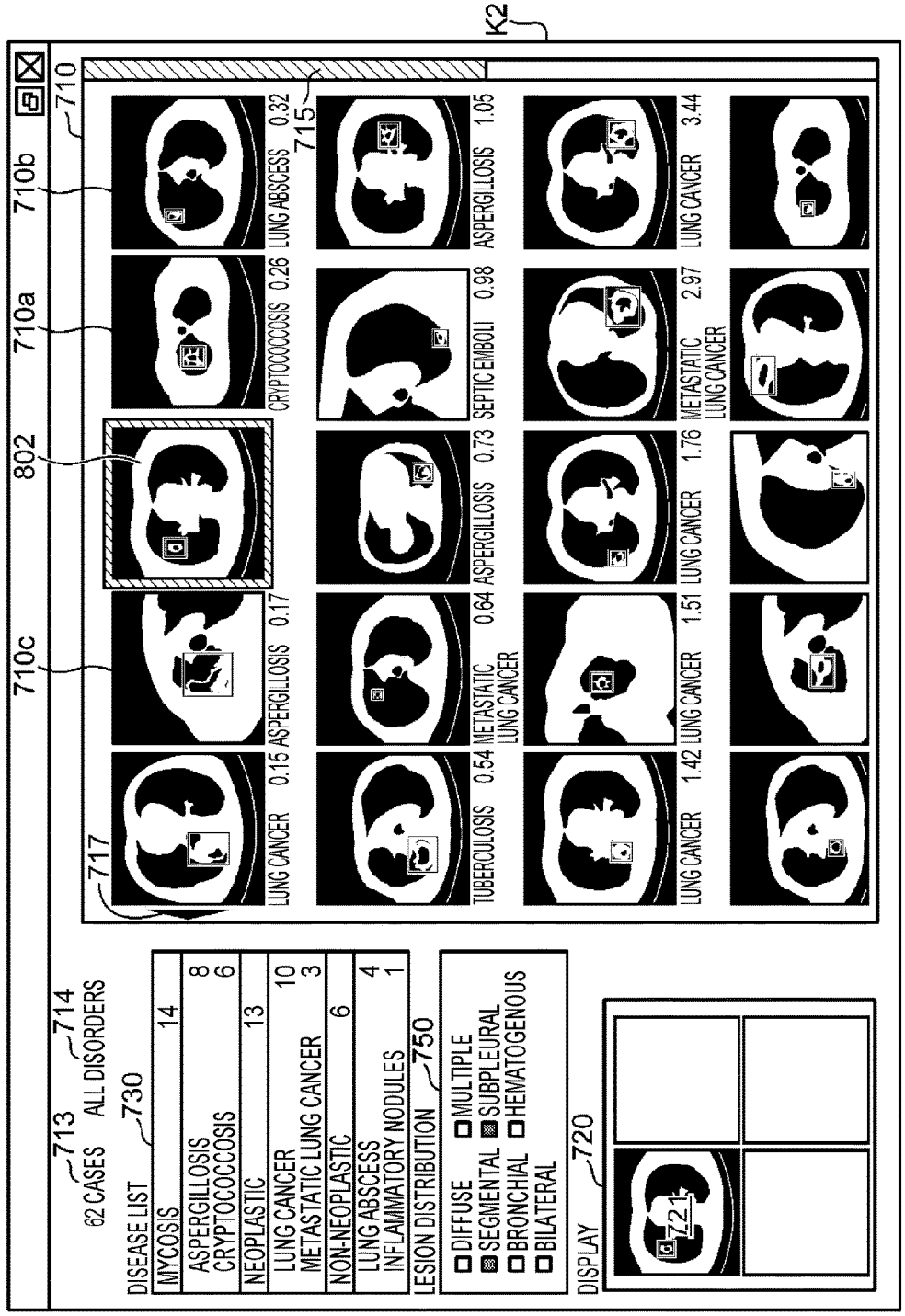
FIG. 11 is a diagram illustrating a state in which the scroll button in FIG. 10 is operated, and a search query image and thumbnail images on the row where the search query image is inserted are scrolled.

FIG. 11 is a diagram illustrating a state in which the scroll button 716 in FIG. 10 is operated, and the search query image 802 and the thumbnail images on the row where the search query image 802 is inserted are scrolled.

As illustrated in FIG. 11, the thumbnail image 710*b* that was no longer displayed in FIG. 10 is displayed in the case display area 710. With this function, it is possible to compare the search query image 802 to the thumbnail image 710*b* having the next-highest similarity after the thumbnail image 710*a* after the insertion of the search query image 802, without moving the search query image 802 again. Note that in FIG. 11, to enable the display of the thumbnail image on the left edge of FIG. 10 that is no longer displayed, a scroll button 717 in the opposite direction of the scroll button 716 is displayed on the left edge of the case display area 710.

In the embodiment illustrated in FIGS. 8 to 11, when the similar case that the physician wants to compare to the search query image 802 is the thumbnail image 710*b* being displayed on the right edge of the case display area 710, if the search query image 802 is inserted at the position of the thumbnail image 710*b*, the thumbnail image 710*b* moves to the right, and is no longer displayed in the case display area 710. Consequently, to display the thumbnail image 710*b* in the case display area 710, it becomes necessary to operate the scroll button 716.

Accordingly, the display controller 104 may also be configured to be unable to insert the search query image 802 at the position of a thumbnail image being displayed on the right edge of the case display area 710.

Figure 12:
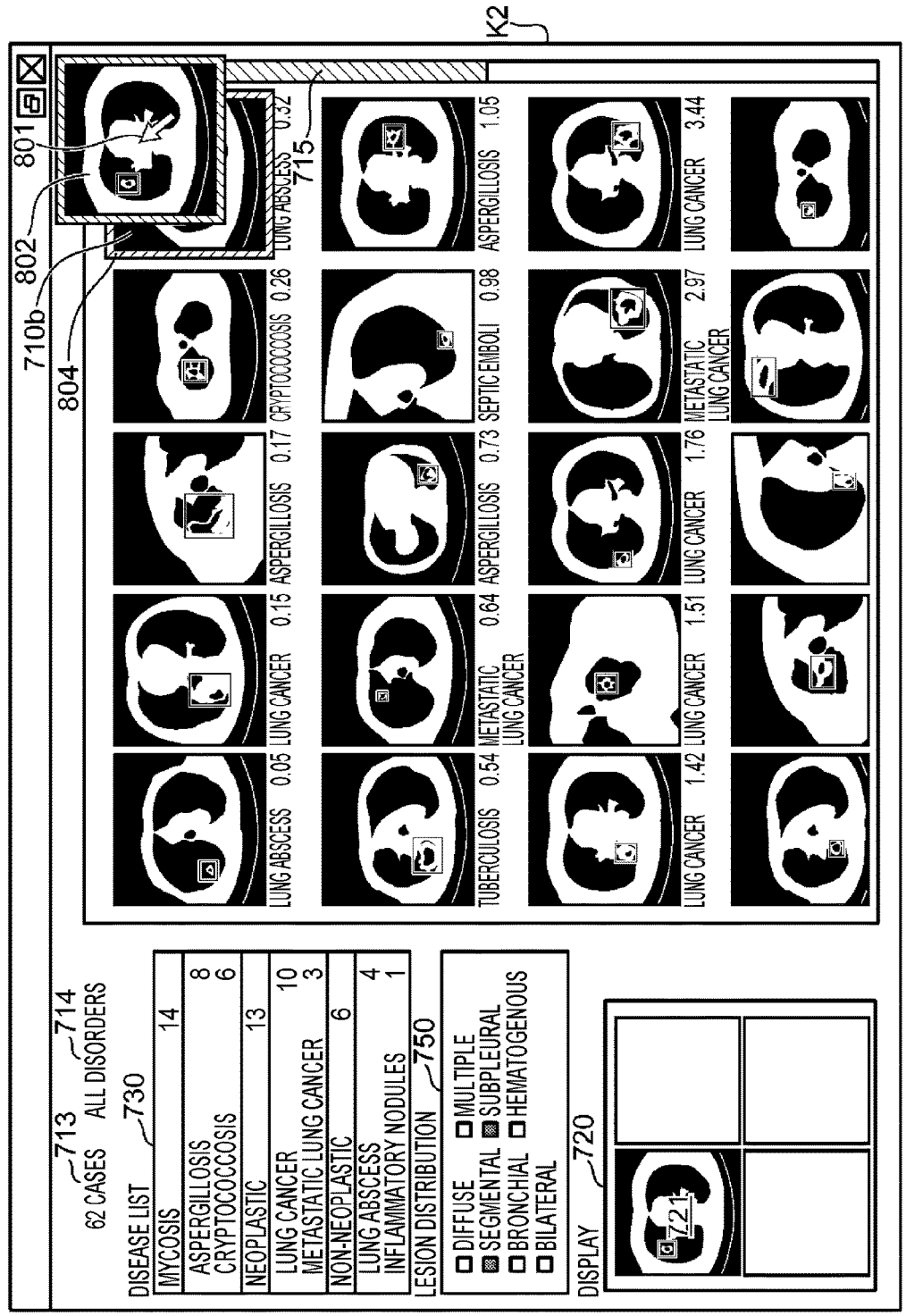
FIG. 12 is a diagram illustrating a basic screen in a case in which the insertion of a search query image at the position of a thumbnail image being displayed on the right edge of a case display area is prohibited.

FIG. 12 is a diagram illustrating the basic screen K2 in a case in which the insertion of the search query image 802 at the position of the thumbnail image 710*b* being displayed on the right edge of the case display area 710 is prohibited. In the embodiment of FIG. 12, the thumbnail image 710*b* does not move even if the certain amount of time or more elapses while the position of the mouse pointer 801 is over the thumbnail image 710*b*.

The display controller 104 displays a thick frame 804 around the thumbnail image 710*b* to present an emphasized display indicating that insertion is prohibited. This indicates that the case display area 710 is operating normally and not malfunctioning. The display controller 104 may also display the thick frame 804 in a red color. If the thick frame 804 is displayed in a red color, the insertion prohibition is indicated more clearly.

Figure 13:
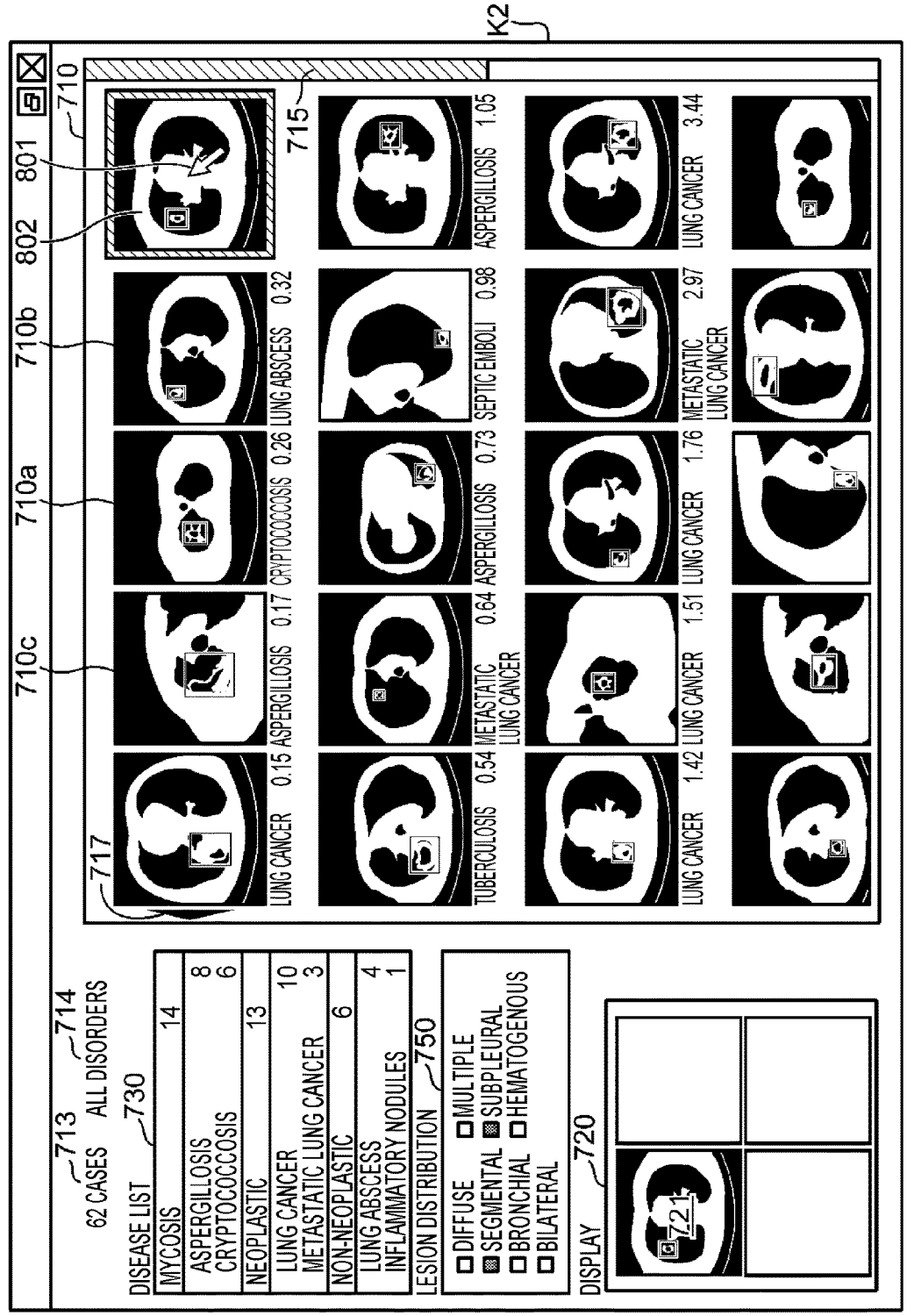
FIG. 13 is a diagram illustrating a basic screen in a case in which a search query image is inserted on the right edge of a case display area, and thumbnail images move to the left.

Alternatively, as illustrated in FIG. 13, when the search query image is inserted on the right edge of the case display area 710, the movement direction of the thumbnail images may be to the left.

FIG. 13 is a diagram illustrating the basic screen K2 in a case in which a search query image 802 is inserted on the right edge of the case display area 710, and thumbnail images move to the left. The input controller 103 senses that the position of the mouse pointer 801 has stopped for a certain amount of time or more inside a certain area including the thumbnail image 710*b* on the right edge of the case display area 710. Subsequently, the display controller 104 moves the thumbnail image 710*b*, and all of the thumbnail images on the same row being displayed to the left of the thumbnail image 710*b*, to the left. With this function, the search query image 802 is inserted on the right side of the thumbnail image 710*b* on the right edge of the case display area 710, making it possible to compare the thumbnail image 710*b* and the search query image 802.

In the operation of FIG. 13, the thumbnail image 710*d* that was being displayed on the left edge of the case display area 710 (see FIG. 9) is no longer displayed. Accordingly, the display controller 104 may also display the scroll button 717 on the left edge of the case display area 710, as illustrated in FIG. 13. If the input controller 103 senses an operation performed on the scroll button 717, the display controller 104 scrolls the medical images on the first row of the case display area 710 to the right.

However, if the medical images on the first row of the case display area 710 are scrolled to the right, the inserted search query image 802 will no longer be displayed. Accordingly, the display controller 104 may also not display the scroll button 717.

In the embodiment illustrated in FIGS. 8 to 11, by operating the scroll button 716, the search query image 802 may be inserted to the left of the thumbnail image 710*b* being displayed on the right edge of the case display area 710, and the thumbnail image 710*b* and the search query image 802 may be compared. Also, in the embodiment illustrated in FIG. 13, the search query image 802 may be inserted to the right of the thumbnail image 710*b* being displayed on the right edge of the case display area 710, and the thumbnail image 710*b* and the search query image 802 may be compared.

Accordingly, in the present embodiment, it may be configured so that when inserting the search query image 802 on the right edge of the case display area 710, the user may select whether to move the thumbnail images being displayed in the case display area 710 to the right or to the left.

In the description of the "Operation of inserting the search query image into the case display area 710" section above, the "search query image" may also be construed as "the thumbnail image of the search query image".

(Disease List)

Returning to FIG. 6, in the upper part on the left side of the basic screen K2, the disease list display area 730 is disposed under the heading "Disease List". In the disease list display area 730, the names of the diseases according to the definite diagnoses of all similar cases acquired as the similar case search results are displayed. After the case to be diagnosed is diagnosed and a definite diagnosis is made, that case is stored in the case search system 300 as a similar case. Consequently, each similar case has been assigned a disease according to a definite diagnosis.

FIG. 14 is an enlarged view of the disease list display area 730. In FIG. 14, the names of diseases according to definite diagnoses are displayed split between major disease classifications (731, 734, 737, 741, 744) and fine disease classifications (732, 733, 735, 736, 738, 739, 740, 742, 743, 745). In the example of FIG. 6, Mycosis 731, Neoplastic 734, Non-neoplastic 737, Mycobacteriosis 741, and Other 744 are displayed as major disease classifications.

Also, in the example of FIG. 14, Aspergillosis 732 and Cryptococcosis 733 are displayed as fine disease classifications of Mycosis 731. Also, Lung Cancer 735 and Metastatic Lung Cancer 736 are displayed as fine disease classifications of Neoplastic 734. Also, Lung Abscess 738, Sarcoidosis 739, and Septic Emboli 740 are displayed as fine disease classifications of Non-neoplastic 737. Also, Nontuberculous mycobacteria (NTM) 742 and Tuberculosis 743 are displayed as fine disease classifications of Mycobacteriosis 741. Also, Bronchiectasis 745 is displayed as a fine disease classification of Other 744.

Figure 15:
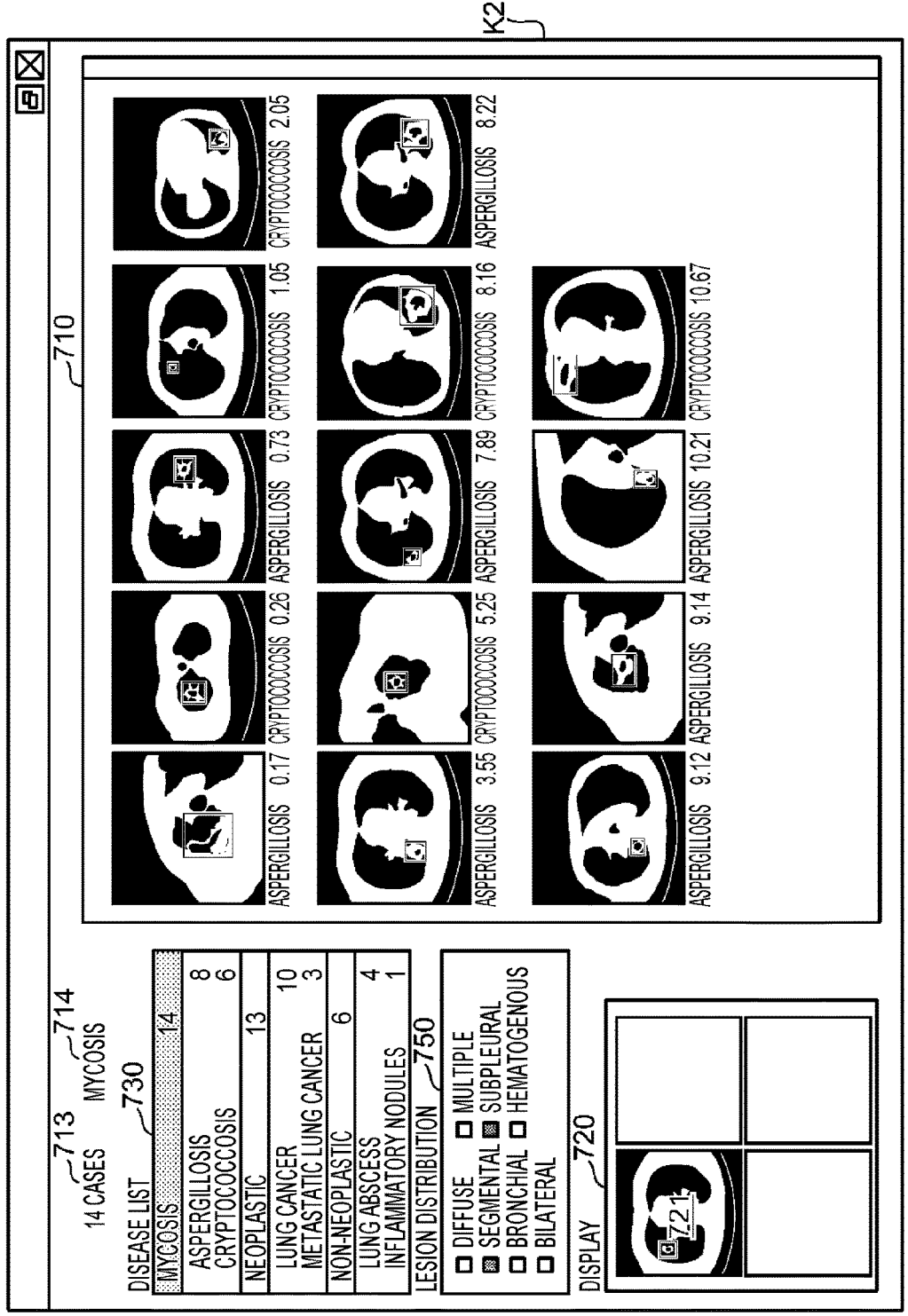
FIG. 15 is a diagram illustrating a basic screen when similar cases are filtered by "mycosis"

In addition, beside each major disease classification and each fine disease classification, the number of cases of that disease is displayed. The user is able to filter the similar cases displayed in the case display area 710 by selecting an arbitrary row of a major disease classification or a fine disease classification in the disease list display area 730. As illustrated in FIG. 6, in the state immediately after a similar case search, 62 similar cases including a variety of disorders are available for display, but if the Mycosis 731 row in FIG. 14 is clicked with the mouse, the display controller 104 displays only the similar cases of mycosis in the case display area 710, as illustrated in FIG. 15. Also, if the Metastatic Lung Cancer 736 row in FIG. 14 is clicked with the mouse, the display controller 104 displays only the similar cases of metastatic lung cancer in the case display area 710, as illustrated in FIG. 16.

At this point, the display controller 104 displays the filtered diseases in the display condition display area 714 so that the user is able to understand the conditions under which the similar cases being displayed in the case display area 710 have been filtered currently.

FIG. 15 is a diagram illustrating the basic screen K2 when the similar cases are filtered by "mycosis". FIG. 16 is a diagram illustrating the basic screen K2 when the similar cases are filtered by "metastatic lung cancer".

Figure 16:
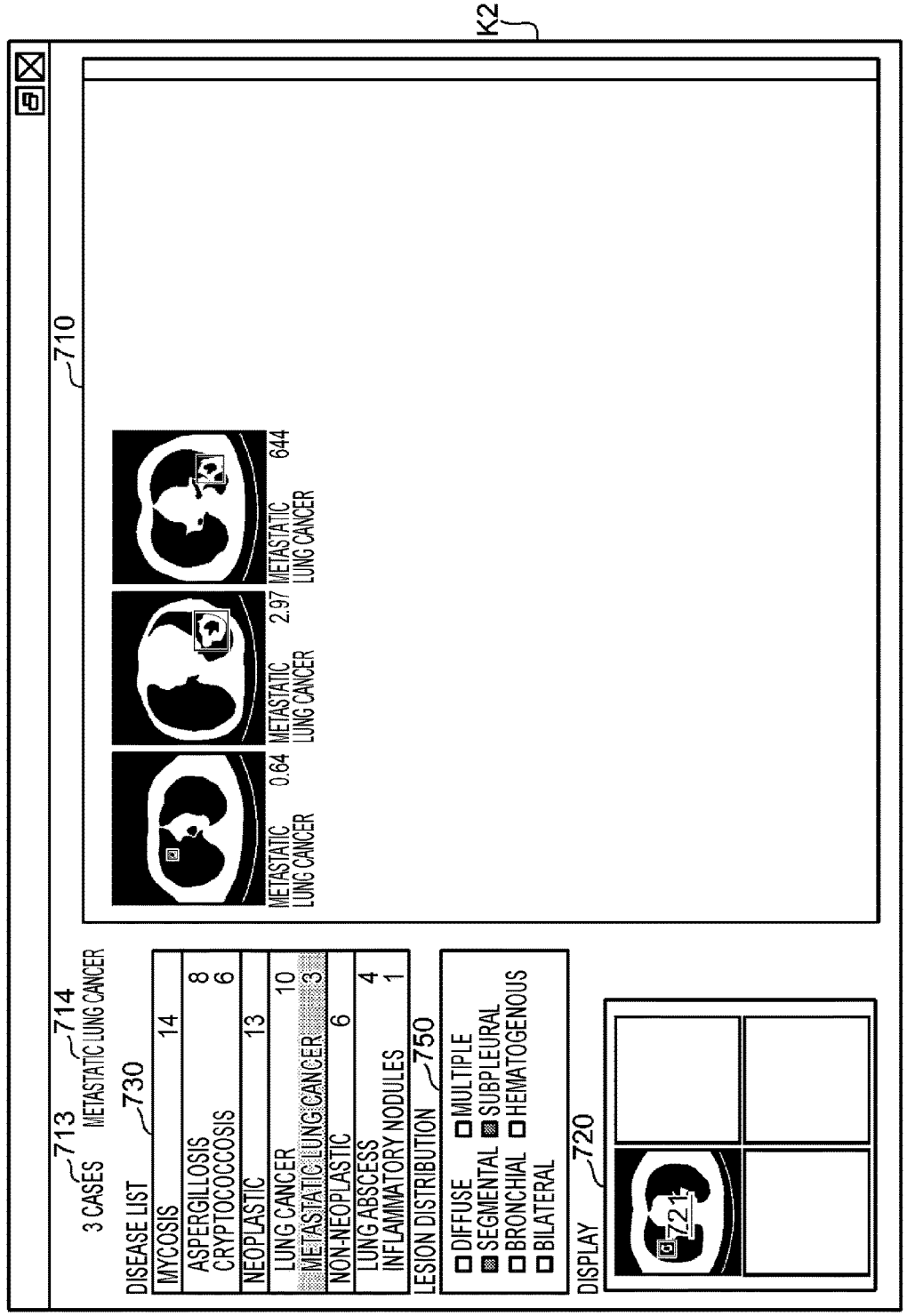
FIG. 16 is a diagram illustrating a basic screen when similar cases are filtered by "metastatic lung cancer"

In the example of FIG. 15, since a "mycosis" filter has been applied, "Mycosis" is displayed in the display condition display area 714, whereas in FIG. 16, since a "metastatic lung cancer" filter has been applied, "Metastatic Lung Cancer" is displayed in the display condition display area 714.

Also, at this point, the display controller 104 displays the number of search hits in the search hit display area 713 so that the user is able to understand how many similar cases are being displayed in the case display area 710 currently. In the example of FIG. 15, there are 14 similar cases corresponding to "mycosis", and thus "14 Cases" is displayed in the search hit display area 713, whereas in the example of FIG. 16, there are three similar cases corresponding to "metastatic lung cancer", and thus "3 Cases" is displayed in the search hit display area 713.

According to this function, only the similar cases of a disease assumed by the physician as the target of image diagnosis are displayed in the case display area 710, and the physician is able to easily check whether or not the case to be diagnosed contradicts the assumed disease.

In FIG. 15, the thumbnail images of M similar cases (in FIG. 15, M=14) are displayed in the case display area 710, which has a maximum number of displayable cases ND (in this embodiment, ND=20).

(Lesion Distribution)

In the middle part on the left side of the basic screen K2 illustrated in FIG. 6, the distribution list display area 750 is disposed under the heading "Lesion Distribution". In the distribution list display area 750, types of lesion distributions of all similar cases acquired from the case search system 300 as a result of searching for similar cases are displayed.

FIG. 17 is an enlarged view of the distribution list display area 750. In the example of FIG. 17, the names of seven lesion distributions are displayed, and a checkbox is disposed on the left side of each name of a lesion distribution. In the example of FIG. 17, Diffuse 751, Segmental 752, Bronchial 753, Bilateral 754, Multiple 755, Subpleural 756, and Hematogenous 757 are displayed as lesion distributions.

These lesion distributions are predefined, and each similar case is assigned in advance a distribution flag value indicating whether or not any of the distributions from Diffuse 751 to Hematogenous 757 are applicable (applicable: 1, not applicable: 0). Depending on the similar case, all distribution flag values may be set to not applicable (0) in some cases, whereas multiple distribution flag values may be set to applicable (1) in other cases.

The case search system 300 according to the present embodiment searches for similar cases having a region of interest that resembles a region of interest set by the user in a slice image of the case to be diagnosed. Lesions may also exist in slice images other than the slice image in which the user set the region of interest. Additionally, in some situations, after searching for similar cases by using a slice image with a region of interest set, the user may want to compare the similar cases resulting from the search with slice images other than the slice image that was used to perform the search. In such situations, the user inputs an operation to go to the next slice and display another slice image in the medical image viewer 610, and performs the work of comparing the other slice image to the similar cases found by the search. At this point, if only similar cases related to the lesion that the user is focusing on were displayed in the case display area 710 from among all the similar cases found by the search, the user would be able to perform smoothly the work of extracting slice images having the desired lesion from among the slice images other than the slice image in which the region of interest was set. Accordingly, the present embodiment, a function of filtering the similar cases found by search according to a desired lesion distribution is provided to enable such work to be performed more smoothly.

In the present embodiment, the lesion distributions indicated from Diffuse 751 to Hematogenous 757 in FIG. 17 are adopted as lesion distributions in the lung field region. Also, like in FIG. 17, regarding the check boxes and lesion distributions, the display controller 104 displays filterable lesion distributions in an active state, and displays non-filterable lesion distributions in an inactive state. Herein, for the active state, a state in which the brightness is high compared to the inactive state is adopted, whereas for the inactive state, a state in which the brightness is low compared to the active state is adopted.

In the example of FIG. 17, Diffuse 751 and Bronchial 753 to Hematogenous 757 are displayed in the active state, while Segmental 752 is displayed in the inactive state. This is because currently, the distribution flag value for each of Diffuse 751 and Bronchial 753 to Hematogenous 757 is set to 1 (applicable) for at least one similar case from among all the similar cases acquired by the similar case search, whereas the distribution flag value for Segmental 752 is set to 0 (not applicable) for all of the acquired similar cases.

If the input controller 103 senses that a checkmark has been input into one or more check boxes among the check boxes in the active state, the display controller 104 displays in the case display area 710 only the similar cases corresponding to the one or more checked lesion distributions.

Note that for Segmental 752, the distribution flag value is set to 0 (not applicable) for all of the similar cases acquired as the search results. For this reason, if a configuration allowing Segmental 752 to be checked were adopted, and a checkmark was input into this lesion distribution, no similar cases would be displayed in the case display area 710 at all, and inputting the checkmark would be meaningless. Accordingly, in the present embodiment, to avoid such situations, lesion distributions for which the distribution flag value is 0 (not applicable) for all similar cases acquired as the search results are displayed in the inactive state.

Figure 19:
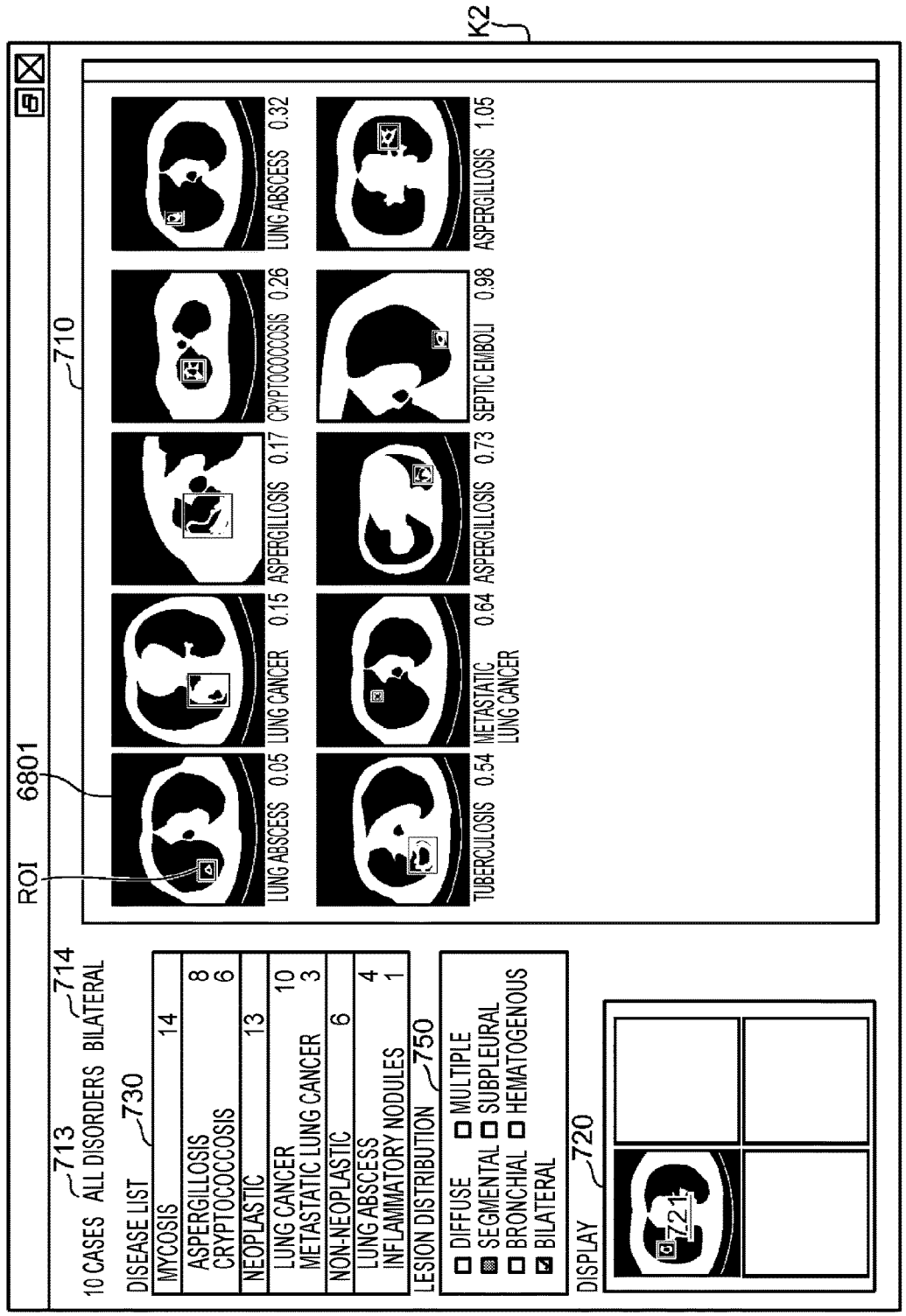
FIG. 19 is a diagram illustrating a basic screen filtered by bilateral lesion distribution.

FIG. 18 is a diagram illustrating the distribution list display area 750 in which a checkmark has been input into the Bilateral 754 check box. FIG. 19 is a diagram illustrating the basic screen K2 filtered by the Bilateral 754 lesion distribution. When a checkmark is input into the check box for Bilateral 754, as illustrated in FIG. 18, the display controller 104 displays only the similar cases having a bilateral lesion distribution in the case display area 710, as illustrated in FIG. 19. In this example, there are 10 similar cases having a bilateral lesion distribution. For this reason, the display controller 104 displays "10 Cases" in the search hit display area 713. Additionally, in the display condition display area 714, the display controller 104 displays the name of the disease to be displayed, and the name of the lesion distribution, namely "Bilateral". In the example of FIG. 19, a filter by the diseases listed the disease list display area 730 has not been applied, and thus "All Disorders" is displayed in the display condition display area 714.

When a checkmark is input into the check box for Bilateral 754, as illustrated in FIG. 18, the display controller 104 displays thumbnail images zoomed in by a zoom ratio corresponding to the selected lesion distribution in the case display area 710, as illustrated in FIG. 19. When the lesion distribution "Bilateral" is selected, it is necessary to be able to observe both sides of the lungs. Accordingly, the display controller 104 displays thumbnail images at a zoom ratio of 1.0×.

Similarly, when a checkmark is input into the check box for Multiple 755, the display controller 104 displays only the similar cases having a multiple lesion distribution in the case display area 710. When the lesion distribution "Multiple" is selected, it is necessary to be able to check the distribution of multiple lesions. Accordingly, the display controller 104 displays thumbnail images at a zoom ratio of 1.0×.

Similarly, when a checkmark is input into the check box for Diffuse 751, the display controller 104 displays only the similar cases having a diffuse lesion distribution in the case display area 710. When the lesion distribution "Diffuse" is selected, it is necessary to be able to check the distribution of a diffuse lesion spread out over a wide range. Accordingly, the display controller 104 displays thumbnail images at a zoom ratio of 1.0×.

Similarly, when a checkmark is input into the check box for Hematogenous 757, the display controller 104 displays only the similar cases having a hematogenous lesion distribution in the case display area 710. With a hematogenous lesion, there is a possibility that the lesion may metastasize to sites other than the lesion of interest. Consequently, it is necessary to check the entire image. For this reason, the display controller 104 displays thumbnail images at a zoom ratio of 1.0×.

Figure 21:
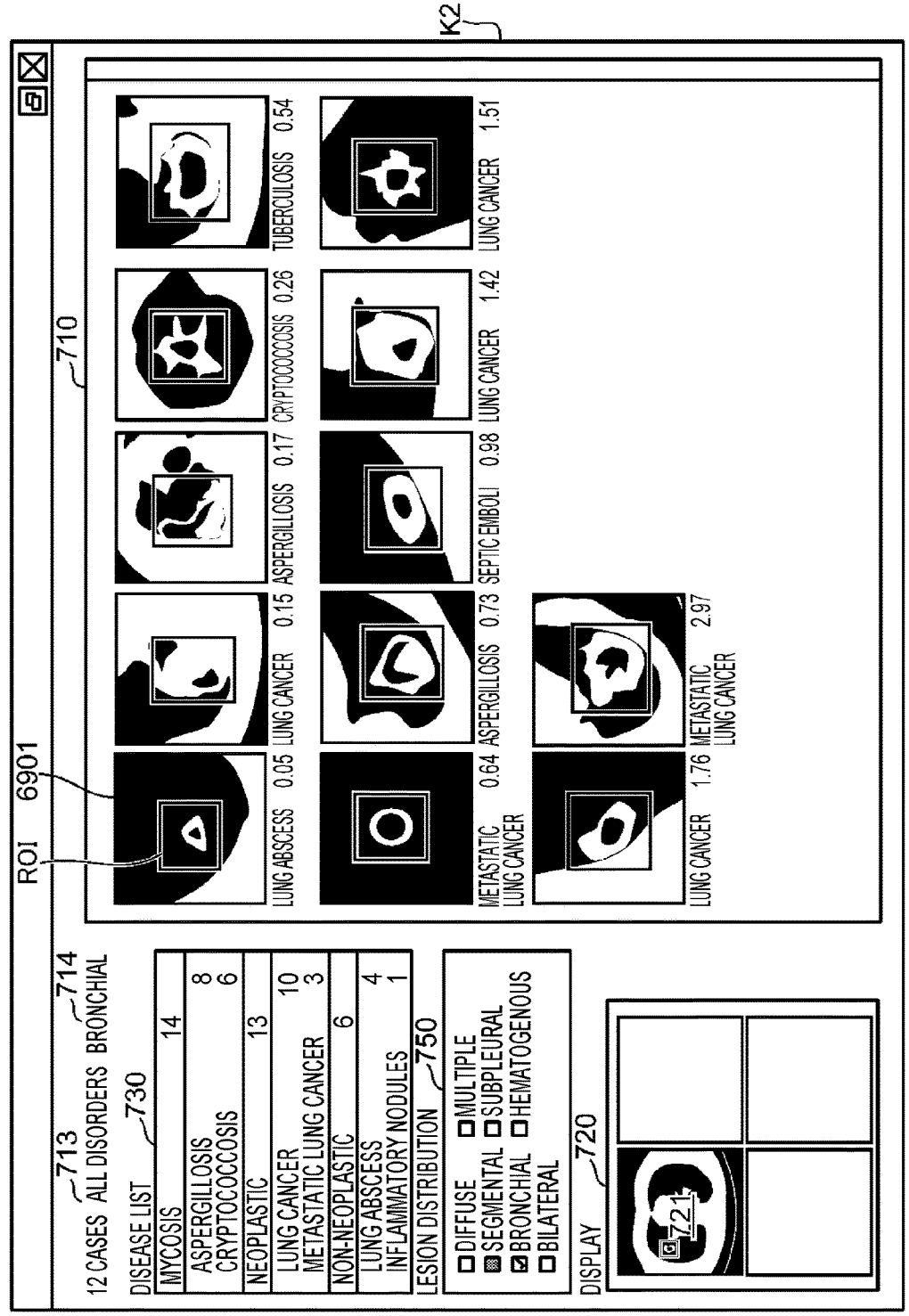
FIG. 21 is a diagram illustrating a basic screen filtered by bronchial lesion distribution.

FIG. 20 is a diagram illustrating the distribution list display area 750 in which a checkmark has been input into the Bronchial 753 check box. FIG. 21 is a diagram illustrating the basic screen K2 filtered by the Bronchial 753 lesion distribution. When a checkmark is input into the check box for Bronchial 753, as illustrated in FIG. 20, the display controller 104 displays only the similar cases having a bronchial lesion distribution in the case display area 710, as illustrated in FIG. 21. In this example, there are 12 similar cases having a bronchial lesion distribution. For this reason, the display controller 104 displays "12 Cases" in the search hit display area 713. Additionally, in the display condition display area 714, the display controller 104 displays the name of the disease to be displayed, and the name of the lesion distribution, namely "Bronchial". In the example of FIG. 21, a filter by the diseases listed the disease list display area 730 has not been applied, and thus "All Disorders" is displayed in the display condition display area 714.

When a checkmark is input into the check box for Bronchial 753, as illustrated in FIG. 20, the display controller 104 displays thumbnail images zoomed in by a zoom ratio corresponding to the selected lesion distribution in the case display area 710, as illustrated in FIG. 21. When the lesion distribution "Bronchial" is selected, it is necessary to be able to determine whether or not the region is bronchial. Accordingly, the display controller 104 displays each thumbnail image zoomed in by a zoom factor so that the surface area of the region of interest becomes approximately one-half the display area.

Similarly, when a checkmark is input into the check box for Segmental 752, the display controller 104 displays only the similar cases having a segmental lesion distribution in the case display area 710. When the lesion distribution "Segmental" is selected, it is necessary to be able to check the details of a segmental lesion. Accordingly, the display controller 104 displays each thumbnail image zoomed in by a zoom factor so that the surface area of the region of interest becomes approximately one-half the display area.

Figure 23:
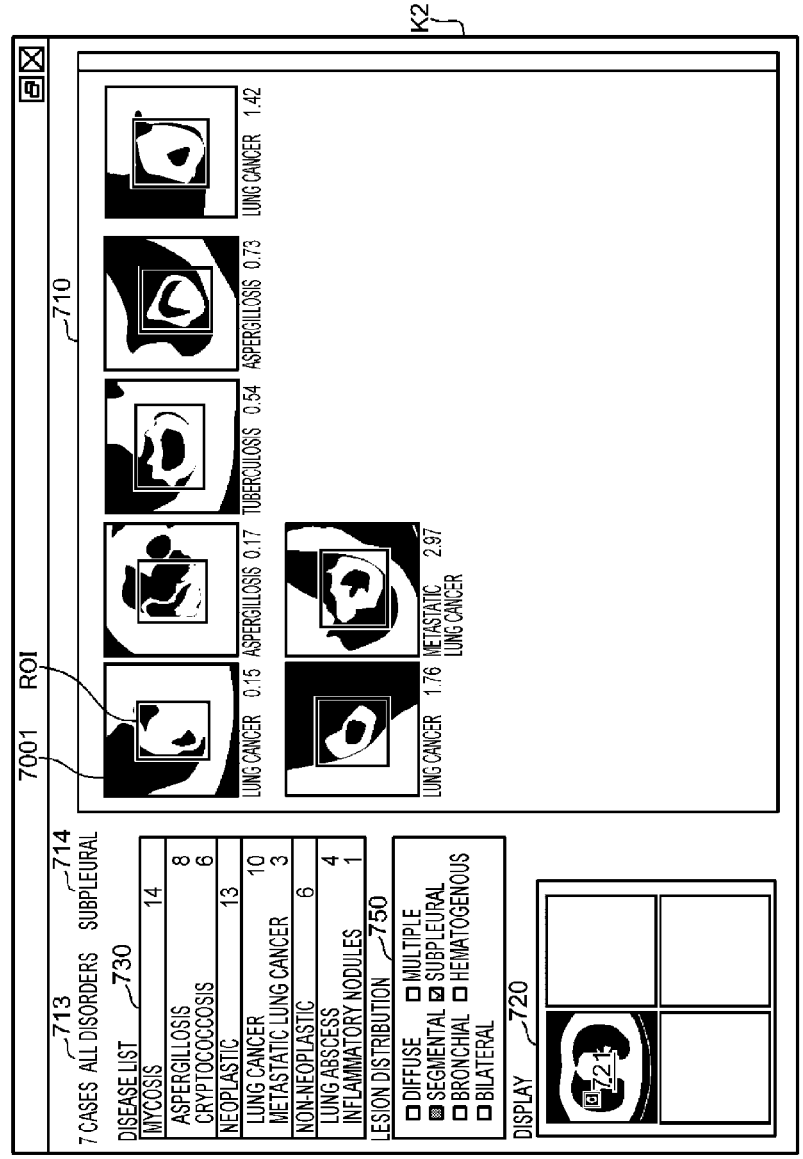
FIG. 23 is a diagram illustrating a basic screen filtered by subpleural lesion distribution.

FIG. 22 is a diagram illustrating the distribution list display area 750 in which a checkmark has been input into the Subpleural 756 check box. FIG. 23 is a diagram illustrating the basic screen K2 filtered by the Subpleural 756 lesion distribution. When a checkmark is input into the check box for Subpleural 756, as illustrated in FIG. 22, the display controller 104 displays only the similar cases having a subpleural lesion distribution in the case display area 710, as illustrated in FIG. 23. In this example, there are 7 similar cases having a subpleural lesion distribution. For this reason, the display controller 104 displays "7 Cases" in the search hit display area 713. Additionally, in the display condition display area 714, the display controller 104 displays the name of the disease to be displayed, and the name of the lesion distribution, namely "Subpleural". In the example of FIG. 23, a filter by the diseases listed the disease list display area 730 has not been applied, and thus "All Disorders" is displayed in the display condition display area 714.

When a checkmark is input into the check box for Subpleural 756, as illustrated in FIG. 22, the display controller 104 displays thumbnail images zoomed in by a zoom ratio corresponding to the selected lesion distribution in the case display area 710, as illustrated in FIG. 23. When the lesion distribution "Subpleural" is selected, it is necessary to be able to observe the positional relationship with the pleura. Accordingly, the display controller 104 displays each thumbnail image zoomed in by a zoom factor so that the pleura are included.

Note that the process of zooming each thumbnail image when a lesion distribution is selected as in FIGS. 19, 21, and 23 will be discussed in detail later.

(Patient Information 1000)

FIG. 24 is a diagram illustrating a data structure of the patient information 1000. The patient information 1000 is stored in the patient information storage 201 for each patient and managed by the patient information manager 202 in the medical information management system 200. In the patient information 1000, personal information such as the sex and age of the patient, clinical information such as a medical history, and examination information such as a blood test are registered. As illustrated in FIG. 24, the patient information 1000 includes a patient ID 1100, a name 1200, an age 1300, a sex 1400, a medical history 1500, a family history 1600, a chief complaint 1700, examination information 1800, and a definite diagnosis 1900.

The patient ID 1100 is an identifier unique to the patient. The name 1200, the age 1300, the sex 1400, the medical history 1500, the family history 1600, and the chief complaint 1700 are the name, the sex, the medical history, the family history, and the chief complaint of the patient with the patient ID 1100, respectively. The examination information 1800 expresses information related to one or more examinations that the patient has undertaken in the past, as illustrated in FIG. 25.

FIG. 25 is a diagram illustrating a data structure of the examination information 1800 registered in the patient information 1000 illustrated in FIG. 24. The examination information 1800 is information related to examinations performed on the patient, and one set of examination information 1800 is created in correspondence with one examination. The examination information 1800 includes an examination ID 1810, an examination date 1820, an examination type 1830, and an examination result 1840. The examination ID 1810 is an identifier unique to the examination. The examination date 1820 is the date when the examination was performed. The examination type 1830 is the type of examination. The type of examination may be a blood test, a respiratory function test, an endoscopic examination, a plain X-ray scan, or a CT scan, for example.

In the case of a blood test, the examination result 1840 corresponds to the values of various indicators, such as the white blood cell count, LDH level, and GPT level. In addition, the examination result 1840 also corresponds to information such as a judgment made by a physician based on the various indicators. Also, in the case of an image scan such as a plain X-ray scan or a CT scan, pointer information to the captured images or pointer information to a report of the image diagnosis result is included. Note that images captured during an examination are stored in DICOM format in the medical image data storage 203 of the medical information management system 200.

In addition, if the examination type 1830 is an image scan such as a plain X-ray, CT, MRI, or PET scan, the resulting medical image data is archived in the medical image database 2000, which is stored in the medical image data storage 203 of the medical information management system 200.

Figure 26:
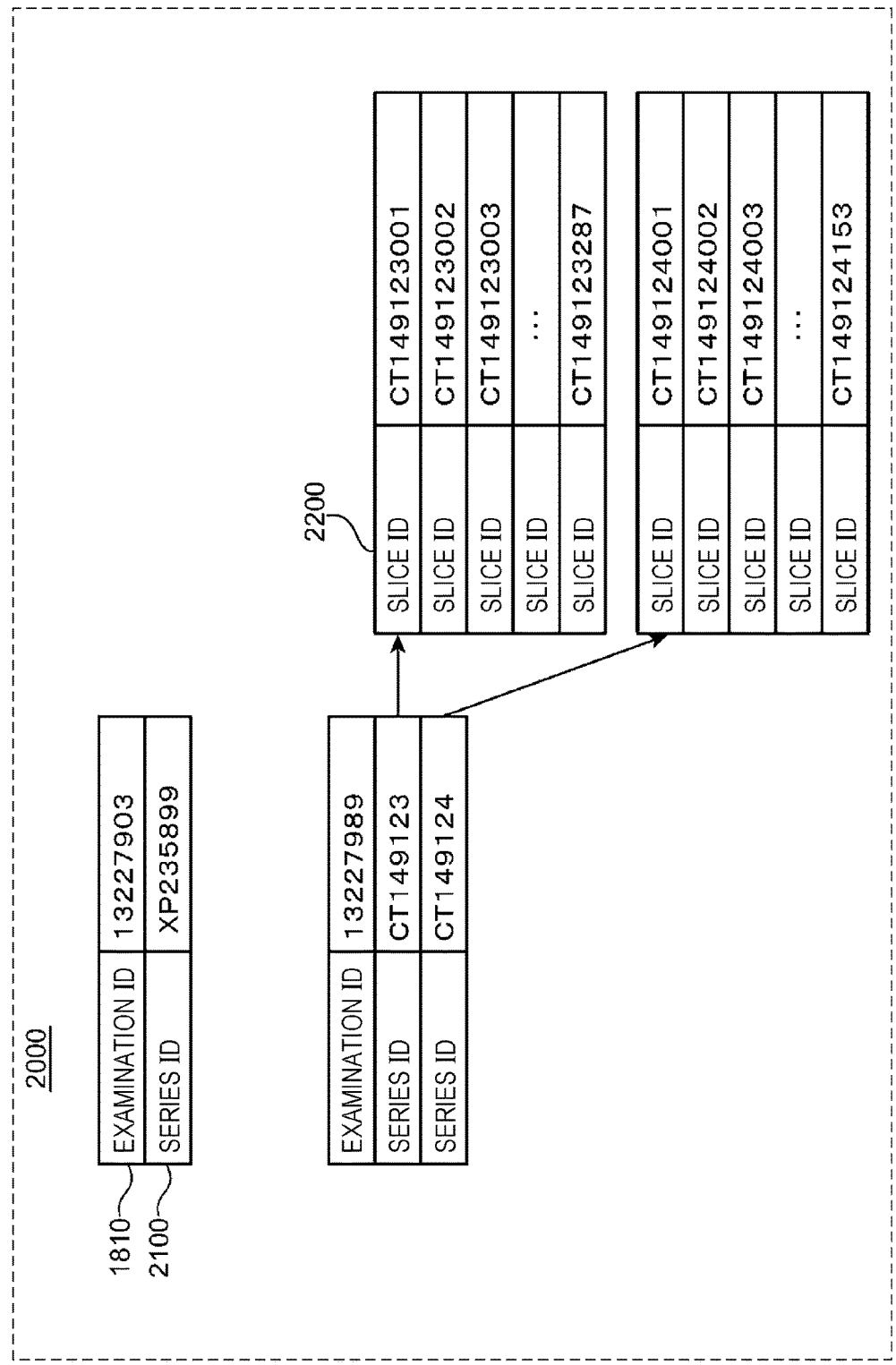
FIG. 26 is a diagram illustrating a data structure of a medical image database.

FIG. 26 is a diagram illustrating a data structure of the medical image database 2000. The medical image database 2000 includes the examination ID 1810 and a series ID 2100. Since multiple types of imaging (such as plain CT and contrast-enhanced CT, for example) may be conducted during a single examination, multiple series IDs 2100 may be associated with one examination ID 1810 in some cases. In other words, a number of series corresponding to the types of imaging is obtained.

In addition, different series may be obtained not only for separate types of imaging, but also for separate conditions of reconstructing the captured images. For example, if the captured images are reconstructed according to a lung field condition and a mediastinum condition, one series is obtained for each of these conditions. Note that in images reconstructed according to a lung field condition, features such as the blood vessels, the bronchi, and the alveoli of the lungs are highlighted for display. Meanwhile, in images reconstructed according to a mediastinum condition, mediastinum features such as blood vessels and lymph nodes are highlighted for display. Since a lung field condition and a mediastinum condition may be obtained by reconstructing images obtained by a single scan, if a plain CT scan and a contrast-enhanced CT scan are both conducted, and the images from these two scans are reconstructed according to a lung field condition and a mediastinum condition, respectively, two series of the lung field condition and two series of the mediastinum condition will be obtained.

In the case of CT and MRI image examinations, multiple slice images are obtained from a single scan, and thus multiple slice IDs 2200 are associated with one series ID 2100. In FIG. 26, the two series IDs "CT149123" and "CT147124" are associated with the examination ID "13227989", thus demonstrating that two series of CT images were obtained from this examination. FIG. 18A also demonstrates how multiple slice IDs 2200 are associated with each of the series IDs "CT149123" and "CT147124".

If the examination type 1830 is an image scan such as a plain X-ray, CT, MRI, or PET scan, a diagnosis report 3000 as illustrated in FIG. 27 is stored in the diagnosis report manager 205 of the medical information management system 200. In the diagnosis report 3000, the results of a diagnosis made by a physician for each examination are registered.

FIG. 27 is a diagram illustrating a data structure of the diagnosis report 3000. The diagnosis report 3000 includes the examination ID 1810, observations 3100, and a diagnosis 3200. The examination ID 1810 is the same as the examination ID 1810 illustrated in FIG. 25. Consequently, the diagnosis report 3000 and the examination information 1800 are associated together. In the observations 3100, remarks expressing the physician's opinions on the examination are registered. In the diagnosis 3200, remarks expressing the physician's diagnosis with respect to the examination are registered.

FIG. 28 is a diagram illustrating a data structure of the similar case data 4000. The similar case data 4000 is data referenced when searching for similar cases that resemble the case to be diagnosed, and one set of similar case data 4000 is created in correspondence with one similar case. Note that the similar case data 4000 is an example of metadata for similar case data. The similar case data 4000 is stored for each similar case in the similar case data storage 301 of the case search system 300. As illustrated in FIG. 28, the similar case data 4000 includes a similar case ID 4100, a slice ID 4200, region of interest information 4300, image feature data 4400, thumbnail image data 4500, lesion distribution information 4600, a definite diagnosis (major disease classification) 4700, and a definite diagnosis (fine disease classification) 4800.

The similar case ID 4100 is an identifier of the similar case data 4000. Herein, since one set of similar case data is generated for each region of interest set in a slice image of a similar case, the similar case ID 4100 may also be said to be an identifier of a region of interest. In the example of FIG. 28, the similar case ID 4100 is a string made up of the letters "SIM" followed by a number.

The slice ID 4200 is an identifier of a slice image in which a region of interest is set, and is the same as the slice ID 2200 illustrated in FIG. 26. The region of interest information 4300 is information indicating the position of the region of interest set in the slice image.

Figure 29:
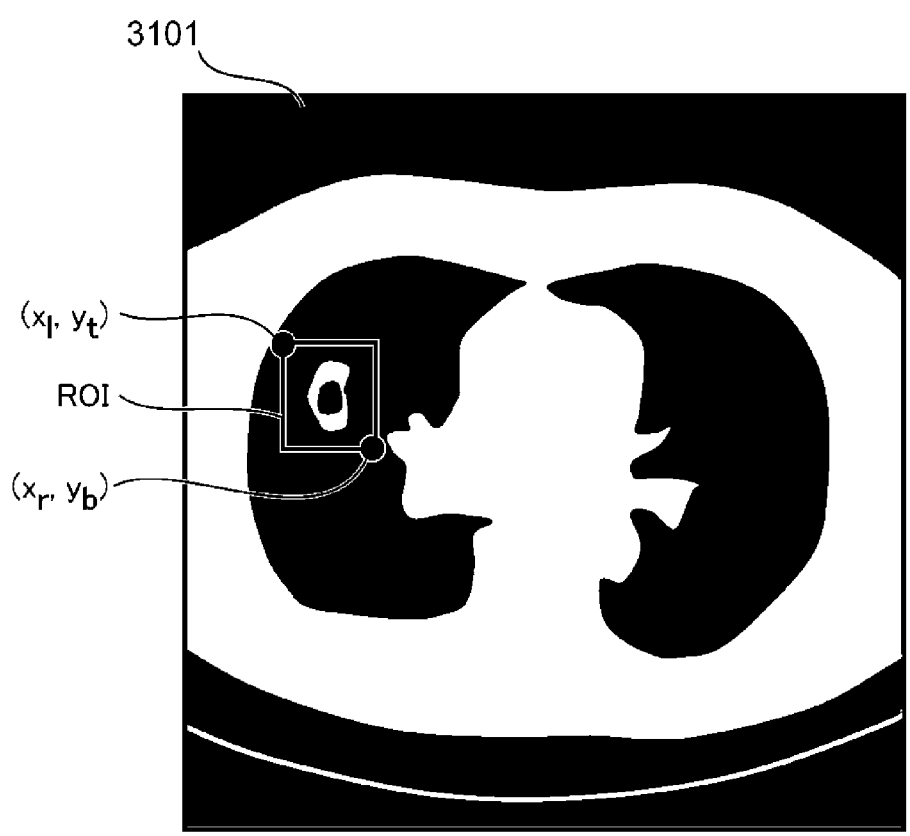
FIG. 29 is a diagram schematically illustrating a region of interest set in a slice image.

FIG. 29 is a diagram schematically illustrating a region of interest set in a slice image. In the example of FIG. 29, a rectangular region of interest is set. Consequently, the region of interest information 4300 includes four values: the coordinates of the top-left vertex of the region of interest $(x_l, y_t)$, and the coordinates of the bottom-right vertex $(x_r, y_b)$. Obviously, the region of interest may also be a shape other than rectangular, and in such a situation, parameters enabling a region to be specified uniquely are adopted as the region of interest information 4300. For example, if the region of interest is a circle, the center coordinates and the radius of the circle are adopted as the region of interest information 4300.

The image feature data 4400 includes feature values of certain dimensionality (herein, N dimensions) extracted from the region of interest defined by the region of interest information 4300. The thumbnail image data 4500 is the image data of a thumbnail image generated for display in the case display area 710, based on the slice image in DICOM format specified by the slice ID. Herein, in the thumbnail image data 4500, the pixel values of the thumbnail image are arranged in raster scan order proceeding from the top-left vertex to the bottom-right vertex of the thumbnail image, for example. As described earlier, a DICOM image obtained by a CT scan is 512×512 pixel, 11-bit (pixel values ranging from −1000 to +1000) image. Accordingly, in the present embodiment, to speed up the display of thumbnail images, a downscaling process and a tone conversion process are performed on the DICOM image that serves as the basis for a thumbnail image, and a thumbnail image having 8-bit pixel values is created in advance and registered in the similar case data 4000. Note that thumbnail images may be created by having the medical information management system 200 create and transmit thumbnail images to the case search system 300, or by having the case search system 300 create thumbnail images by acquiring DICOM images from the medical information management system 200, for example.

The lesion distribution information 4600 includes distribution flag values indicating whether or not any predetermined lesion distributions from Diffuse 4610 to Hematogenous 4670 are applicable to the relevant similar case (applicable: 1, not applicable: 0).

The definite diagnosis (major disease classification) 4700 is the major disease classification confirmed for the relevant similar case. The definite diagnosis (major disease classification) 4700 is used when filtering similar cases by the name of a major disease classification.

The definite diagnosis (fine disease classification) 4800 is the fine disease classification confirmed for the relevant similar case. The definite diagnosis (fine disease classification) 4800 is used when filtering similar cases by the name of a minor disease classification.

The major disease classification is predefined in unique correspondence with the definite diagnosis (fine disease classification) 4800, and the definite diagnosis (major disease classification) 4700 is stored in the similar case data 4000 by using this correspondence relationship.

The definite diagnosis (fine disease classification) 4800 is registered as follows. In the medical image data storage 203, the series ID 2100 is specified from the slice ID 2200 illustrated in FIG. 26. Subsequently, in the patient information storage 201, the examination ID 1810 is specified from the specified series ID, the corresponding patient information 1000 (FIG. 24) is specified from the examination ID 1810, and the definite diagnosis 1900 of the relevant patient is specified from the specified patient information 1000.

(Process Flow)

Next, the flow from the start of radiological interpretation work to the start of a similar case search in which the information terminal 100 works in conjunction with the medical information management system 200 and the case search system 300 will be described.

Figure 30:
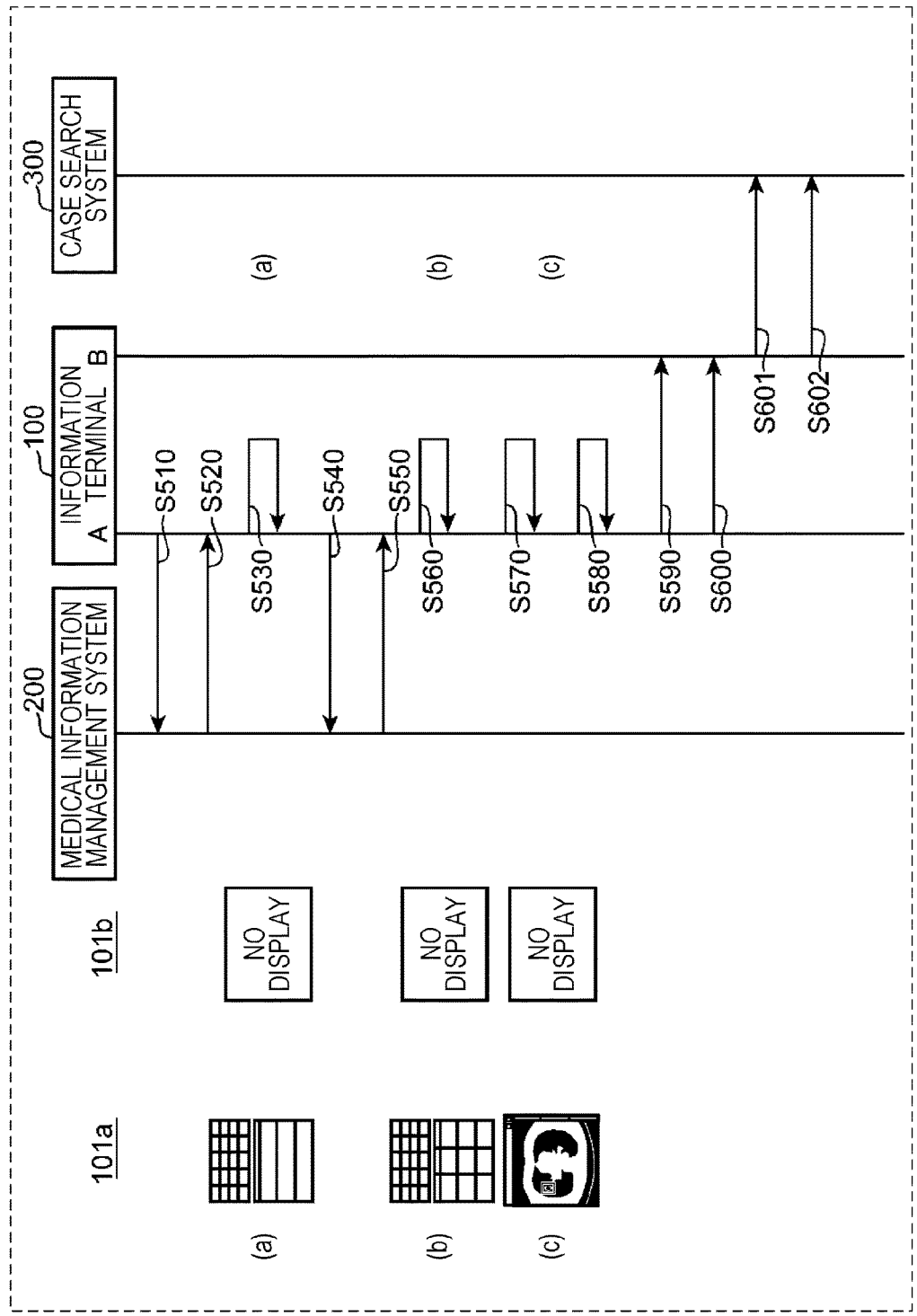
FIG. 30 is a sequence diagram illustrating a process in which an information terminal acquires a case to be diagnosed from a medical information management system and issues a request for a similar case search to a case search system, and the case search system receives the similar case search request.

FIG. 30 is a sequence diagram illustrating a process in which the information terminal 100 acquires a case to be diagnosed from the medical information management system 200 and issues a request for a similar case search to the case search system 300, and the case search system 300 receives the similar case search request. Note that in FIG. 30, the rectangles in the two columns to the left of the sequence diagram illustrate the screens displayed on the displays 101a and 101b by the processes in the corresponding steps. Also, in FIG. 30, "A" in the information terminal indicates the medical information management application, while "B" indicates the similar case search application. Herein, it is supposed that the medical information management application has been launched in advance before the sequence is started.

First, the information terminal 100 receives, via the operating unit 102, an examination list display request for displaying a list of examinations to be interpreted by the user (the physician performing radiological interpretation), and transmits, via the input controller 103 and the communication controller 110, the examination list display request to the communication controller 206 of the medical information management system 200 (S510).

The patient information manager 202 of the medical information management system 200 lists examinations for which image scanning has been performed but for which interpretation is unfinished, and generates an examination list of examinations to be interpreted. Subsequently, the patient information manager 202 transmits, via the communication controller 206, the generated examination list to the communication controller 110 of the information terminal 100 (S520). Herein, the examination list includes the patient information 1000 and the examination information 1800 of the relevant patient.

The display controller 104 of the information terminal 100 displays the examination list received by the communication controller 110 on the display 101 (S530).

In this case, the examination list is displayed on the display 101a, while nothing is displayed on the display 101b.

FIG. 31 is a diagram illustrating an examination list screen. The examination list includes an area 800 displaying examinations for which interpretation is unfinished, and an area 810 displaying information related to series included in an examination. In the area 800, the fields "Patient ID", "Patient Name", "Examination Date", "Examination ID", and "Examination Type" are provided. In the "Patient ID" and "Patient Name" fields, the patient ID 1100 and the name 1200 registered in the patient information 1000 are displayed, while in the "Examination Date", "Examination ID", and "Examination Type" fields, the examination date 1820, the examination ID 1810, and the examination type 1830 registered in the examination information 1800 are displayed. The area 810 is for displaying the details of an examination selected by the user in the area 800, and is provided with the fields "Series ID", "Definition", and "Image". At this point, since the user has not selected an examination (corresponding to a row) in the area 800, nothing is displayed in the area 810.

The user selects to examination to interpret next from among the examinations displayed in the area 800. After this selection is sensed by the input controller 103, as illustrated in FIG. 30, the communication controller 110 transmits a request to display all series included in the examination ID of the selected examination to the medical information management system 200 (S540).

After the communication controller 206 of the medical information management system 200 receives the display request, the patient information manager 202 references the medical image database 2000 illustrated in FIG. 26, acquires all slice images in all series included in the examination ID specified by the display request, and transmits the acquired slice images to the information terminal 100 via the communication controller 206 (S550). For example, in the example of FIG. 26, if the examination with the examination ID "13227989" is selected by the user, all slice images included in the series with the series IDs "CT149123" and "CT149124" are transmitted in S550.

After the communication controller 110 of the information terminal 100 acquires the images in all series, the display controller 104 displays, in the area 810, a series list that lists information related to all series included in the specified examination ID (S560).

In this case, a series list of the series corresponding to the examination selected in the area 800 is displayed in the area 810 of the examination list displayed on the display 101a, while nothing is displayed on the display 101b.

FIG. 32 is a diagram illustrating an examination list screen after an examination is selected. A highlight is applied to the background of the row selected in the area 800 of FIG. 32. In the example of FIG. 32, in the area 800, the examination of "Pana, Taro" on the second row is selected. For this reason, in the area 810, "Series ID", "Definition", and "Image" are displayed for the selected examination. Herein, in the "Series ID" field, the series IDs associated with the examination ID of the selected examination in the medical image database 2000 are displayed, while in the "Image" field, a thumbnail image of one slice image representative of each displayed series ID is displayed. Herein, an image at a certain slice position is adopted as the one slice image representative of each series ID. The certain slice position may be the first slice position or a central slice position. "Definition" indicates the imaging condition and the reconstruction condition for the relevant series. This "Definition", although omitted from illustration, is registered in association with the series ID in the medical image database 2000 of FIG. 26, for example.

Figure 33:
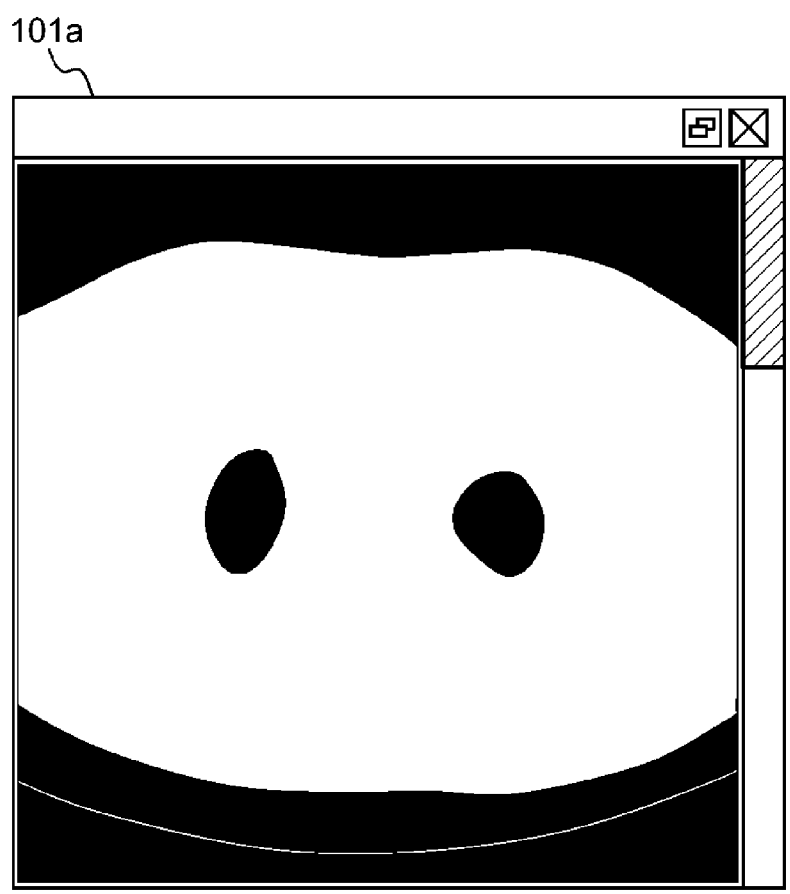
FIG. 33 is a diagram illustrating a slice image displayed on a display when a series is selected by a user.

In the area 810, a series to be interpreted is selected by the user, and after the input controller 103 senses this selection, the display controller 104 displays the first slice image of the selected series on the display 101a, as illustrated in FIG. 33 (S570).

FIG. 33 is a diagram illustrating a slice image displayed on the display 101a when a series is selected by the user. FIG. 33 is a diagram illustrating the first slice in a chest CT scan, and is a slice image at a shoulder position slightly closer to the head than the apical portion of the lungs. At this point, the display controller 104 displays the slice images on the display 101a in a state allowing all slice images in the selected series to be cycled through. Note that nothing is displayed on the display 101b. For example, the user inputs a slice-cycling operation of rotating the mouse wheel while the mouse pointer is positioned over the display 101a, and the input controller 103 senses this operation. Subsequently, the display controller 104 switches the slice image displayed on the display 101a to a slice image at another slice position, according to the amount of rotation of the mouse wheel. The user makes an image diagnosis while inputting slice-cycling operations. Additionally, if the user is having difficulty making an image diagnosis, the user launches the similar case search application.

At this point, the similar case search application may be launched by inputting a predetermined shortcut key on the keyboard of the operating unit 102, or a menu of the medical image viewer may be displayed with a right-click of the mouse, and the similar case search application may be launched by specifying a similar case search menu item from the menu. After an instruction to launch the similar case search application is given, the management of the information terminal 100 is passed to the ROI manager 105, and the information terminal 100 enters a standby state waiting to receive a region of interest (ROI).

Figure 34:
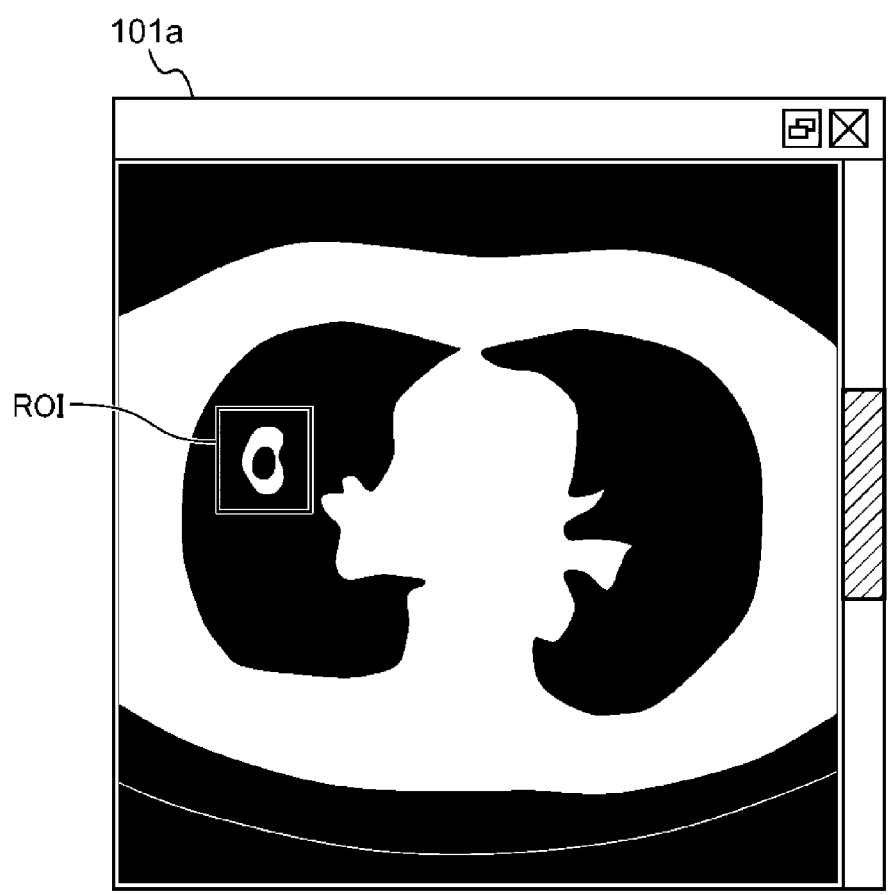
FIG. 34 is a diagram illustrating a slice image displayed on a display when a similar case search application is launched by a user.

FIG. 34 is a diagram illustrating a slice image displayed on the display 101a when a similar case search application is launched by a user. FIG. 34 is a slice image at a slice position cycled from the slice image of the first slice in FIG. 33. The user sets, via the operating unit 102, a region of interest (ROI) in a lesion on the slice image displayed on the display 101a (S580). At this point, as illustrated in FIG. 34, the user left-clicks the mouse to input the coordinates of the top-left vertex of the region of interest ROI in the slice image, for example. Subsequently, the user may input the bottom-right vertex of the region of interest ROI by keeping the left-click button held down and dragging the mouse diagonally down and to the right, and then releasing the left-click button.

After the input controller 103 senses the operation setting the region of interest, the ROI manager 105 receives the coordinate data of the top-left and the bottom-right vertices of the region of interest from the input controller 103, and generates the received coordinate data as region of interest information. Subsequently, the ROI manager 105 transmits the generated region of interest information to the communication controller 110 (S590).

At the same time, the ROI manager 105 transmits the slice image of the case to be diagnosed to the communication controller 110 (S600). In this case, the ROI manager 105 transmits the one slice image with the region of interest set by the user (the search query image) in the series selected by the user from among the slice images of all series that the information terminal 100 received from the medical information management system 200 in S550.

Next, the communication controller 110 receives the region of interest information transmitted from the ROI manager 105, and transmits the region of interest information to the communication controller 304 of the case search system 300 (S601).

At the same time, the communication controller 110 receives the slice image transmitted from the ROI manager 105, and transmits the slice image to the communication controller 304 of the case search system 300 (S602).

At this point, in S600 and S601, the slice image itself is transmitted, but transmitting the slice ID of the slice image is also acceptable. In this case, the case search system 300 receiving the slice ID may specify that slice ID to acquire the slice image from the medical information management system 200.

(Similar Case Search Flow)

Next, the process by which the case search system 300 performs a similar case search and the information terminal 100 presents the initial display of the similar case search results will be described.

Figure 35:
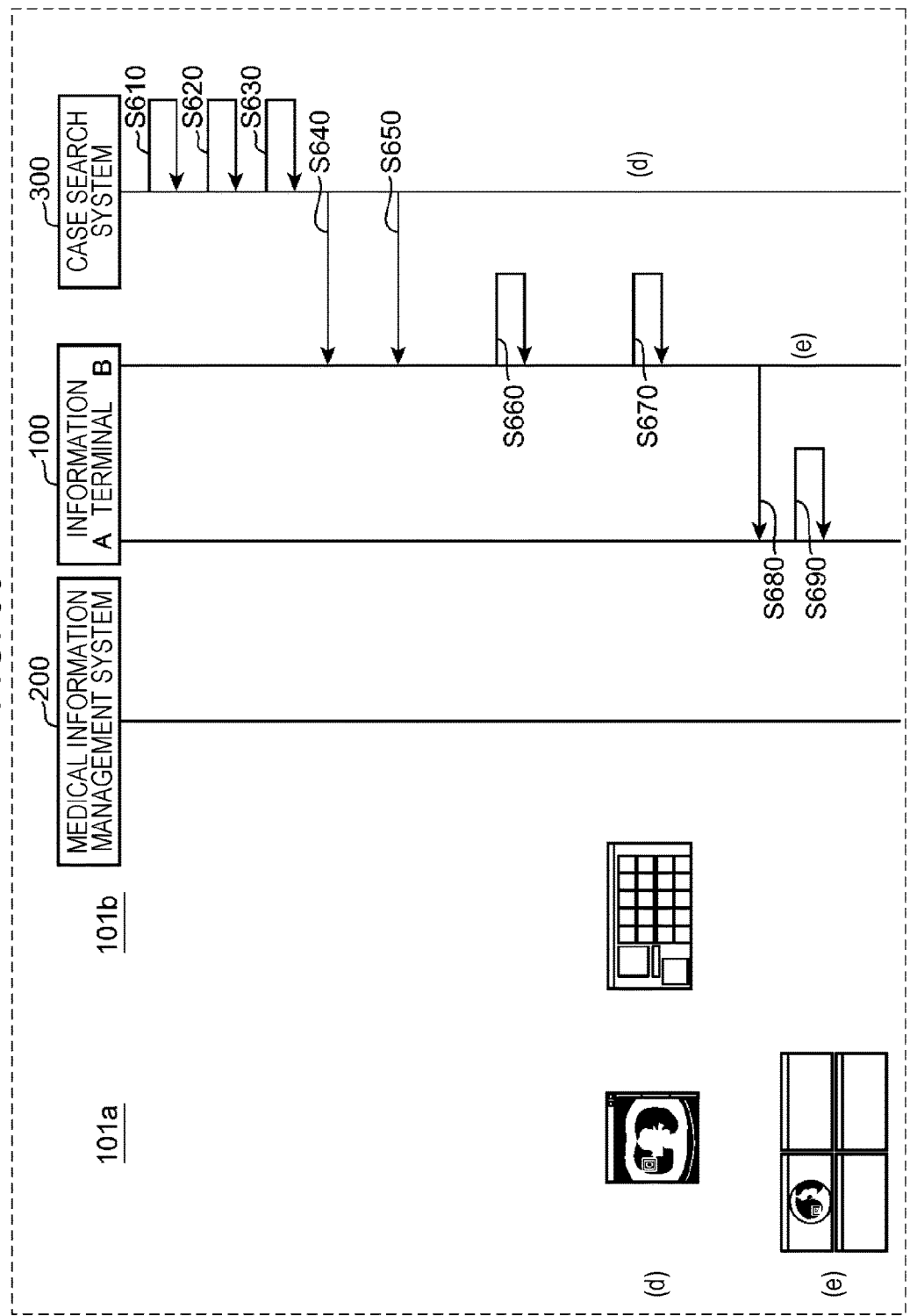
FIG. 35 is a sequence diagram illustrating a process in which a case search system receives a similar case search request, and replies to an information terminal with similar case search results.

FIG. 35 is a sequence diagram illustrating a process in which the case search system 300 receives a similar case search request, and replies to the information terminal 100 with similar case search results.

The image feature extractor 302 of the case search system 300 extracts predetermined, multidimensional image features from the region of interest set in the search query image (S610).

Image features related to the shape of the organ or the shape of the lesion portion in the medical image, or image features related to a brightness distribution may be adopted as the image features. For example, the use of 490-dimension image features is described in the non-patent literature by Nemoto et al., "Improvement of Tumor Detection Performance in Mammograms by Feature Selection from a Large Number of Features and Proposal of Fast Feature Selection Method", The transactions of the Institute of Electronics, Information and Communication Engineers. D-II, Vol. J88-D-II, No. 2, pp. 416-426, February 2005. In the present embodiment, the image features described in the above non-patent literature are adopted, for example. However, this is merely one example, and other image features may also be adopted.

The similar case search unit 303 compares the image features extracted by the image feature extractor 302 to the image features of each similar case stored in the similar case data storage 301 (S620). At this point, the similar case search unit 303 compares image features by computing the distance between the image feature data extracted from the search query image and the image feature data 4400 registered in the similar case data 4000 (see FIG. 28) stored for each similar case in the similar case data storage 301.

Next, the similar case search unit 303 sorts similar cases having a distance less than or equal to a certain threshold value in order of shortest distance, and decides these similar cases as the similar cases to be transmitted (S630). Next, the communication controller 304 transmits the similar case ID 4100, the slice ID 4200, the region of interest information 4300, the thumbnail image data 4500, the lesion distribution information 4600, the definite diagnosis (major disease classification) 4700, and the definite diagnosis (fine disease classification) 4800 of the similar cases decided as the similar cases to transmit from among the similar case data 4000 stored in the similar case data storage 301, as well as the distances computed by the similar case search unit 303, to the information terminal 100 (S640).

Thereafter, a process of generating the initial basic screen K2 on which the similar case search results are displayed (see FIG. 6) is executed. First, the management information used when generating the layout area 720 on the initial basic screen K2 will be described.

First, the communication controller 304 of the case search system 300 transmits layout information to the information terminal 100 (S650). Herein, layout information is information specifying the number of rows and the number of columns of the display boxes constituting the layout area 720.

Next, after the communication controller 110 of the information terminal 100 receives the layout information, the display box manager 106 registers the number of rows and the number of columns of display boxes specified by the transmitted layout information in the display box management information 4410 (see FIG. 36), and also registers the slice ID of the search query image in the display box management information (see FIG. 36) (S660).

FIG. 36 is a diagram illustrating a data structure of the display box management information 4410. The display box management information 4410 includes a table 4411 in which the number of rows and the number of columns are registered, and a table 4412 in which the slice ID of the slice image displayed in each display box is registered. Consequently, the display box manager 106 registers the number of rows and the number of columns specified by the layout information transmitted from the case search system 300 in the "No. of Rows" and "No. of Columns" fields of the table 4411. Also, in the present embodiment, a thumbnail image of the search query image is displayed in the top-left display box 721 from among the four display boxes. Accordingly, the display box manager 106 registers the slice ID of the search query image transmitted from the medical information management system 200 in the "Row 1 Column 1" item of the table 4412. Note that the case search system 300 may also create a thumbnail image of the search query image, and transmit the created thumbnail image of the search query image to the information terminal 100 in S640 or S650.

Herein, default values for the number of rows and the number of columns of the display boxes constituting the layout area 720 are preset by the case search system 300. Herein, the default values for the number of rows and the number of columns is two rows and two columns, for example. For this reason, "2" rows and "2" columns are registered in the display box management information 4410 illustrated in FIG. 36.

In the example of FIG. 6, the display boxes are displayed in a 2×2 layout in the layout area 720. The number of rows and the number of columns in the layout area 720 may be set freely by the user.

The layout information of the layout area 720 set by the user may be managed by the information terminal 100 or managed by the case search system 300. Note that if the layout information is managed by the case search system 300, the layout information of the relevant user is transmitted to the information terminal 100 in S650 of FIG. 35.

Next, the display controller 104 uses the similar case data transmitted in S640 and the display box management information 4410 saved in S660 to generate the initial basic screen K2 on which the similar case search results are displayed (S670).

In this case, the basic screen K2 illustrated in FIG. 6 is displayed on the display 101b. Also, the search query image is displayed on the display 101a.

(Similar Case Search Results Display Flow)

Figure 37:
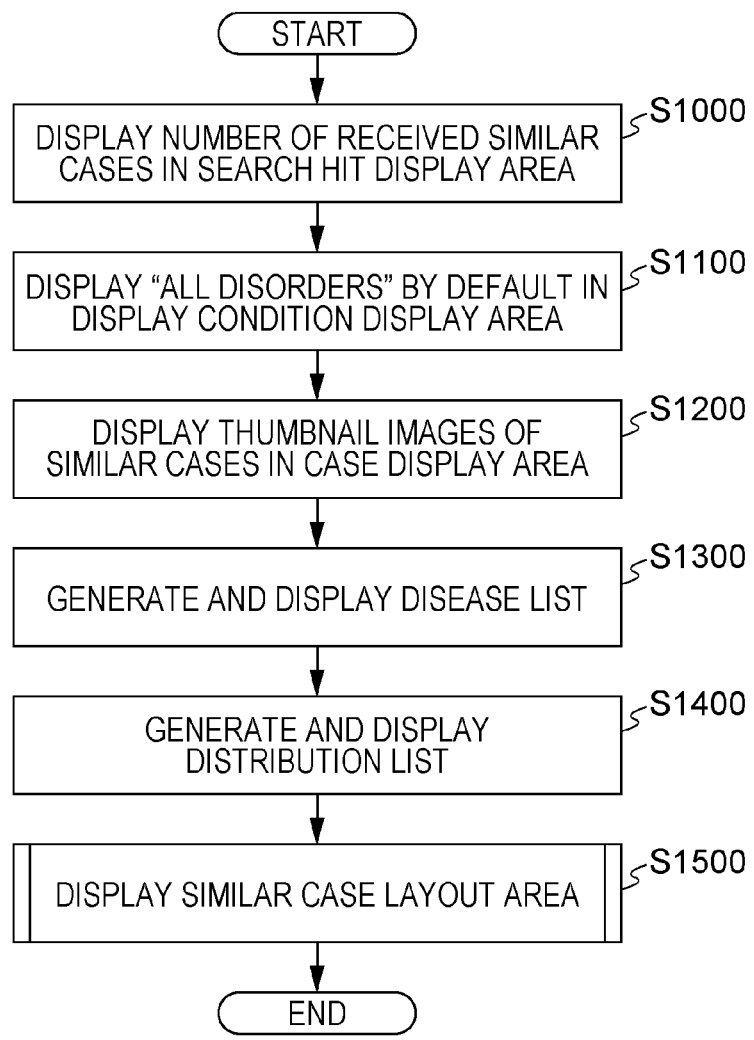
FIG. 37 is a flowchart illustrating details of a process of generating the initial basic screen illustrated in S670 of FIG. 35.

FIG. 37 is a flowchart illustrating details of a process of generating the initial basic screen K2 illustrated in S670 of FIG. 35.

First, in S1000, the display controller 104 counts the number of similar cases received in S640 of FIG. 35, and displays the count value in the search hit display area 713.

Next, in S1100, the display controller 104 displays "All Disorders" in the display condition display area 714. At this point, "All Disorders" is displayed because on the initial basic screen K2, a filter by disease or lesion distribution has not been applied by the user.

Next, in S1200, the display controller 104 displays a number of thumbnail images of similar cases in the case display area 710 equal to the number of similar cases whose thumbnail images are displayable in the case display area 710 from among the similar cases received in S640 of FIG. 35. In addition, the display controller 104 displays the definite diagnosis and the similarity in correspondence with each of the thumbnail images.

The maximum number of similar cases displayable in the case display area 710 is 20 in the example of FIG. 6. This maximum value is predetermined. Also, the maximum value may be configured to be modifiable freely by the user. If the number of similar cases received in S640 of FIG. 35 is greater than the maximum value, the display controller 104 displays the vertically elongated scrollbar 715 on the right side of the case display area 710. Consequently, the user is able to move the scrollbar 715 and view the thumbnail images of the similar cases that were hidden on the initial basic screen K2.

Next, in S1300, a disease list is generated and displayed. First, a disease list is generated from the similar cases received in S640 of FIG. 35. The disease list is a list in which the similar cases received in S640 are classified by the names of the diseases according to the definite diagnosis.

At this point, suppose that NC is the number of similar cases received in S640. The disease list manager 108 generates a disease list by using the definite diagnosis (major disease classification) 4700 and the definite diagnosis (fine disease classification) 4800 registered in each of the NC similar case data items 4000. The generated disease list is managed by the disease list manager 108 as data in a table format, as illustrated in FIG. 38.

FIG. 38 is a diagram illustrating a data structure of the disease list generated in S1300 of FIG. 37. The disease list includes "Disease ID", "Major Disease Classification", "Fine Disease Classification", "No. of Cases", and "Similar Case ID" fields. The "Disease ID" is an identifier assigned to each name of a disease according to a definite diagnosis. Herein, one disease ID is assigned to one combination of a major disease classification and a fine disease classification.

The "Major Disease Classification" is the name of the disease according to the definite diagnosis indicated by the definite diagnosis (major disease classification) 4700 registered in the similar case data 4000. The "Fine Disease Classification" is the name of the disease according to the definite diagnosis indicated by the definite diagnosis (fine disease classification) 4800 registered in the similar case data 4000. The "No. of Cases" is the number of similar cases corresponding to the name of the disease according to the definite diagnosis indicated by the "Disease ID". The "Similar Case IDs" are similar case IDs indicating similar cases corresponding to the disease indicated by the "Disease ID".

The disease list manager 108 extracts the definite diagnosis (major disease classification) 4700 and the definite diagnosis (fine disease classification) 4800 for all similar case data items 4000 received in S640, and classifies similar case data items 4000 having both of the same disease classifications as similar cases with the same disease according to the definite diagnosis. Subsequently, the disease list manager 108 counts the number of similar cases with the same disease according to the definite diagnosis, and registers the count in the "No. of Cases" field of the record for the corresponding disease according to the definite diagnosis. Additionally, the disease list manager 108 registers the similar case IDs of the similar cases classified into the same disease according to the definite diagnosis in the "Similar Case IDs" field of the record for the corresponding disease according to the definite diagnosis.

In the example of FIG. 38, the disease ID "DIS528" is assigned to the disease having the major disease classification "Neoplastic" and the fine disease classification "Lung Cancer" according to the definite diagnosis. Additionally, since there are 10 similar cases corresponding to this disease according to the definite diagnosis, 10 is registered in the "No. of Cases" field of the corresponding record, and similar case IDs such as "SIM258", "SIM551", "SIM1209", and "SIM2341" of similar cases corresponding to this disease according to the definite diagnosis are registered in the "Similar Case IDs" field of the corresponding record.

Subsequently, the display controller 104 uses the disease list generated in this way to generate and display the disease list display area 730 on the display 101.

Figure 41:
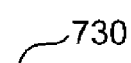
FIG. 41 is a diagram illustrating a third display example of a disease list display area.

FIGS. 39, 40, and 41 are diagrams illustrating a first display example, a second display example, and a third display example of the disease list display area 730, respectively. In the first display example as illustrated in FIG. 39, the similar cases obtained as a result of the similar case search are listed in association with the number of cases of the fine disease classification, in descending order by the number of cases.

In the second display example as illustrated in FIG. 40, the similar cases obtained as a result of the similar case search are listed in association with the number of cases of the major disease classification, in descending order by the number of cases.

In the third display example as illustrated in FIG. 41, the similar cases obtained as a result of the similar case search are listed in association with the number of cases of the major disease classification, in descending order by the number of cases, and additionally are listed in association with the fine disease classifications included in each of the major disease classifications, in descending order by the number of cases. In this case, the names of diseases according to the definite diagnosis are expressed in a hierarchical structure of a major disease classification and a fine disease classification.

Figure 42:
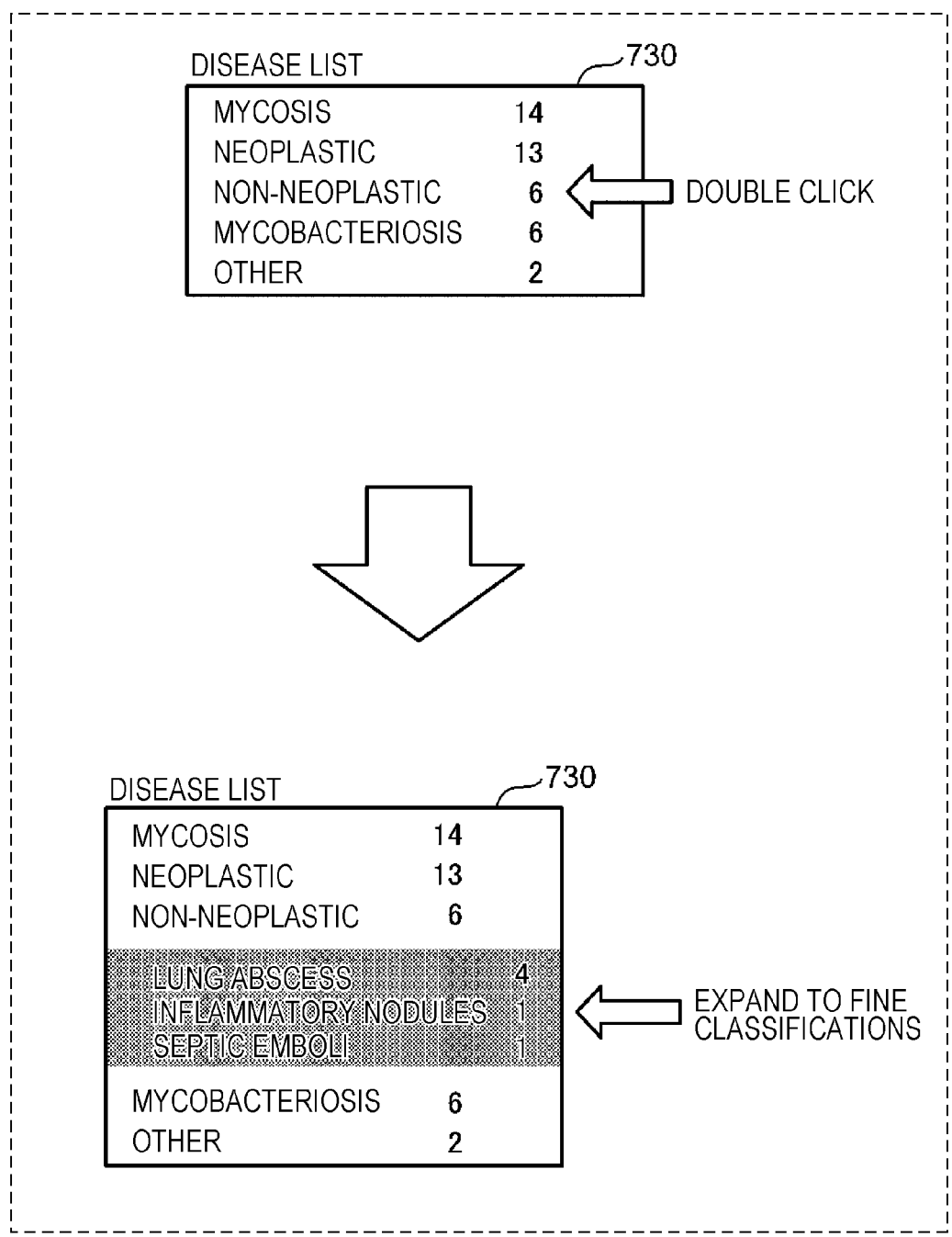
FIG. 42 is a diagram illustrating a screen transition of the disease list display area illustrated in FIG. 40.

FIG. 42 is a diagram illustrating a screen transition of the disease list display area 730 illustrated in FIG. 40. If the input controller 103 senses an operation of the user selecting one major disease classification from among the listed major disease classifications, as illustrated in the top part of FIG. 42, the display controller 104 displays the fine disease classifications belonging to the selected major disease classification in association with the number of cases in descending order, as illustrated in the bottom part of FIG. 42. At this point, the user may select a major disease classification by double-clicking or single-clicking the desired major disease classification from among the major disease classifications listed in the disease list display area 730, for example. In the example of FIG. 42, non-neoplastic has been doubled-clicked, and thus the fine disease classifications belonging to the non-neoplastic major disease classification are listed.

In the bottom part of FIG. 42, if the user double-clicks or single-clicks the area in which fine disease classifications are being listed, the display controller 104 may hide the fine disease classifications being displayed in the corresponding area.

Note that the display controller 104 may determine which fine disease classifications belong to which major disease classifications by referencing the disease list (see FIG. 38). For example, in the example of FIG. 38, since aspergillosis and cryptococcosis are associated with mycosis, the display controller 104 may determine that aspergillosis and cryptococcosis belong to mycosis.

Returning to FIG. 37, in S1400, a distribution list is generated and displayed. First, a distribution list is generated from the similar cases received in S640. The distribution list is a list in which the similar cases received in S640 are classified into respective lesion distributions.

The disease list manager 108 generates a distribution list by using the lesion distribution information 4600 registered in each of the NC similar case data items 4000. The generated distribution list is managed by the distribution list manager 109 as data in a table format, as illustrated in FIG. 43.

Figures 43, 44:
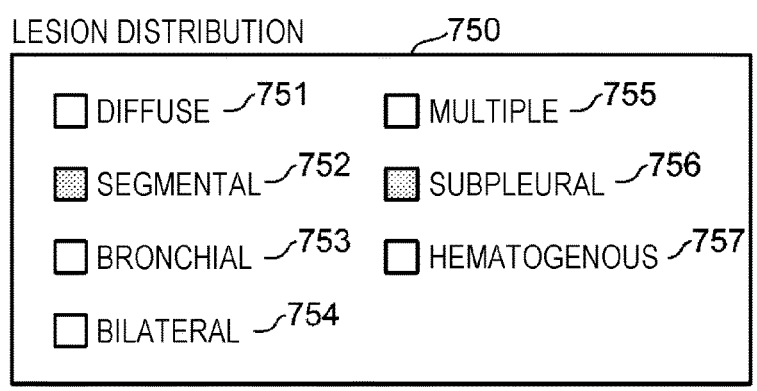
FIG. 43 is a diagram illustrating a data structure of a distribution list generated in S1400 of FIG. 37.
FIG. 44 is a diagram illustrating a distribution list display area generated using the distribution list illustrated in FIG. 43.

FIG. 43 is a diagram illustrating a data structure of the distribution list generated in S1400 of FIG. 37. The distribution list includes "Distribution Name", "No. of Cases", and "Similar Case IDs" fields. The "Distribution Name" is the names of multiple predetermined lesion distributions, such as diffuse and segmental. The "No. of Cases" is the number of similar cases corresponding to the lesion distribution. The "Similar Case IDs" are similar case IDs indicating similar cases corresponding to the lesion distribution.

The distribution list manager 109 extracts the lesion distribution information 4600 for all similar case data items 4000 received in S640, counts the number of lesion distributions for which the distribution flag value is set to 1 (applicable) in the extracted lesion distribution information 4600, and registers the count value in the "No. of Cases" of the record for the corresponding lesion distribution. Additionally, the distribution list manager 109 registers the similar case IDs of the similar cases in which the distribution flag value is set to 1 in the "Similar Case IDs" field of the record for the corresponding lesion distribution.

In the example of FIG. 43, there are three similar cases corresponding to the diffuse lesion distribution, and thus "3" is registered in the "No. of Cases" field of the record for "Diffuse". Also, the similar case IDs "SIM2521", "SIM4123", and "SIM5225" of similar cases corresponding to the diffuse lesion distribution are registered in the "Similar Case IDs" field of the record for "Diffuse".

Subsequently, the display controller 104 uses the distribution list generated in this way to generate and display the distribution list display area 750 on the display 101.

FIG. 44 is a diagram illustrating the distribution list display area 750 generated using the distribution list illustrated in FIG. 43. In FIG. 43, since the number of segmental and subpleural cases is 0, in FIG. 44, Segmental 752 and Subpleural 756 are displayed in an inactive state, whereas since the number of cases is at least 1 for the other lesion distributions, the other lesion distributions are displayed in an active state.

Returning to FIG. 37, in S1500, the layout area 720 is displayed. This process is conducted by the display controller 104.

Figure 45:
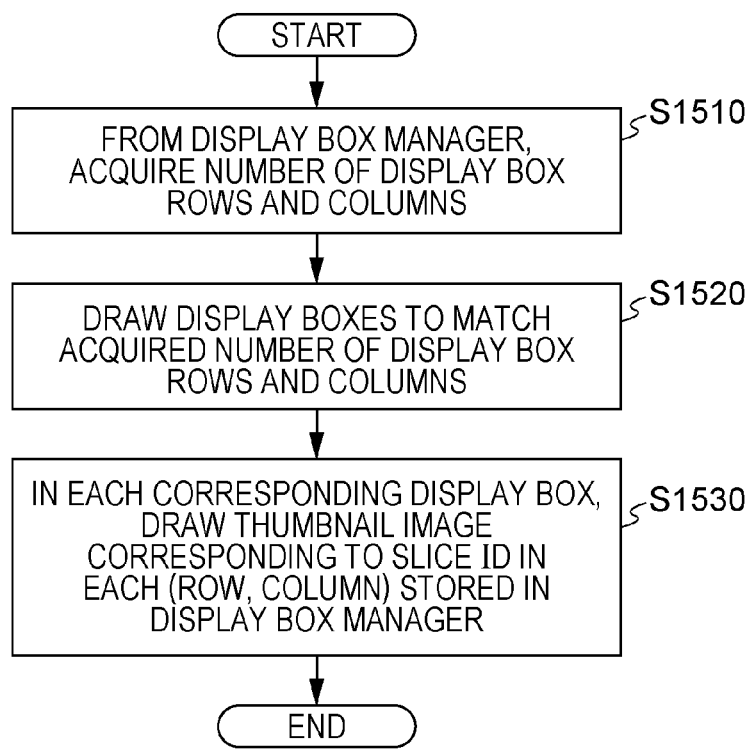
FIG. 45 is a flowchart illustrating the process of S1500 illustrated in FIG. 37.

FIG. 45 is a flowchart illustrating the process of S1500 illustrated in FIG. 37. In S1510, the display controller 104 acquires, from the display box management information 4410 set in S660, the number of rows and the number of columns of the display boxes constituting the layout area 720. In the example of the display box management information 4410 in FIG. 36, the number of rows and the number of columns are set to 2×2, and thus the information "2×2" is acquired.

Next, in S1520, the display controller 104 draws display boxes matching the number of rows and the number of columns of display boxes acquired in S1510.

Finally, in S1530, the display controller 104 specifies the slice ID of each display box from the display box management information 4410, and draws the thumbnail image corresponding to each specified slice ID inside each corresponding display box.

In the example of FIG. 36, the slice ID of the case to be diagnosed is stored in the display box in the first row and first column. For this reason, the display controller 104 generates a thumbnail image from the slice image of the case to be diagnosed transmitted in S600 of FIG. 30, and draws the generated thumbnail image (search query image) in the display box 721.

At this stage, slice IDs are not stored in the remaining display boxes (the display boxes in row 1 column 2, row 2 column 1, and row 2 column 2, respectively), and thus the display controller 104 does not display anything in these display boxes.

Returning to FIG. 35, the communication controller 110 transmits the display box management information 4410 stored in the display box manager 106 to the display controller 104 (S680).

Next, the display controller 104 launches medical image viewers in the same display state and layout as the display state and layout of the layout area 720 (S690).

(Search Query Image Insertion Process Flow)

Next, the process of inserting the search query image into the case display area 710 described using FIGS. 8 to 13 will be described.

Figure 46:
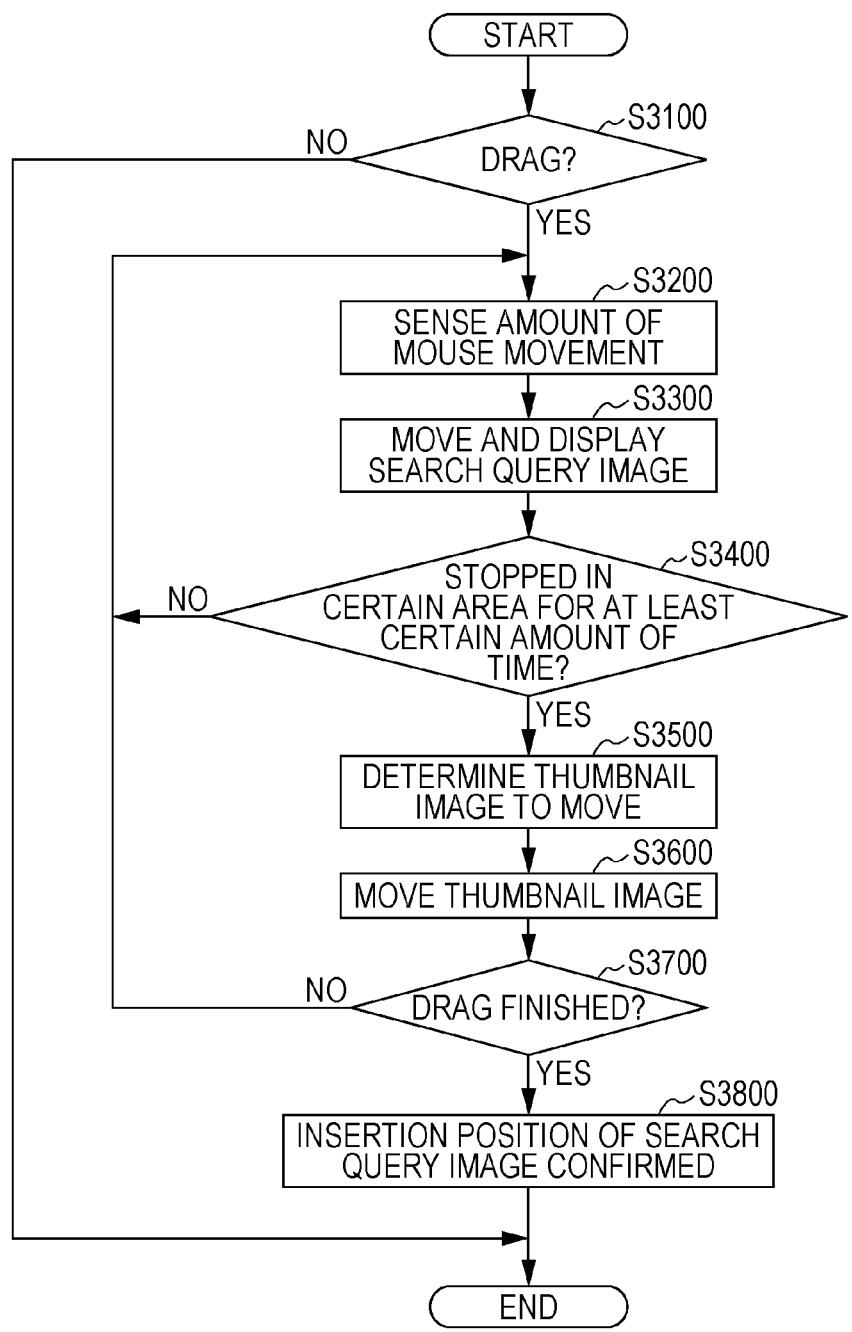
FIG. 46 is a flowchart illustrating an example of a process of inserting a search query image in among thumbnail images being displayed in a case display area.

FIG. 46 is a flowchart illustrating an example of a process of inserting the search query image into the case display area 710.

In S3100, the input controller 103 senses whether or not the mouse of the operating unit 102 is dragging the search query image being displayed in the layout area 720. In other words, the input controller 103 receives a signal output from the operating unit 102, and if a drag operation is being conducted in which the left button of the mouse is on when the mouse pointer is positioned over the search query image in the layout area 720 and the mouse is being moved while in this state (S3100, Yes), the process proceeds to S3200. If a drag is not being conducted (S3100, No), the process ends.

In S3200, the input controller 103 senses the amount of movement of the mouse operated by the user. Additionally, the input controller 103 outputs the sensed amount of mouse movement to the display controller 104.

In S3300, the display controller 104 moves and displays the search query image in the case display area 710 according to the amount of mouse movement. As illustrated in FIG. 8, the display controller 104 determines the position at which to display the search query image based on the amount of mouse movement input from the input controller 103, and displays the search query image as an overlay on top of the case display area 710.

In S3400, the input controller 103 determines whether or not the mouse pointer 801 (see FIG. 9) has stopped in a certain area of the case display area 710 for a certain amount of time or more. If the mouse pointer 801 has stopped inside a certain area for a certain amount of time or more (S3400, Yes), the process proceeds to S3500. Otherwise (for example, if the mouse pointer 801 is moving without stopping) (S3400, No), the process returns to S3200. Herein, the certain area refers to the display area 701 of a thumbnail image (see FIG. 7), for example. Note that an enlarged area around the display area 701 may also be used as the certain area, insofar as the enlarged area does not overlap with an adjacent thumbnail image.

In S3500, the input controller 103 determines the thumbnail image to move from the position of the mouse pointer 801 (see FIG. 9). In other words, as illustrated in FIG. 9, for example, the input controller 103 acquires the positional coordinates of the mouse pointer 801, and acquires the similar case ID of the thumbnail image at the position of the mouse pointer 801 (in FIG. 9, the similar case ID of the thumbnail image 710a). Furthermore, the input controller 103 acquires the similar case ID of the thumbnail image to move from the similar case ID at the position of the mouse pointer 801 and the number of displayed thumbnail images in the case display area 710 (in FIG. 9, the similar case ID of the thumbnail image 710a and the similar case ID of the thumbnail image 710b). The input controller 103 outputs to the display controller 104 the acquired similar case ID of the thumbnail image to move.

In S3600, the display controller 104 moves the thumbnail images of the similar case IDs input from the input controller 103 in S3500. The display controller 104 shifts the thumbnail image to move by the space of one thumbnail image in the case display area 710 to the right. At this point, if the thumbnail images are moved instantaneously by the space of one thumbnail image, the user may have difficulty grasping the positional relationships of the thumbnail images before and after insertion. For this reason, as illustrated in FIGS. 8 to 10, the display controller 104 gradually and smoothly varies the display positions of the thumbnail images.

At this point, in the present embodiment, in S3600, the display controller 104 does not move thumbnail images across rows when moving the thumbnail images in the case display area 710. In other words, as illustrated in FIG. 9, when the search query image 802 is inserted into the case display area 710, the display controller 104 does not display in the case display area 710 the thumbnail image 710b of the similar case adjacent to the right edge of the case display area 710. Consequently, in the present embodiment, the positional relationships of thumbnail images on rows other than the row where the search query image is inserted stay the same before and after the insertion of the search query image.

In S3700, the input controller 103 senses whether or not the drag by the mouse has finished, and determines whether or not the user has confirmed the insertion position of the search query image. The input controller 103 senses the on-off state of the left button of the mouse, for example. If the drag by the mouse (with the left button on) is still ongoing (S3700, No), the process returns to S3200. On the other hand, if the drag has finished (S3700, Yes), it is determined that the user has confirmed the insertion position of the search query image, and the process proceeds to S3800.

In S3800, the display controller 104 determines that the user has confirmed the insertion position of the search query image, inserts and displays the search query image at the position of the thumbnail image that was moved, and the process ends. Note that after the search query image is inserted completely, the display controller 104 completely removes from the case display area 710 the thumbnail image 710b (see FIG. 9) that had been displayed adjacent to the right edge of the case display area 710, as illustrated in FIG. 10.

Figure 47:
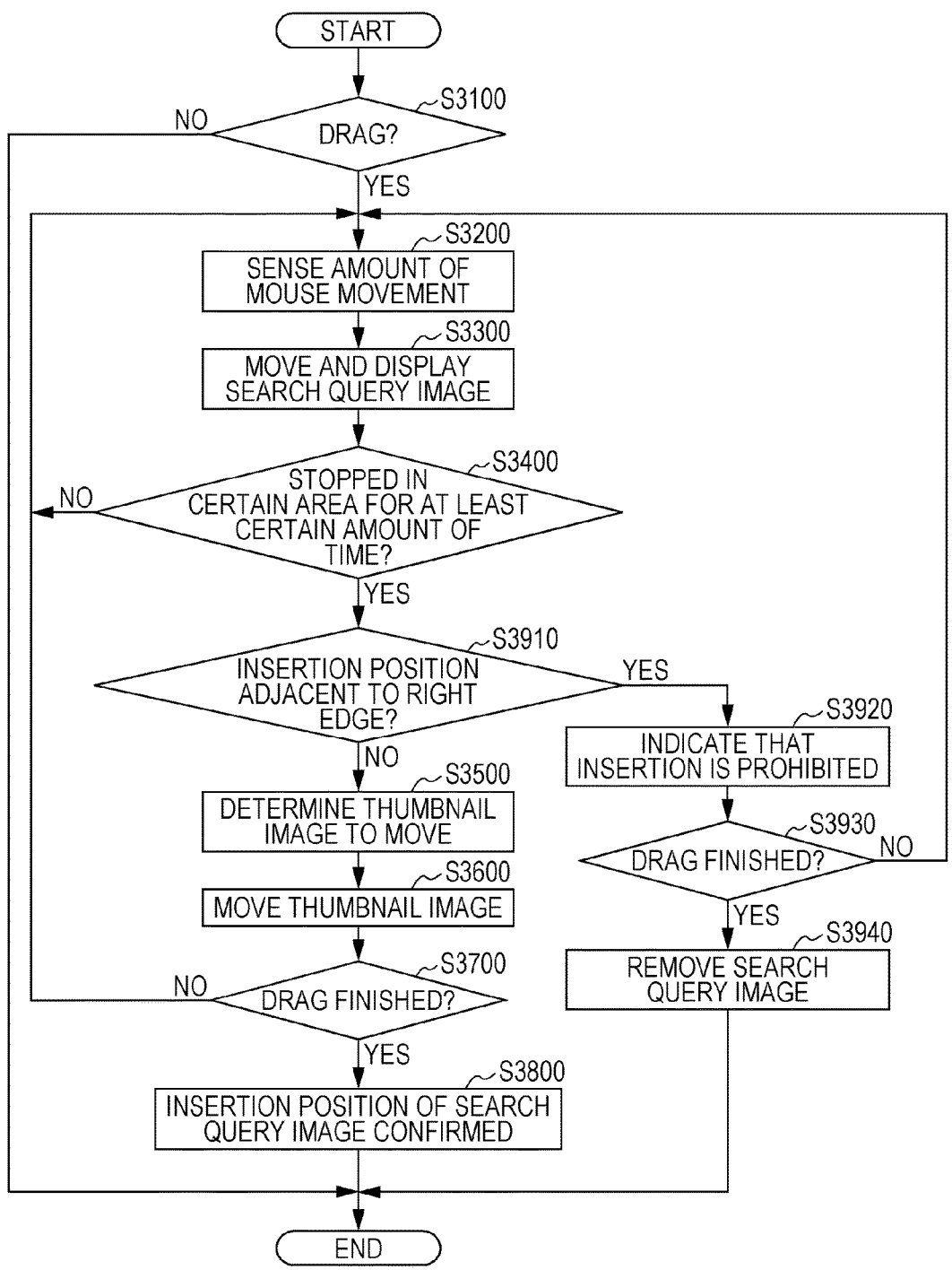
FIG. 47 is a flowchart illustrating a different example from FIG. 46 of a process of inserting a search query image in among thumbnail images being displayed in a case display area.

FIG. 47 is a flowchart illustrating a different example from FIG. 46 of a process of inserting the search query image in among the thumbnail images being displayed in case display area 710. In FIG. 47, the search query image is not allowed to be inserted when the insertion position of the search query image is adjacent to the right edge of the case display area 710, as described using FIG. 12.

S3100 to S3400 are the same as S3100 to S3400 of FIG. 46. If the mouse pointer 801 has stopped inside a certain area for a certain amount of time or more (S3400, Yes), the process proceeds to S3910.

In S3910, the input controller 103 determines whether or not the insertion position of the search query image (that is, the thumbnail image corresponding to the position of the mouse pointer 801) is adjacent to the right edge of the case display area 710.

If the thumbnail image corresponding to the position of the mouse pointer 801 is not adjacent to the right edge of the case display area 710 (S3910, No), the process proceeds to S3500. S3500 to S3800 are the same as S3500 to S3800 of FIG. 46. On the other hand, if the thumbnail image corresponding to the position of the mouse pointer 801 is adjacent to the right edge of the case display area 710 (S3910, Yes), the process proceeds to S3920.

In S3920, the display controller 104 displays the thick frame 804 around the thumbnail image 710b as illustrated in FIG. 12, for example, thereby indicating that the insertion of the search query image is prohibited.

In S3930, the input controller 103 senses whether or not the drag by the mouse has finished, and thereby determines whether or not the user has confirmed the insertion position of the search query image. The input controller 103 senses the on-off state of the left button of the mouse. If the drag by the mouse (with the left button on) is still ongoing (S3930, No), the process returns to S3200. On the other hand, if the left button of the mouse has been switched off and the drag has finished (S3930, Yes), it is determined that the user has confirmed the insertion position of the search query image, and the process proceeds to S3940.

In S3940, the display controller 104 removes the search query image being displayed in the case display area 710, and the process ends. Note that since the search query image is still being displayed in the layout area 720, the user is able to conduct an operation of inserting the search query image at another position by subsequently dragging the search query image with the mouse again.

In the description of the "Search query image insertion process flow" section above, the "search query image" may also be construed as "the thumbnail image of the search query image".

(Distribution List Selection)

Next, a process when a lesion distribution displayed in the distribution list display area 750 illustrated in FIGS. 18, 20, and 22 is selected will be described.

Figure 48:
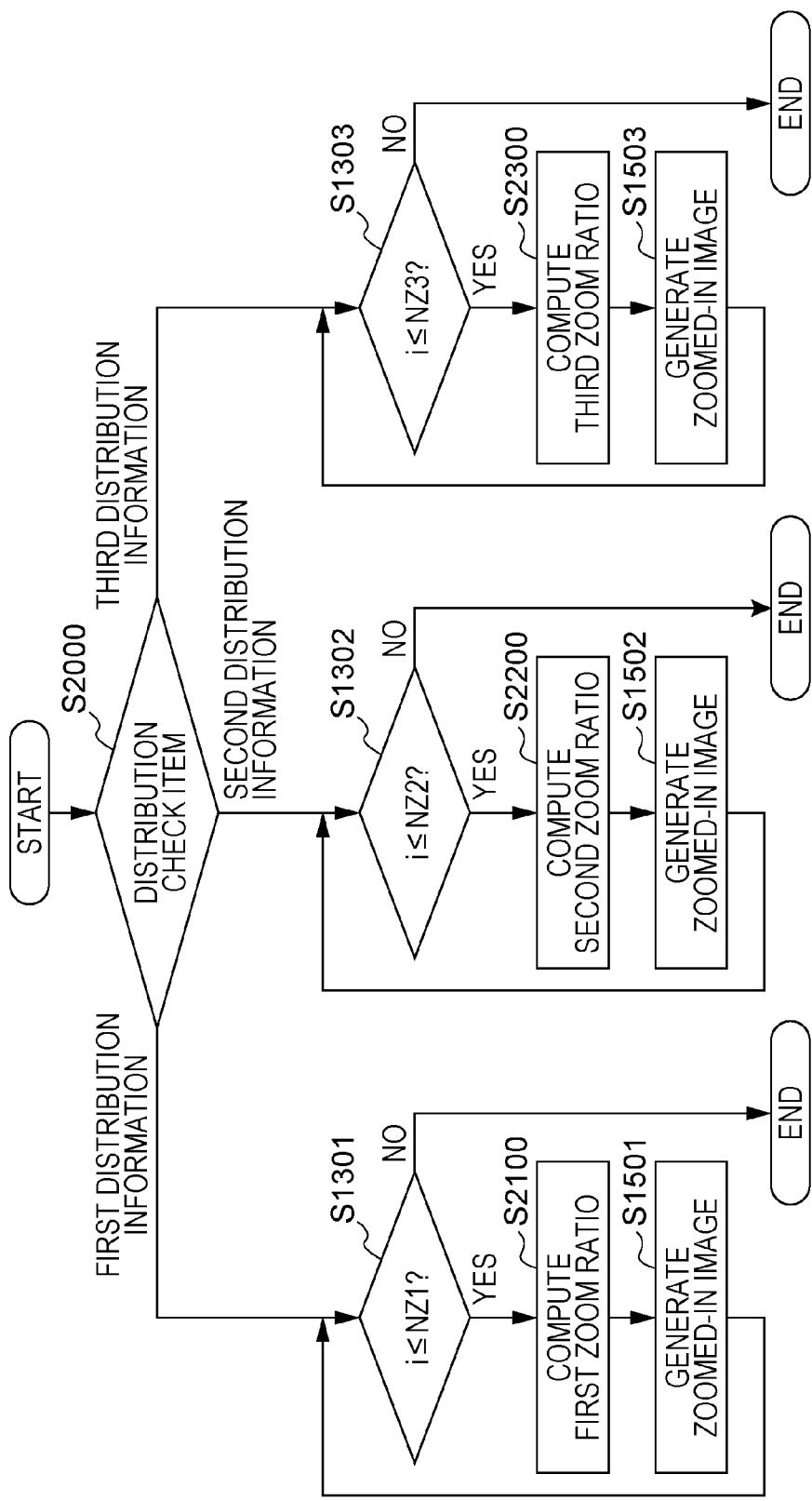
FIG. 48 is a flowchart illustrating a process when a lesion distribution displayed in a distribution list display area is selected.

FIG. 48 is a flowchart illustrating a process when a lesion distribution displayed in the distribution list display area 750 is selected.

In S2000, if the input controller 103 senses an operation of selecting any one distribution check item from among the lesion distributions (distribution check items) displayed in the distribution list display area 750, the display controller 104 determines whether the sensed distribution check item corresponds to first, second, or third distribution information. In the case of the first distribution information, the process proceeds to S1301, while in the case of the second distribution information, the process proceeds to S1302, and in the case of the third distribution information, the process proceeds to S1303.

The first distribution information is information for selecting, from among the thumbnail images of similar cases listed in the case display area 710, a thumbnail image in which the size of the region of interest belongs to a certain first range indicating a wide range of the lung region. Herein, the first distribution information corresponds to "Bilateral", "Multiple", "Diffuse", and "Hematogenous". Thus, for the first range, a value range is adopted so that the size of the region of interest set when diagnosing these lesion distributions belongs to that value range.

The second distribution information is information for selecting, from among the thumbnail images of similar cases listed in the case display area 710, a thumbnail image in which the size of the region corresponding to the region of interest belongs to a certain second range (lower than the first range; the upper limit value of the second range is less than or equal to the lower limit value of the first range) indicating a partial lung region. Herein, the second distribution information corresponds to "Bronchial" and "Segmental". Thus, for the second range, a value range is adopted so that the size of the region of interest set when diagnosing these lesion distributions belongs to that value range.

The third distribution information is information for selecting, from among the thumbnail images of similar cases listed in the case display area 710, a thumbnail image in which the region of interest includes the pleura. Herein, the third distribution information corresponds to "Subpleural".

In S1301, the display controller 104 extracts, in order of highest similarity, a number of similar cases less than or equal to the maximum number of displayable thumbnail images in the case display area 710 (in the present embodiment, 20 cases) from among the similar cases obtained by a similar case search, which are similar cases of the lesion distribution selected by the user as the first distribution information. The display controller 104 determines the number of extracted similar cases as a number NZ1 of similar cases to zoom. Subsequently, the display controller 104 sets the thumbnail image of the extracted similar case i (where i is an integer equal to or greater than 1 that serves as an index specifying an extracted similar case) as the thumbnail image to process. Subsequently, the display controller 104 repeats the processes of S2100 and S1501 until i reaches NZ1. Every time the processes of S2100 and S1501 are executed, the display controller 104 increments the index i by 1. When i exceeds NZ1 (S1301, No), the process ends.

In S2100, the display controller 104 computes a first zoom ratio corresponding to the first distribution information for the similar case i. Herein, 1.0 is adopted as the first zoom ratio, for example. However, this is merely one example, and a zoom ratio other than 1.0 may also be adopted as the first zoom ratio, insofar as the zoom ratio is a value by which the entirety of the region of interest set when diagnosing a lesion distribution indicated by the first distribution information is contained in the display area.

In S1501, the display controller 104 displays, in the case display area 710, the thumbnail image of the similar case i zoomed in by the first zoom ratio of the similar case i.

In FIG. 19 discussed earlier, bilateral is selected. In this case, only the thumbnail images of similar cases whose lesion distribution corresponds to bilateral from among the similar cases are displayed in the case display area 710. Also, in this case, since the zoom ratio is 1.0, in the case display area 710, thumbnail images are displayed in the same display mode as the thumbnail images displayed immediately after the similar case search results are obtained. In other words, the display positions of the thumbnail images are not adjusted so that the center of the region of interest ROI is positioned in the center of the display area 6801, and the thumbnail images are also displayed without being zoomed in.

In S1302, the display controller 104 extracts, in order of highest similarity, a number of similar cases less than or equal to the maximum number of displayable thumbnail images in the case display area 710 from among the similar cases obtained by a similar case search, which are similar cases of the lesion distribution selected by the user as the second distribution information. The display controller 104 determines the number of extracted similar cases as a number NZ2 of similar cases to zoom. Subsequently, the display controller 104 sets the thumbnail image of the extracted similar case i as the thumbnail image to process. Subsequently, the display controller 104 repeats the processes of S2200 and S1502 until i reaches NZ2. Every time the processes of S2200 and S1502 are executed, the display controller 104 increments the index i by 1. When i exceeds NZ2 (S1302, No), the process ends.

In S2200, the display controller 104 uses the predetermined size of the display area for one thumbnail image in the case display area 710 and the region of interest information for the similar case i to compute a second zoom ratio corresponding to the second distribution information for the similar case i.

When the second distribution information is selected, the display controller 104 zooms in the similar case i so that the size of the region of interest is approximately ½ the size of the display area. For this reason, the display controller 104 calculates a second zoom ratio ki for the similar case i according to the following formula. Provided that Sd is the surface area of the display area, and Si is the surface area of the region of interest in the thumbnail image of the similar case i to be zoomed in, the second zoom ratio ki may be computed as follows.

$$ki = \tfrac{1}{2}(Sd/Si)$$

In S1502, the display controller 104 zooms in the thumbnail image of the similar case i by the second zoom ratio ki, and displays the thumbnail image in the case display area 710 so that the center of the region of interest in the thumbnail image is positioned in the center of the display area.

In FIG. 21 discussed earlier, bronchial is selected. In this case, only the thumbnail images of similar cases whose lesion distribution corresponds to bronchial from among the similar cases are displayed in the case display area 710. Also, in the case display area 710, all thumbnail images are zoomed in by the second zoom ratio so that the center of the region of interest ROI is positioned in the center of the display area 6901.

In S1303, the display controller 104 extracts, in order of highest similarity, a number of similar cases less than or equal to the maximum number of displayable thumbnail images in the case display area 710 from among the similar cases obtained by a similar case search, which are similar cases of the lesion distribution selected by the user as the third distribution information. The display controller 104 determines the number of extracted similar cases as a number NZ3 of similar cases to zoom. Subsequently, the display controller 104 sets the thumbnail image of the extracted similar case i as the thumbnail image to process. Subsequently, the display controller 104 repeats the processes of S2300 and S1503 until i reaches NZ3. Every time the processes of S2300 and S1503 are executed, the display controller 104 increments the index i by 1. When i exceeds NZ3 (S1303, No), the process ends.

In S2300, the display controller 104 uses the predetermined size of the display area for one thumbnail image in the case display area 710, the region of interest information for the similar case i, and pleural region information 4900 to compute a third zoom ratio corresponding to the third distribution information for the similar case i.

FIG. 49 is a diagram illustrating a data structure of similar case data 4000 with added pleural region information 4900. Note that if the pleural region information 4900 is not registered in the similar case data 4000, the pleural region information 4900 is not obtained. In this case, the display controller 104 may set the third zoom ratio to the same value as the first zoom ratio, namely, 1.0. Herein, the pleural region information 4900 is information indicating the pleural region in a similar case.

In S1503, the display controller 104 zooms in the thumbnail image of the similar case i by the third zoom ratio ki, and displays the zoomed-in thumbnail image in the case display area 710 so that the center of the region of interest in the thumbnail image is positioned in the center of the display area.

Figure 50:
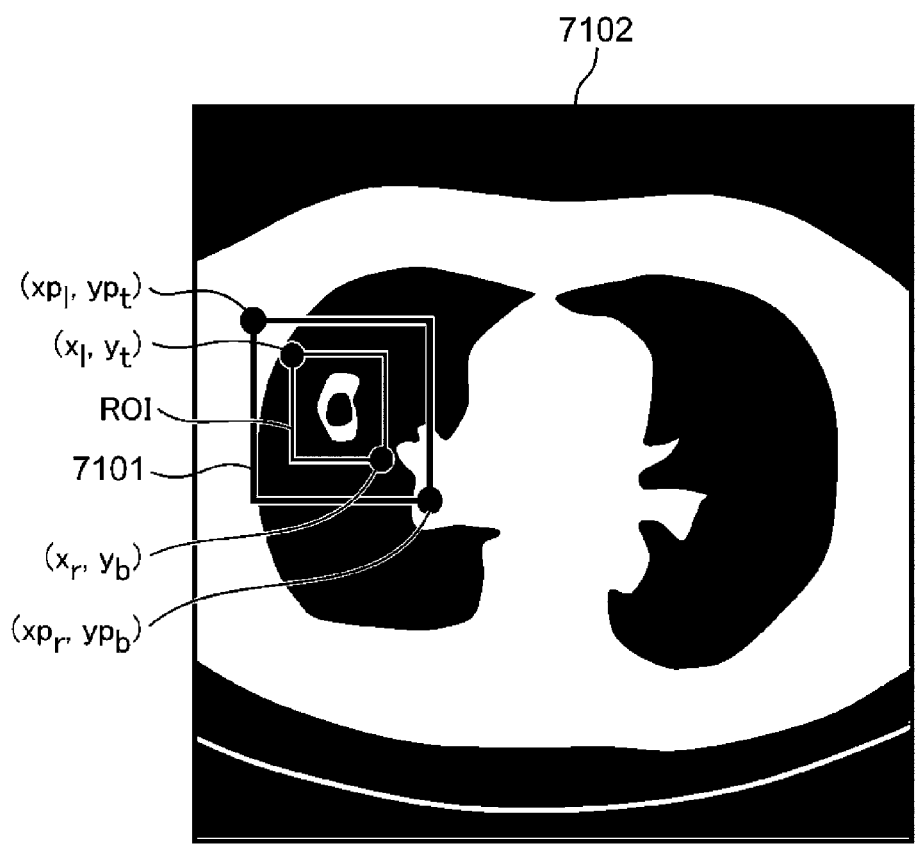
FIG. 50 is a diagram explaining a pleural area.

FIG. 50 is a diagram explaining a pleural region 7101. As illustrated in FIG. 50, the pleural region 7101 is a region including the pleura, and is a rectangular region whose center is positioned at the center of the region of interest ROI, and which is slighter larger in size than the region of interest ROI. Herein, the pleural region information 4900 includes four values: the coordinates of the top-left vertex ($xp_l$, $yp_t$), and the coordinates of the bottom-right vertex ($xp_r$, $yp_b$) of the pleural region 7101. When the third distribution information is selected, the pleural region is zoomed in, and thus the display controller 104 calculates the third zoom ratio ki according to the following formula. Provided that Sd is the surface area of the display area 7102 and Sp is the surface area of the pleural region 7101, the third zoom ratio ki may be computed as follows.

$$ki = Sd/Sp$$

Note that the pleural region information 4900 may also be input by the user together with the region of interest information when creating the similar case data 4000. Alternatively, the pleural region information 4900 may be created automatically by having an image processing device automatically extract the lung region from a slice image and determine the pleural position.

In FIG. 23 discussed earlier, subpleural is selected. In this case, only the thumbnail images of similar cases whose lesion distribution corresponds to subpleural from among the similar cases are displayed in the case display area 710. Also, in the case display area 710, all thumbnail images are zoomed in by the third zoom ratio so that the center of the region of interest ROI is positioned in the center of the display area 7001.

According to the above process, in the case display area 710, thumbnail images are displayed at a zoom ratio reflecting the diagnosis details related to the lesion distribution. Additionally, in the case display area 710, thumbnail images are displayed with consistent sizes of the region of interest. For this reason, since similar medical images having small regions of interest are zoomed in, it is possible to prevent situations in which such regions of interest are overlooked, thereby improving diagnosis accuracy. Furthermore, since the zoom process is conducted only on similar cases displayed in the case display area 710, and not on all similar cases obtained as the similar case search results, the load on the system is greatly reduced.

Advantageous Effects

As above, in the present embodiment, the display controller 104 inserts and displays the search query image at a user-specified position in the case display area 710. Additionally, in conjunction with this insertion operation, the display controller 104 moves the thumbnail image of the similar case that was being displayed at the insertion position, and displays the search query image adjacent to a thumbnail image of a similar case that the user wants to compare to the search query image.

For this reason, there are no other thumbnail images between the search query image and the thumbnail image to be compared to the search query image. Consequently, the movement of the physician's gaze is decreased. For this reason, the physical burden associated with shifting one's gaze back and forth when making a detailed comparison of many characteristics such as the position, size, shape, and distribution of shadows may be reduced.

Furthermore, the physician is able to narrow down the thumbnail images to reference from among the multiple thumbnail images displayed in the case display area 710 while moving the search query image around inside the case display area 710. As a result, at the stage before making a detailed determination, or in other words, at the thumbnail image stage, the physician is able to make a simple determination, such as whether or not the shadow in the thumbnail image 710a resembles the shadow in the search query image 802, for example.

As a result, in the stage before making a detailed determination (in other words, the stage in which thumbnail images are being displayed), the accuracy of selecting final candidates may be raised. For this reason, it is possible to improve the diagnosis accuracy when subsequently making a detailed determination. In addition, the physician is able to select the similar cases to serve as final candidates while in the stage of thumbnail images which have less information compared to the original images. Consequently, the time and effort of making a detailed determination of the similarity between the medical image to be interpreted and similar cases by using original images may be omitted, and the similar cases to serve as the final candidates may be extracted efficiently. Note that in the description of the "Advantageous effects" section above, the "search query image" may also be construed as "the thumbnail image of the search query image".

Modified Embodiment

In the foregoing embodiment, an example of the case search system 300 extracting image features is illustrated, but the information terminal 100 may also extract image features.

Figure 51:
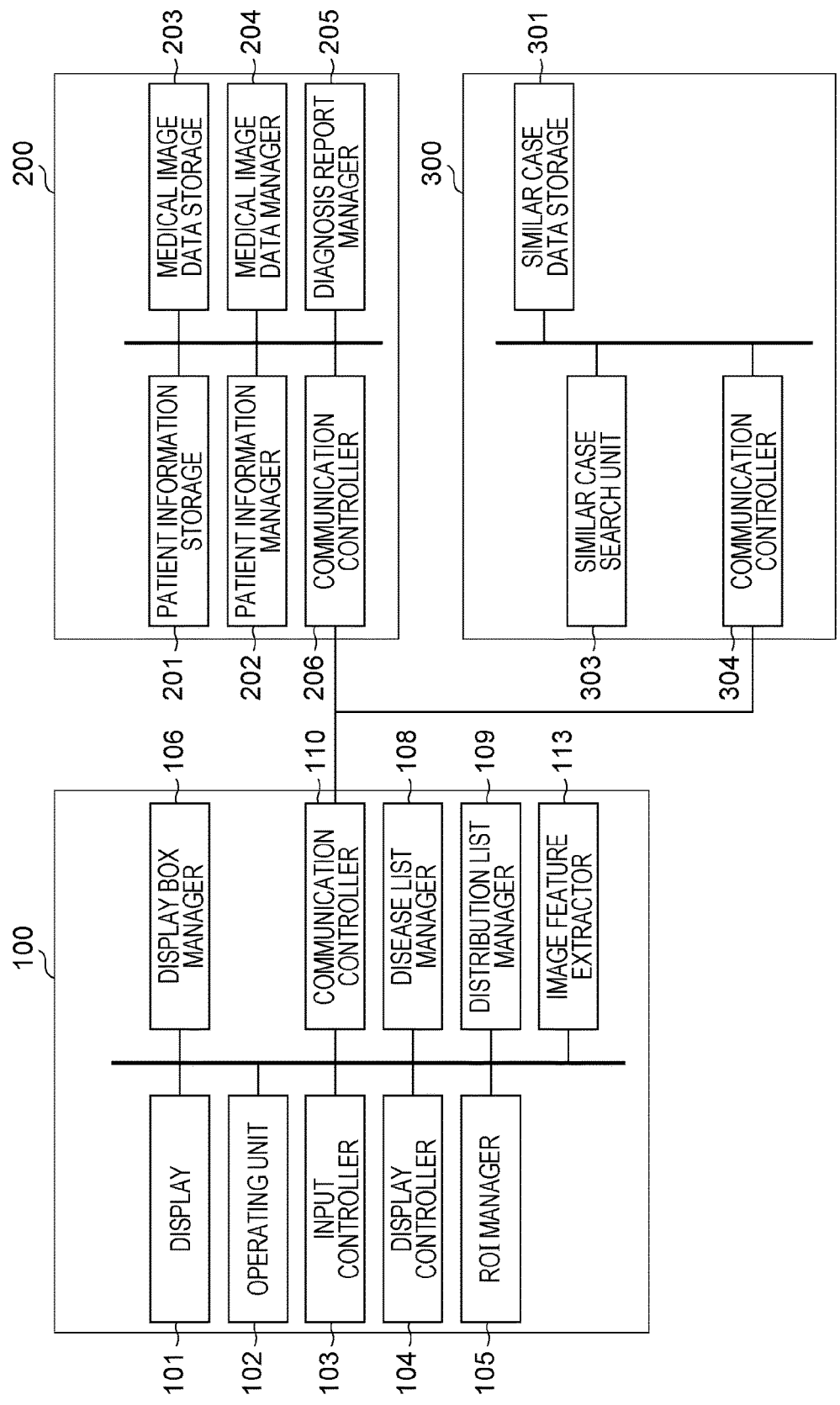
FIG. 51 is a block diagram of an information terminal, a medical information management system, and a case search system in a case of adopting an aspect in which the information terminal extracts image features.

FIG. 51 is a block diagram of the information terminal 100, the medical information management system 200, and the case search system 300 in a case of adopting an aspect in which the information terminal 100 extracts image features.

FIG. 51 differs from FIG. 2 in that an image feature extractor 113 has been added to the information terminal 100, and the image feature extractor 302 has been omitted from the case search system 300.

Figure 52:
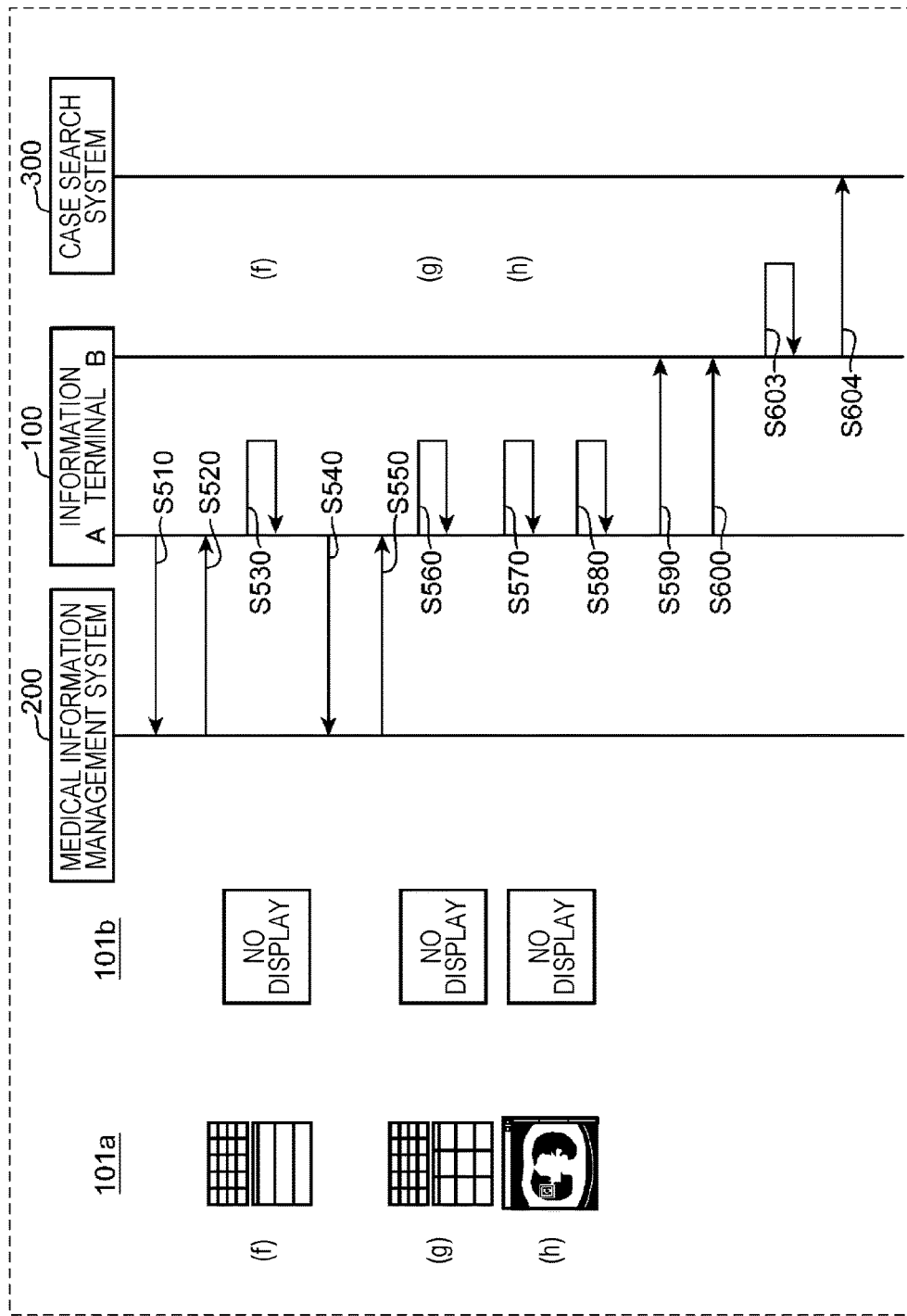
FIG. 52 is a sequence diagram illustrating a process in which an information terminal acquires a case to be diagnosed from a medical information management system, and a case search system receives a similar case search request.

FIG. 52 is a sequence diagram illustrating a process in which the information terminal 100 acquires a case to be diagnosed from the medical information management system 200, and the case search system 300 receives a similar case search request.

FIG. 52 differs from FIG. 30 in that, after the process of the ROI manager 105 transmitting the slice image of the case to be diagnosed to the communication controller 110 (S600), image feature extraction is conducted on the information terminal 100 (S603), and the extracted image features are transmitted to the case search system 300 (S604). The processing details of the image feature extraction (S604) is similar to the case in which image feature extraction is conducted on the case search system 300.

FIG. 53 is a sequence diagram illustrating a process in which the case search system 300 receives a similar case search request, and replies to the information terminal 100 with similar case search results. FIG. 53 differs from FIG. 35 in that, since the image feature extraction is conducted on the information terminal 100, the image feature extraction (S610) illustrated in FIG. 35 is omitted from FIG. 53.

The present disclosure may be utilized in devices such as a similar case search device that presents similar cases that serve as a reference when making a diagnosis using a medical image to be interpreted, as well as a radiological interpretation educational device for medical trainees studying radiological interpretation.

What is claimed is:

1. A control method for an information terminal, the control method being executed by a computer of the information terminal, and the control method comprising:
   receiving thumbnail images of a plurality of medical images from a case search system, each of the plurality of medical images being received based on a similarity to a target medical image to be interpreted, the plurality of medical images being respectively obtained from a plurality of original images;
   displaying a target thumbnail image of the target medical image and the received thumbnail images on a display screen of a display, the display screen including (i) a first display area that displays the target thumbnail image and (ii) a second display area that displays the received thumbnail images including a first thumbnail image and a second thumbnail image, the first thumbnail image and the second thumbnail image being displayed adjacent to each other in the second display area;
   detecting a first operation of moving the target thumbnail image to an area between the first thumbnail image and the second thumbnail image in the second display area; and
   after the detecting the first operation, (i) moving the second thumbnail image in the second display area and (ii) displaying the target thumbnail image in the second display area between the first thumbnail image and the second thumbnail image,
   wherein resolutions of the received thumbnail images are lower than resolutions of the plurality of medical images, and a resolution of the target thumbnail image is lower than a resolution of the target medical image,
   the received thumbnail images includes a third thumbnail image,
   a shape of the second display area is rectangular,
   a number of images displayed horizontally in the second display area is fixed,
   in the second display area, the first thumbnail image, the second thumbnail image, and the third thumbnail image are displayed adjacent to each other in order from left to right on a same row, the third thumbnail image is displayed adjacent to a right edge of the second display area, the displaying the target thumbnail image in the second display area between the first thumbnail image and the second thumbnail image after the detecting the first operation includes removing the third thumbnail image from the second display area without displaying the third thumbnail image on the display screen, and the control method further comprises:

detecting a second operation of moving the target thumbnail image to an area between the second thumbnail image and the third thumbnail image in the second display area; and after the detecting the second operation, (i) removing the third thumbnail image from the second display area without displaying the third thumbnail image on the display screen and (ii) displaying the target thumbnail image in the second display area adjacent to the right edge of the second thumbnail image.

2. The control method according to claim 1, wherein the similarity between each of the plurality of medical images and the target medical image is based on (i) a distance between a feature vector obtained from the corresponding original image and a feature vector of a region of interest in the target medical image or (ii) a cosine similarity between the corresponding original image and the target medical image.

3. The control method according to claim 2, wherein the target thumbnail image is displayed in an emphasized state in the second display area compared to the received thumbnail images.

4. The control method according to claim 2, wherein in the second display area, display sizes of the target thumbnail image, the first thumbnail image, and the second thumbnail image are set to a same size.

5. The control method according to claim 2, further comprising:

detecting specifying information indicating the region of interest in the target medical image; and transmitting information indicating features of the region of interest to the case search system.

6. The control method according to claim 2, wherein the target medical image is a medical image of lungs, each of the plurality of medical images is a medical image of lungs, and includes a corresponding region of interest indicating an affected area, the display screen displays first distribution information for selecting, from among the plurality of medical images, medical images in which a size of the corresponding region of interest belongs to a first category, second distribution information for selecting, from among the plurality of medical images, medical images in which the size of the corresponding region of interest belongs to a second category smaller than the first category, and third distribution information for selecting, from among the plurality of medical images, medical images in which the corresponding region of interest includes pleura, and the control method further comprising detecting an operation of selecting any one of the first distribution information, the second distribution information, and the third distribution information, and displaying the thumbnail images of the medical images corresponding the selected distribution information in the second display area.

7. The control method according to claim 6, wherein the second display area includes a plurality of individual areas for respectively displaying each of the received thumbnail images, the control method further comprising detecting an operation of selecting the first distribution information, and respectively displaying each of the thumbnail images of the medical images corresponding to the first distribution information in the individual areas, the thumbnail images being displayed at an initial size.

8. The control method according to claim 6, wherein the first distribution information is information indicating a distribution belonging to a bilateral, a multiple, a diffuse, or a hematogenous category, the second distribution information is information indicating a distribution belonging to a segmental or a bronchial category, and the third distribution information is information indicating a distribution belonging to a subpleural category.

9. The control method according to claim 6, the second display area includes a plurality of individual areas for respectively displaying each of the received thumbnail images, the control method further comprising detecting an operation of selecting the second distribution information, and respectively displaying each of the thumbnail images of the medical images corresponding to the second distribution information in the individual areas, and the corresponding region of interest in each of the displayed medical images is enlarged and centered.

10. The control method according to claim 6, the second display area includes a plurality of individual areas for respectively displaying each of the received thumbnail images, the control method further comprising detecting an operation of selecting the third distribution information, and respectively displaying each of the thumbnail images of the medical images corresponding to the third distribution information in the individual areas, the thumbnail images being displayed in pleura, and the corresponding region of interest in each of the displayed medical images is enlarged and centered.

11. The control method according to claim 2, wherein the similarity between the plurality of medical images and the target medical image is based on, for each of the plurality of medical images, the distance between the feature vector obtained from the corresponding original image and the feature vector or a region of interest in the target medical image.

12. The control method according to claim 2, wherein the similarity between the plurality of medical images and the target medical image is based on, for each of the plurality of medical images, the cosine similarity between the corresponding original image and the target medical image.

13. The control method according to claim 1, wherein a scroll element is displayed on the display screen, and the control method further comprising detecting an operation performed using the scroll element, and scrolling, in the second display area, a row including the first thumbnail image and the target thumbnail image.

14. A non-transitory computer-readable recording medium storing a control program for causing equipment provided with a processor to execute a process, the equipment being an information terminal, including a display, that connects to a case search system that searches for medical images by referencing a medical image database in which medical images are registered, the process being executed by a computer of the information terminal, and comprising:

receiving thumbnail images of a plurality of medical images from the case search system, each of the plurality of medical images being received based on a similarity to a target medical image to be interpreted, the plurality of medical images being respectively obtained from a plurality of original images;

displaying a target thumbnail image of the target medical image and the received thumbnail images on a display screen of the display, the display screen including (i) a first display area that displays the target thumbnail image and (ii) a second display area that displays the received thumbnail images including a first thumbnail image and a second thumbnail image, the first thumbnail image and the second thumbnail image being displayed adjacent to each other in the second display area;

detecting an operation of moving the target thumbnail image to an area between the first thumbnail image and the second thumbnail image in the second display area; and after the detecting the operation, (i) moving the second thumbnail image in the second display area and (ii) displaying the target thumbnail image in the second display area between the first thumbnail image and the second thumbnail image, wherein resolutions of the thumbnail images is lower than resolutions of the plurality of medical images, and a resolution of the target thumbnail image is lower than a resolution of the target medical image, the received thumbnail images includes a third thumbnail image, a shape of the second display area is rectangular, a number of images displayed horizontally in the second display area is fixed, in the second display area, the first thumbnail image, the second thumbnail image, and the third thumbnail image are displayed adjacent to each other in order from left to right on a same row, the third thumbnail image is displayed adjacent to a right edge of the second display area, the displaying the target thumbnail image in the second display area between the first thumbnail image and the second thumbnail image after the detecting the first operation includes removing the third thumbnail image from the second display area without displaying the third thumbnail image on the display screen, and the control method further comprises:

detecting a second operation of moving the target thumbnail image to an area between the second thumbnail image and the third thumbnail image in the second display area; and after the detecting the second operation, (i) removing the third thumbnail image from the second display area without displaying the third thumbnail image on the display screen and (ii) displaying the target thumbnail image in the second display area adjacent to the right edge of the second thumbnail image.

15. The non-transitory computer-readable recording medium according to claim 14, wherein the similarity between each of the plurality of medical images and the target medical image is based on (i) a distance between a feature vector obtained from the corresponding original image and a feature vector of a region of interest in the target medical image or (ii) a cosine similarity between the corresponding original image and the target medical image.

* * * * *